United States Patent [19]
Boden et al.
[11] Patent Number: 4,634,547
[45] Date of Patent: Jan. 6, 1987

[54] ORGANOLEPTIC USES OF BICYCLONONENYL ALCOHOLS

[75] Inventors: Richard M. Boden, Ocean; John R. Helm, East Keansburg, both of N.J.

[73] Assignee: International Flavors & Fragrances Inc., New York, N.Y.

[21] Appl. No.: 796,430

[22] Filed: Nov. 8, 1985

Related U.S. Application Data

[63] Continuation-in-part of Ser. No. 763,569, Aug. 8, 1985, Pat. No. 4,608,194.

[51] Int. Cl.[4] ........ A61K 7/46
[52] U.S. Cl. ........ 252/522 R; 252/8.6; 252/174.11; 252/522 A
[58] Field of Search ........ 568/819; 252/522 R, 252/522 A, 174.11, 8.6

[56] References Cited

U.S. PATENT DOCUMENTS

| | | | |
|---|---|---|---|
| 3,636,165 | 1/1972 | Hall | 260/617 F |
| 3,681,464 | 8/1972 | Theimer | 252/522 R |
| 4,493,846 | 1/1985 | Ono et al. | 568/633 X |
| 4,520,032 | 5/1985 | Hall et al. | 426/3 |

OTHER PUBLICATIONS

Turecek et al, Chem. Abs., vol. 85, (1976), 176920V.
Maurer et al., Helvetica Chimica, Acta, vol. 65, (1982), 462–475.
Turecek et al, Tetrahedron Letters, vol. 21, (1980), 637–640.

*Primary Examiner*—Bernard Helfin
*Attorney, Agent, or Firm*—Arthur L. Liberman

[57] ABSTRACT

Described are oxobicyclononane derivatives and mixtures of same having the generic structure:

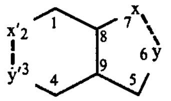

wherein X, Y, X′ and Y′ each represents the moiety having one of the structures:

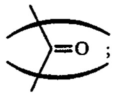

;

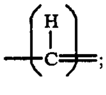

;

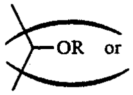

or

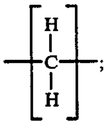

;

wherein one of the dashed lines represents a carbon-carbon single bond and the other of the dashed lines represents a carbon-carbon double bond with the proviso that when X′ and Y′ are each the moiety:

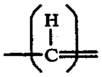

then the dashed line at the "2–3" position is a carbon-carbon double bond and the dashed line at the "6–7" position is a carbon-carbon single bond and one of X or Y has the structure:

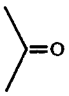

or
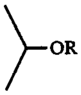

and the other of X or Y has the structure:

;

(Abstract continued on next page.)

and with the further proviso that when X and Y are the moieties:

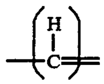

then the dashed line at the "6-7" position is a carbon-carbon double bond and the dashed line at the "2-3" position is a carbon-carbon single bond and one of X' or Y' has the structure:

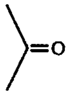

or

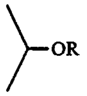

and the other of X' or Y' has the structure:

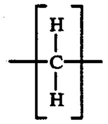

and wherein R represents hydrogen, $C_1$–$C_3$ acyl or $C_1$–$C_2$ alkoxy carbonyl with the major portion of the mixtures defined according to the generic structure:

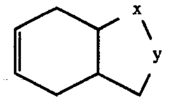

wherein one of X or Y is the moiety:

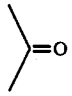

or

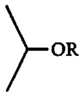

and the other of X or Y is the moiety:

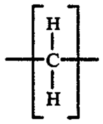

with R being one of hydrogen, $C_1$–$C_3$ acyl or $C_1$–$C_2$ alkoxy carbonyl and uses thereof in augmenting or enhancing the aroma of perfume compositions, perfumed articles, perfumed polymers and colognes.

4 Claims, 36 Drawing Figures

GLC PROFILE FOR EXAMPLE I.
CRUDE

GLC PROFILE FOR EXAMPLE I,
BULKED FRACTIONS 4-7.

NMR SPECTRUM FOR PEAK "20" OF FIG.2, EXAMPLE I.

IR SPECTRUM FOR PEAK "20" OF FIG.2, EXAMPLE I.

NMR SPECTRUM FOR PEAK "21" OF FIG. 2, EXAMPLE I.

IR SPECTRUM FOR PEAK "21" OF FIG. 2, EXAMPLE I.

NMR SPECTRUM FOR PEAK "12" OF FIG. 1, EXAMPLE I.

IR SPECTRUM FOR PEAK "12 OF FIG. I, EXAMPLE I.

FIG. 9
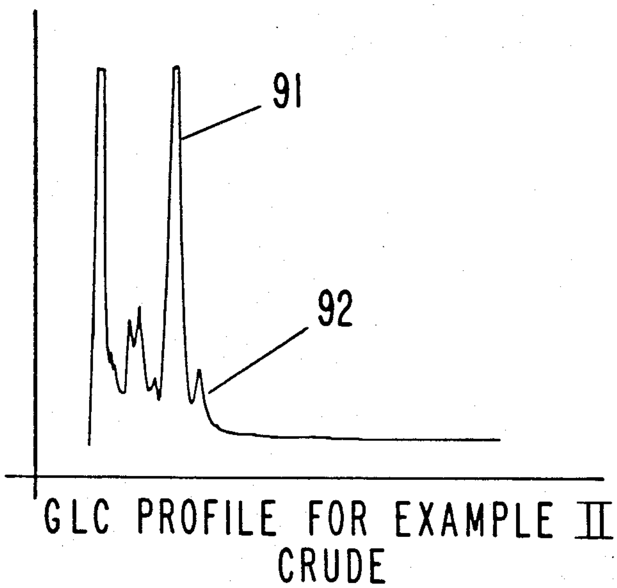
GLC PROFILE FOR EXAMPLE II.
CRUDE
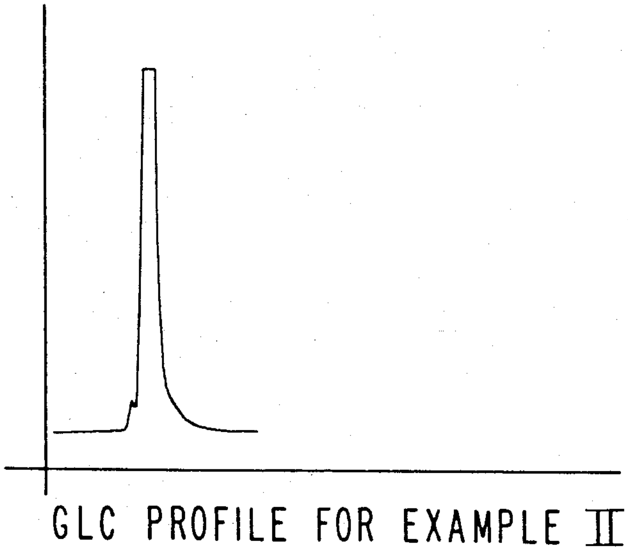
GLC PROFILE FOR EXAMPLE II,
BULKED FRACTIONS 10-14.
FIG. 10

NMR SPECTRUM FOR PEAK "91" OF FIG.9, EXAMPLE II.

I R SPECTRUM FOR PEAK "91" OF FIG.9, EXAMPLE II.

NMR SPECTRUM FOR PEAK "92" OF FIG.9, EXAMPLE II.

IR SPECTRUM FOR PEAK "92" OF FIG.9, EXAMPLE II.

FIG.15
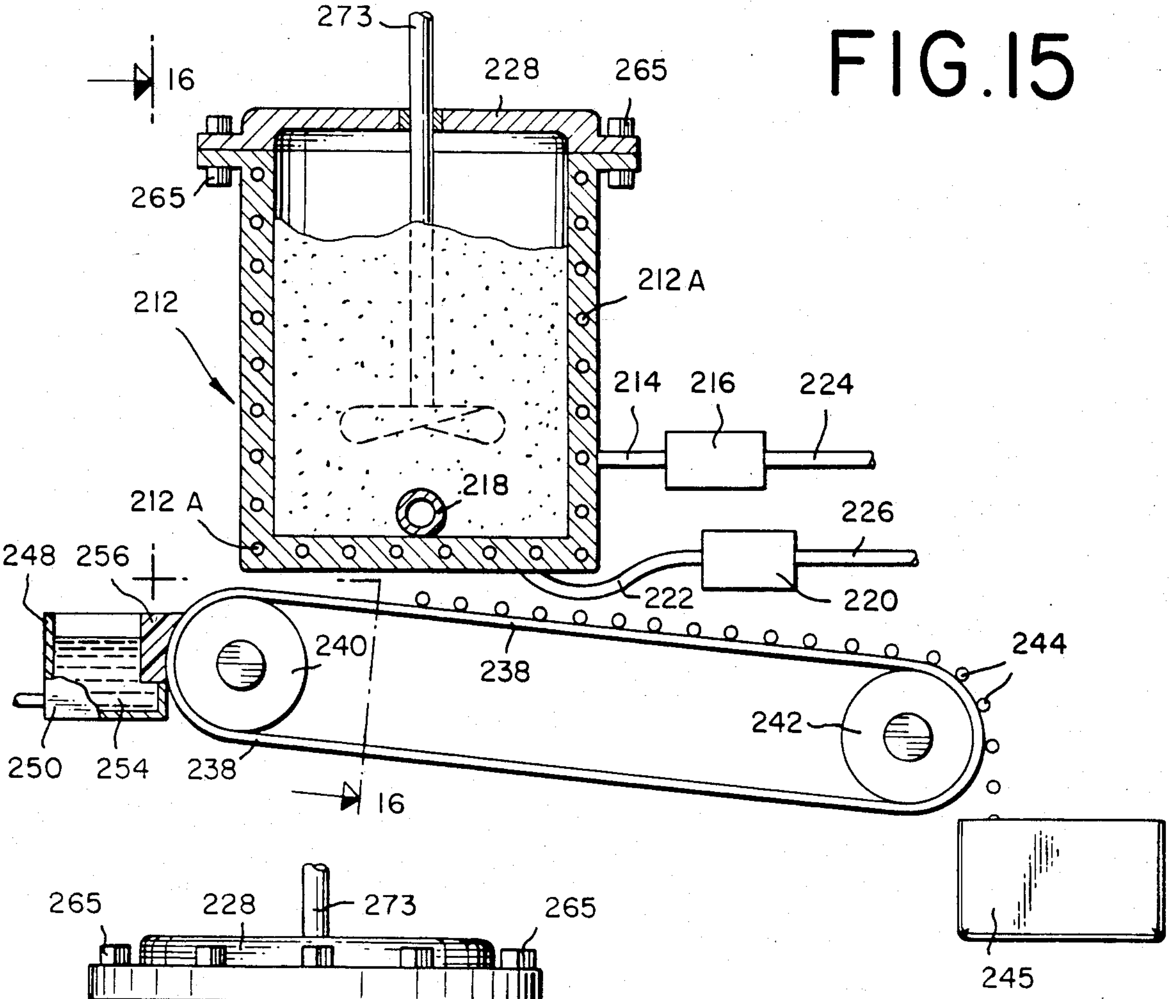
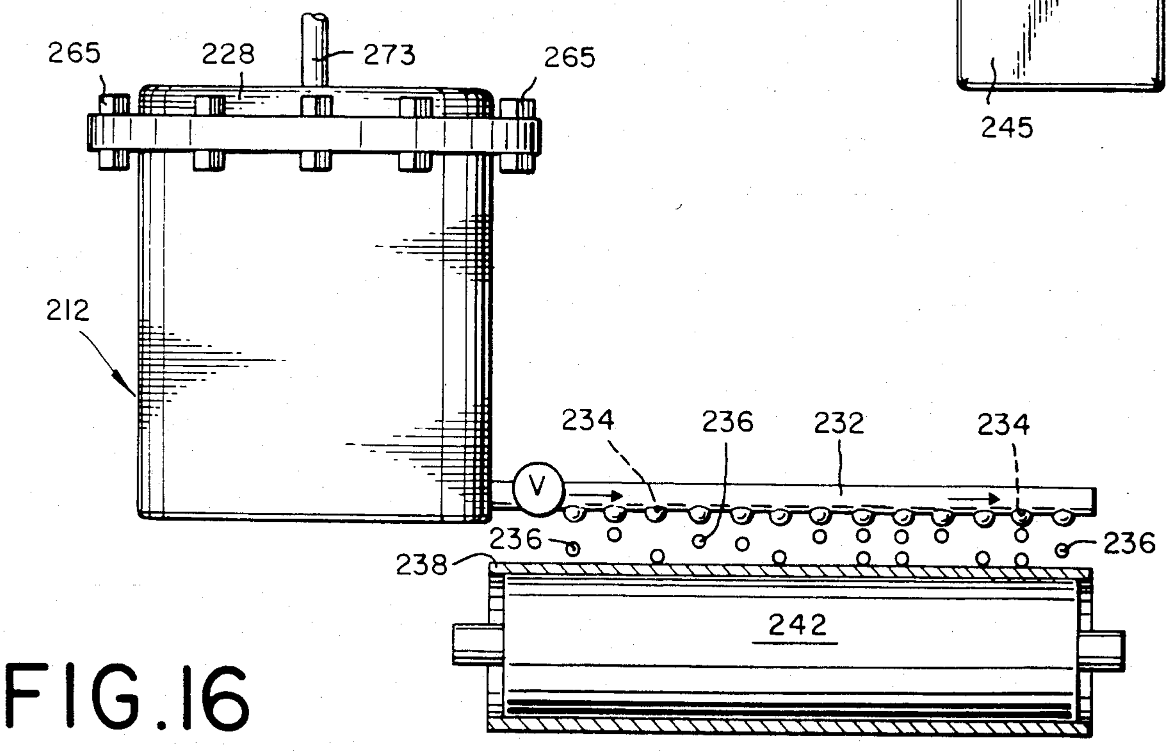
FIG.16

GLC PROFILE FOR EXAMPLE XIII. CRUDE

GLC PROFILE FOR BULKED FRACTIONS 2-5. FIRST DISTILLATION. EX. XIII.

FIG.19 GLC PROFILE FOR BULKED FRACTIONS 6 & 7 OF EXAMPLE XIII.
2nd. DISTILLATION.
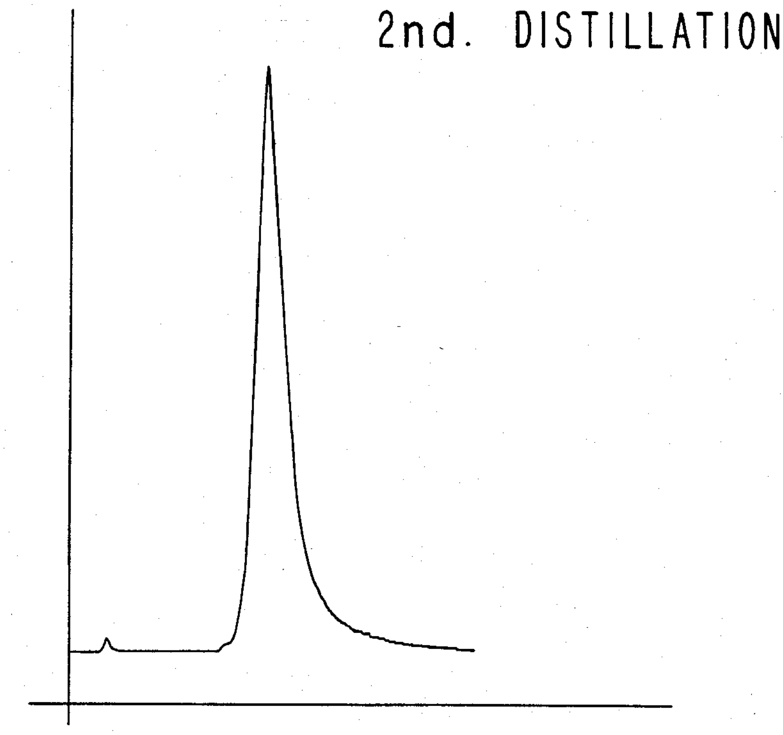
FIG.20
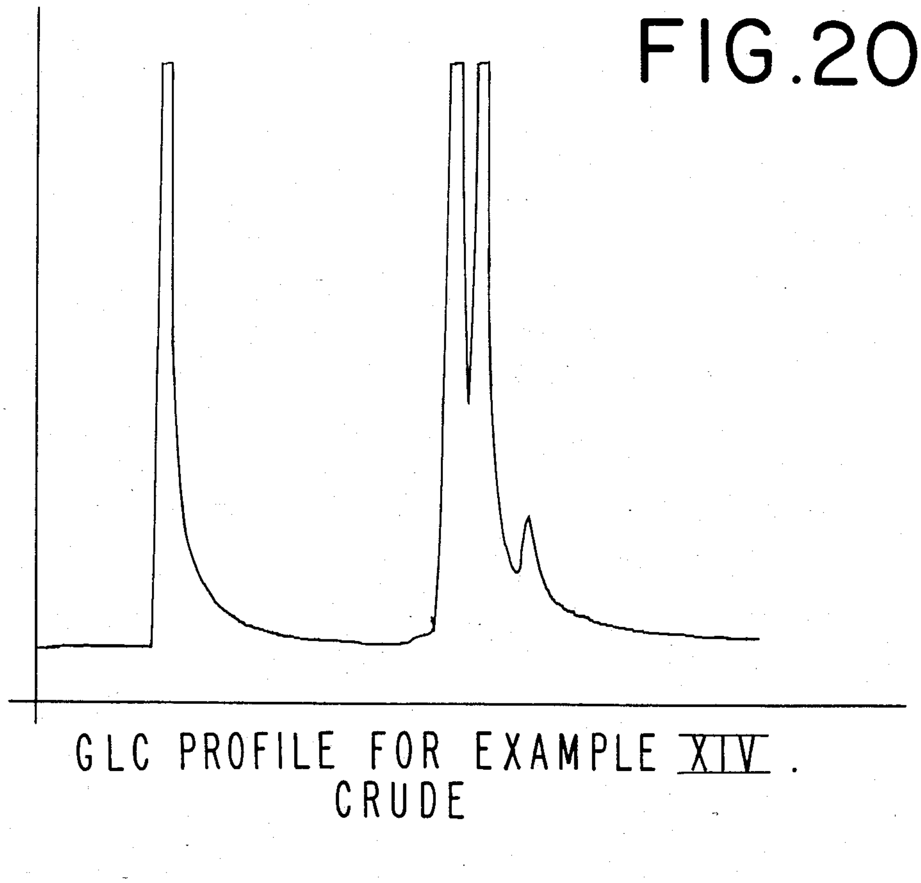
GLC PROFILE FOR EXAMPLE XIV.
CRUDE FIG.21
GLC PROFILE FOR BULKED DISTILLATION FRACTIONS 4-6, OF EXAMPLE XIV.
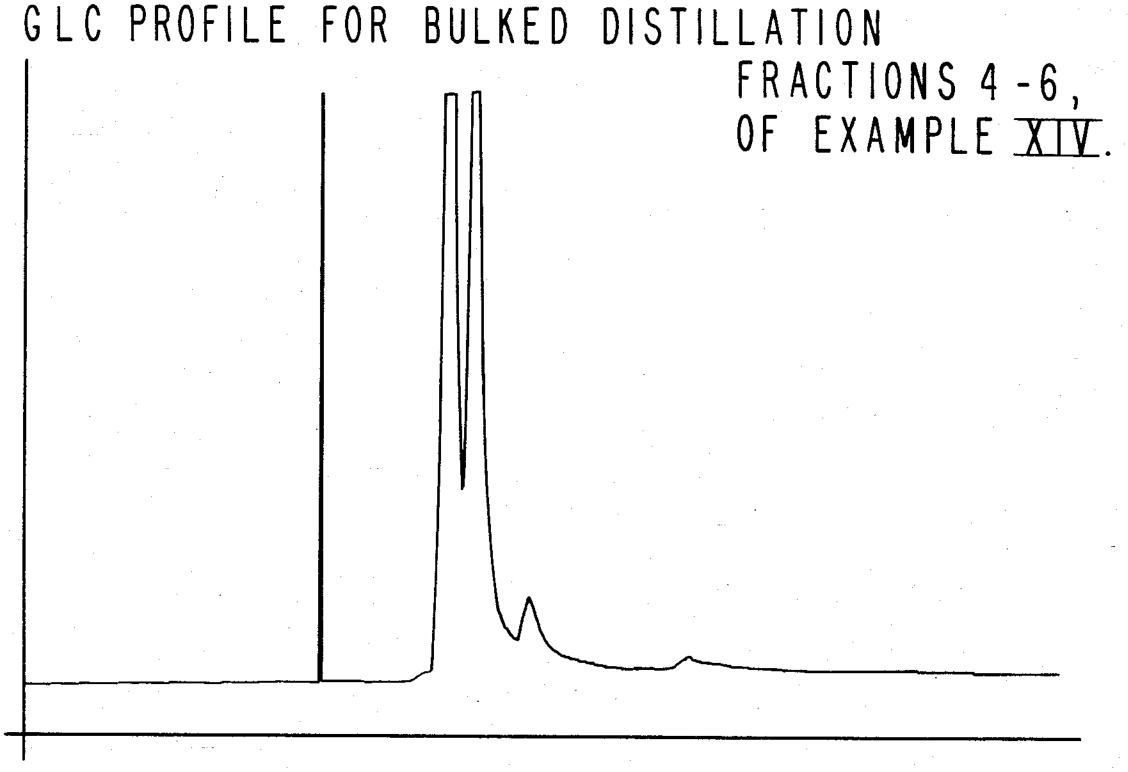
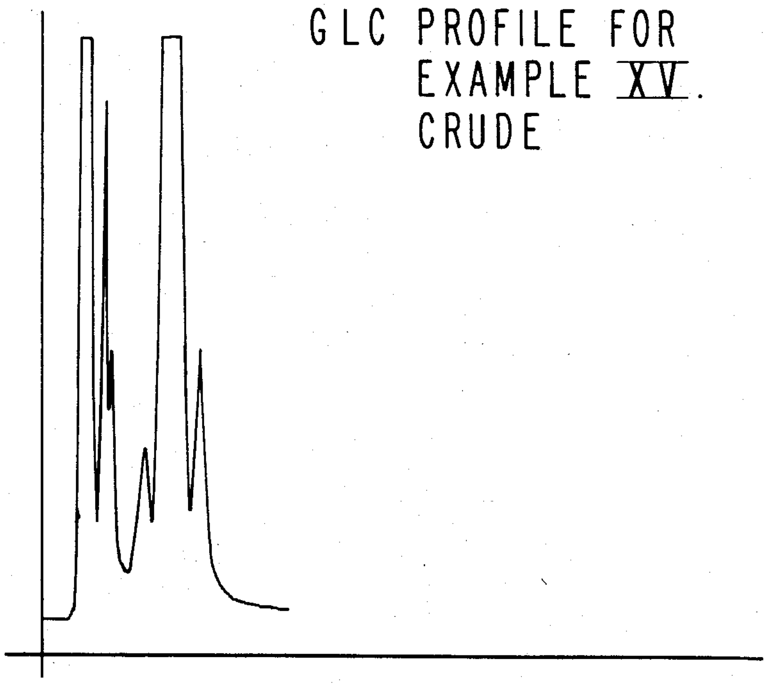
GLC PROFILE FOR EXAMPLE XV. CRUDE
FIG.24

NMR SPECTRUM FOR FRACTION 4 OF EXAMPLE XIV.

IR SPECTRUM FOR FRACTION 4 OF EXAMPLE XIV.

GLC PROFILE FOR BULKED FRACTIONS 2-5 OF EXAMPLE XV. FIRST DISTILLATION.

GLC PROFILE FOR BULKED FRACTIONS 7-10 OF EXAMPLE XV. SECOND DISTILLATION

NMR SPECTRUM FOR FRACTION 8 OF EXAMPLE XV.

IR SPECTRUM FOR FRACTION 8 OF EXAMPLE XV

GLC PROFILE FOR EXAMPLE XVI. CRUDE.

GLC PROFILE FOR BULKED FRACTIONS 3-7, FIRST DISTILLATION, OF EXAMPLE XVI.

GLC PROFILE FOR BULKED FRACTIONS 8-11, OF EXAMPLE XVI. SECOND DISTILLATION.

GLC PROFILE FOR EXAMPLE XVII. CRUDE

NMR SPECTRUM FOR FRACTION 6 OF EXAMPLE XVI.

I R SPECTRUM FOR FRACTION 6 OF EXAMPLE XVI.

GLC PROFILE FOR FRACTION 4 OF EXAMPLE XVII.

GLC PROFILE FOR FRACTION 5 OF EXAMPLE XVII.

ORGANOLEPTIC USES OF BICYCLONONENYL ALCOHOLS

This application is a continuation-in-part of application for U.S. Letters Patent, Ser. No. 763,569 filed on Aug. 8, 1985 and now U.S. Pat. No. 4,608,194.

BACKGROUND OF THE INVENTION

This invention relates to oxobicyclononane derivatives defined according to the structure:

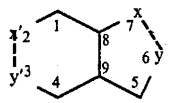

wherein X, Y, X' and Y' each represents the moiety having one of the structures:

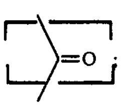 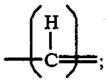 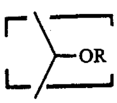 or 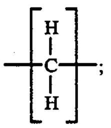

wherein one of the dashed lines represents a carbon-carbon single bond and the other of the dashed lines represents a carbon-carbon double bond with the proviso that when X' and Y' are each the moiety:

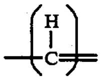

then the dashed line at the "2-3" position is a carbon-carbon double bond and the dashed line at the "6-7" position is a carbon-carbon single bond and one of X or Y has the structure:

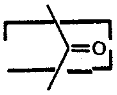 or 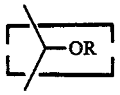

and the other of X or Y has the structure:

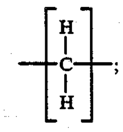

and with the further proviso that when X and Y are the moieties:

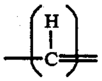

then the dashed line at the "6-7" position is a carbon-carbon double bond and the dashed line at the "2-3" position is a carbon-carbon single bond and one of X' or Y' has the structure:

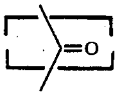 or 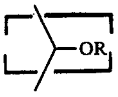

and the other of X' or Y' has the structure:

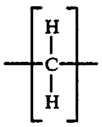

and wherein R represents hydrogen, $C_1$-$C_3$ acyl or $C_1$-$C_2$ alkoxy carbonyl with the major portion of the mixtures defined according to the generic structure:

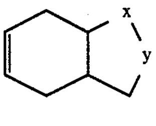

wherein one of X or Y is the moiety:

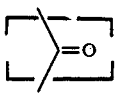 or 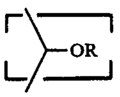

with R being defined as being hydrogen, $C_1$-$C_3$ acyl or $C_1$-$C_2$ alkoxy carbonyl.

Included in the foregoing genus having the structure:

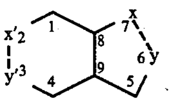

is the genus of compounds having the structure:

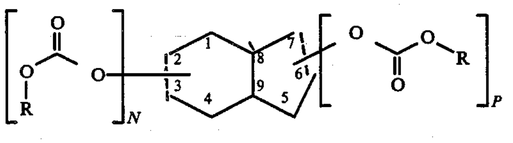

wherein R represents methyl or ethyl; one of the dashed lines represents a carbon-carbon single bond or a carbon-carbon double bond; N and P each represents 0 or 1; the sum of N and P being equal to 1; with the proviso that when N is 1, the dashed line at the "2-3" position is a carbon-carbon single bond and the dashed line at the "6-7" position is a carbon-carbon double bond and uses thereof in augmenting or enhancing the aroma of perfume compositions, colognes and perfumed articles.

Also covered by this invention are the precursor formates defined according to the structure:

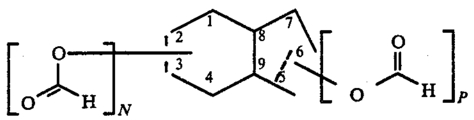

wherein the dashed lines, N and P are defined, supra.

Materials which can provide strawberry, rosy, banana, woody, piney, minty, fruity and jasmine aromas with floral, fruity, spicy, green, hawthorne, ozoney and anisic topnotes are highly desirable in the art of perfumery. Many of the natural substances which provide such fragrance nuances and contribute the desired nuances to perfumery compositions are high in cost, vary in quality from one batch to another and/or are generally subject to the usual variations of natural products.

The prior art contains a large number of teachings regarding the use of organic carbonates in augmenting or enhancing the aroma of perfumes. Thus, U.S. Pat. No. 4,033,993 discloses the use of organic carbonates defined according to the structure:

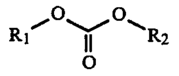

wherein $R_1$ is a moiety having from 8 to 12 carbon atoms selected from the group consisting of alkylcyclohexyl, alkenylcyclohexyl, alkynylcyclohexyl and cycloalkyl and $R_2$ is a moiety selected from the group consisting of alkyl having from 1 to 5 carbon atoms, alkenyl having from 2 to 5 carbon atoms and alkynyl having from 2 to 5 carbon atoms. U.S. Pat. No. 4,033,993 describes, for example, methyl-1-ethynycyclohexyl carbonate having a fruity, herbal complex odor and distinct fragrance of dill. In addition, U.S. Pat. No. 4,033,993 describes methyl cyclooctyl carbonate as having a herbal, natural and complex fragrance which is distinguished by a strong and long clinging flowery jasmine scent and further indicates its use in jasmine perfume compositions. U.S. Pat. No. 4,033,993 describes the preparation of the compounds defined according to the structure:

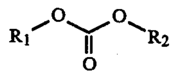

according to the reaction:

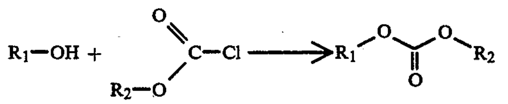

wherein $R_1$ and $R_2$ are defined as above.

In addition, U.S. Pat. No. 4,080,309 described the perfume use of the carbonates defined according to the structure:

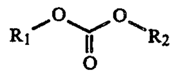

wherein $R_1'$ is a moiety having from 8 to 12 carbon atoms selected from the group consisting of alkylcyclohexyl, alkenylcyclohexyl, alkynylcyclohexyl and cycloalkyl and $R_2'$ is a moiety selected from the group consisting of alkyl having from 1 to 5 carbon atoms, alkenyl having from 2 to 5 carbon atoms and alkynyl having from 2 to 5 carbon atoms. Described in U.S. Pat. No. 4,080,309 are also such compounds as methyl cyclooctyl carbonate and the use thereof in jasmine perfume formulations. As is the case in U.S. Pat. No. 4,033,993, the carbonates of U.S. Pat. No. 4,080,309 are indicated to be prepared according to the reaction:

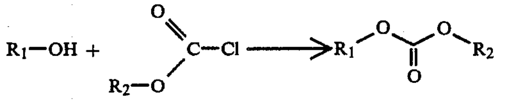

4-Cyclooctenyl alkyl carbonates defined according to the structure:

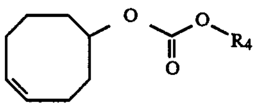

wherein $R_4$ is methyl or ethyl and reaction products including a major proportion of said 4-cyclooctenyl alkyl carbonates and a minor proportion of bicyclooctanyl carbonates having the structure:

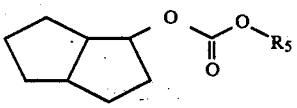

wherein $R_5$ is methyl or ethyl and uses thereof in augmenting or enhancing the aroma of perfume compositions, colognes and perfumed articles are described in U.S. Pat. No. 4,452,730 issued on June 5, 1984.

Tricyclodecane carbonates having the structures:

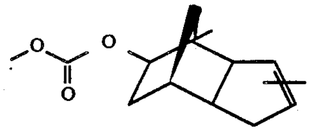

and

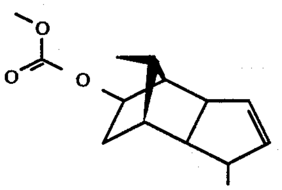

are described as having fruity (apple), anisic-like aromas with dry, hay-like and berry-like undertones.

However, nothing in the prior art describes the oxobicyclononane derivatives of our invention or the organoleptic utilities thereof.

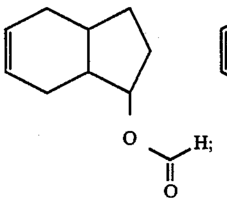
;
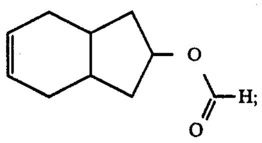
;

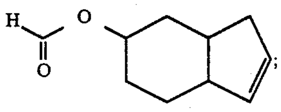
;
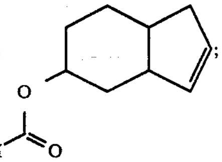
; and

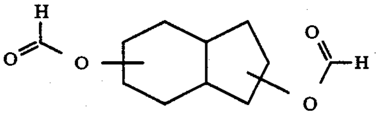

(Conditions: 6'×0.25" 10% SE-30 column programmed at 220° C. isothermal).

Figure 2:
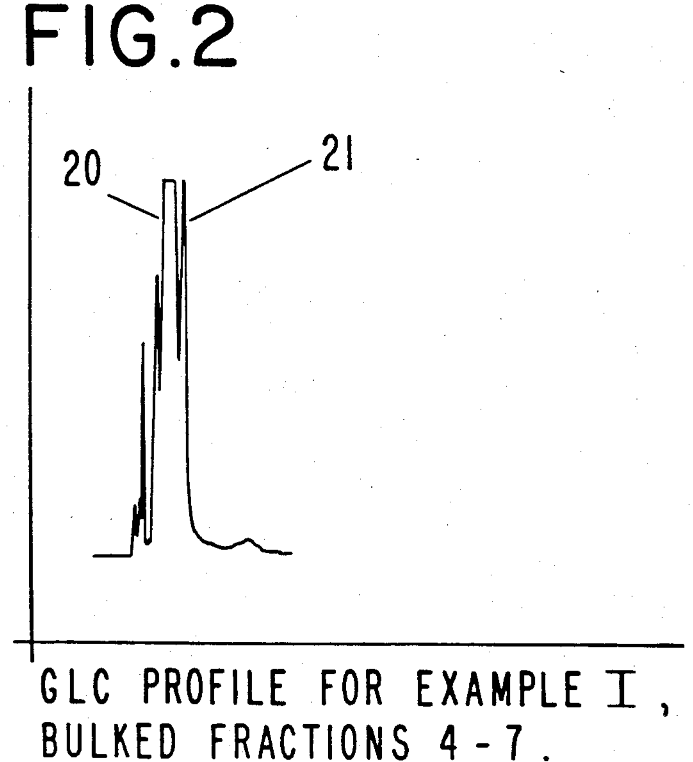

FIG. 2 is the GLC profile for bulked distillation Fractions 4–7 of the reaction product of Example I containing the compounds having the structures:

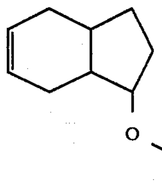
;
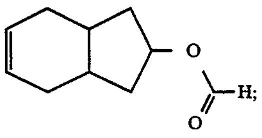
;

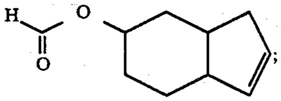
; and
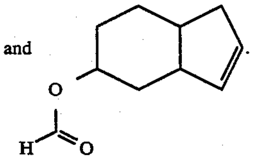

Figure 3:
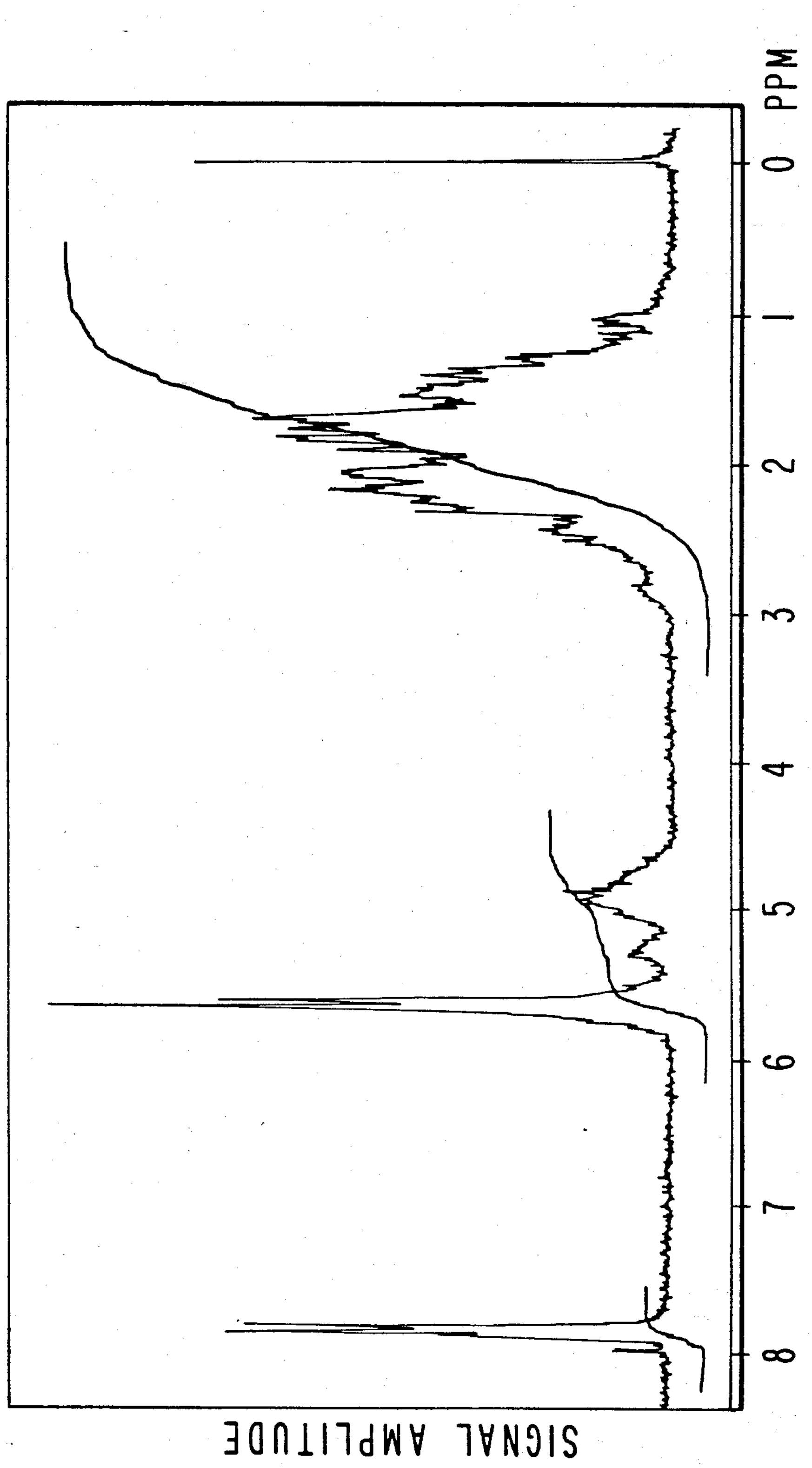

FIG. 3 is the NMR spectrum for the peak indicated by reference numeral 20 on the GLC profile of FIG. 2 containing the compounds having the structures:

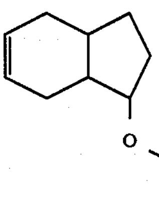
and
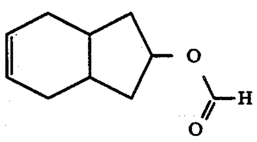

(Conditions: Field strength: 100 MHz; Solvent: $CFCl_3$).

Figure 4:
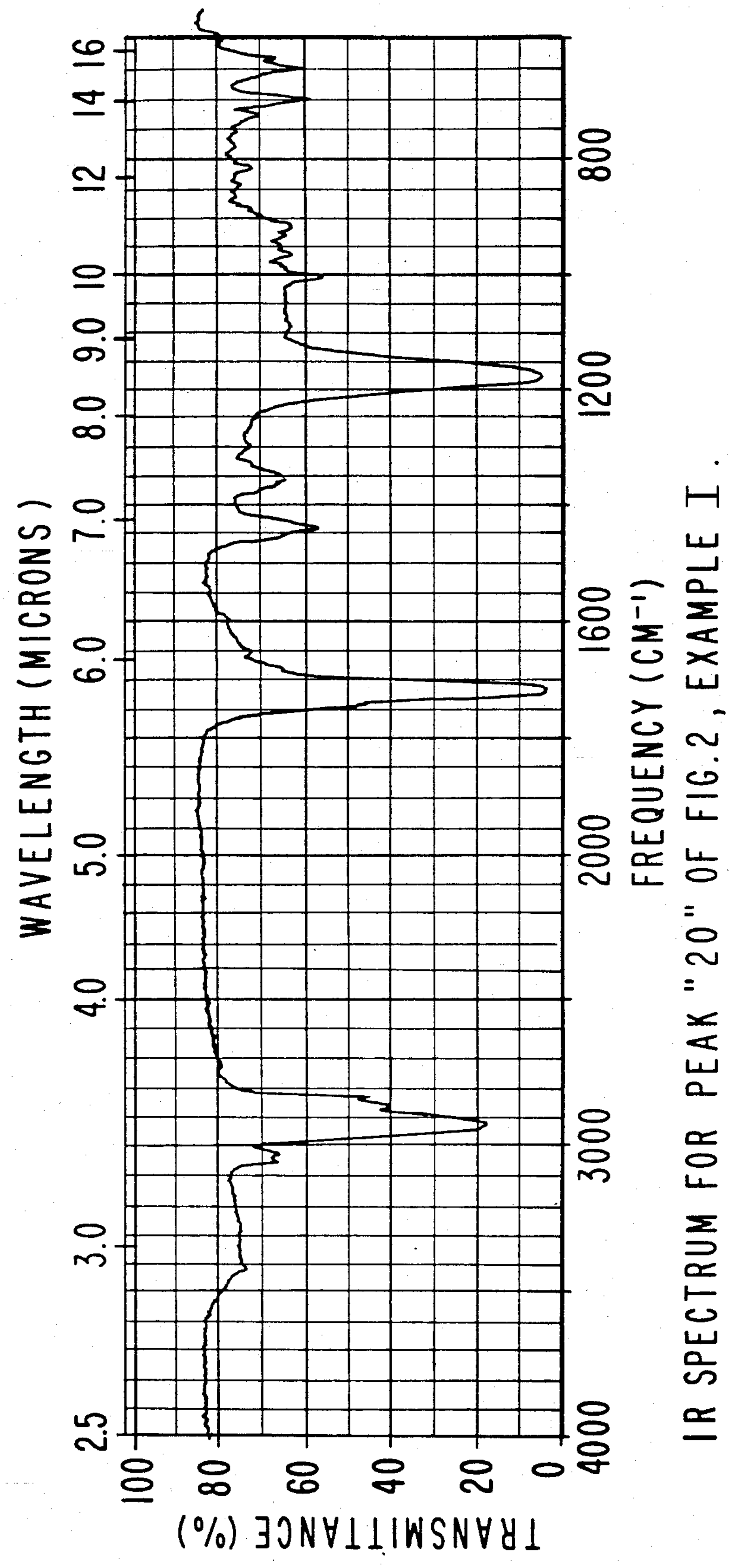

FIG. 4 is the infra-red spectrum for the peak indicated by reference numeral 20 on the GLC profile of FIG. 2 containing the compounds having the structures:

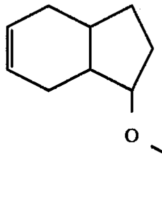
and
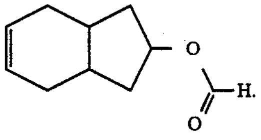

Figure 5:
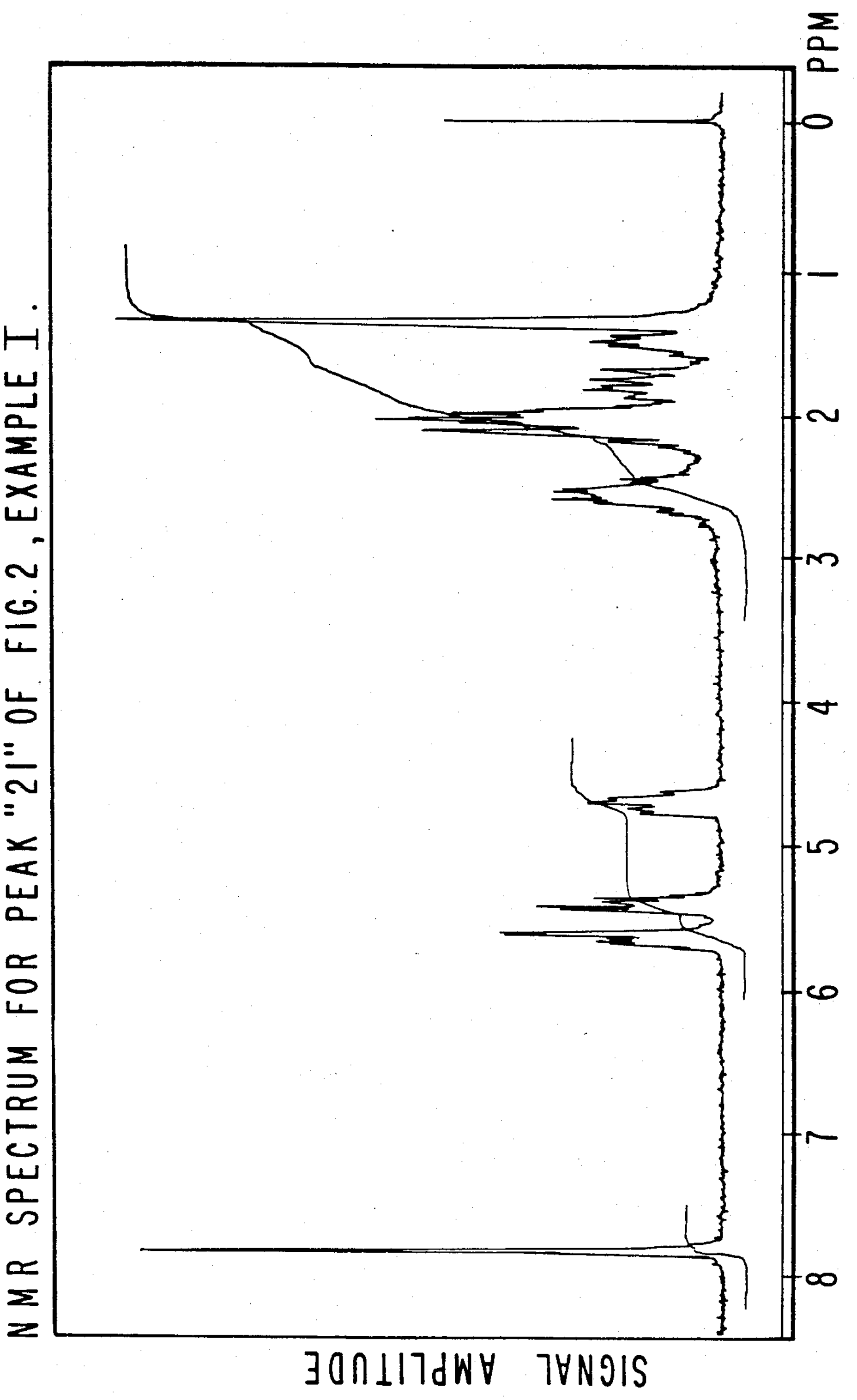

FIG. 5 is the NMR spectrum for the peak indicated by reference numeral 21 on the GLC profile of FIG. 2 containing the compounds having the structures:

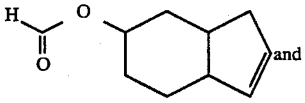
and
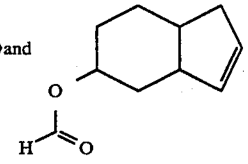

prepared according to Example I (Conditions: Field strength: 100 MHz; Solvent: $CFCl_3$).

Figure 6:
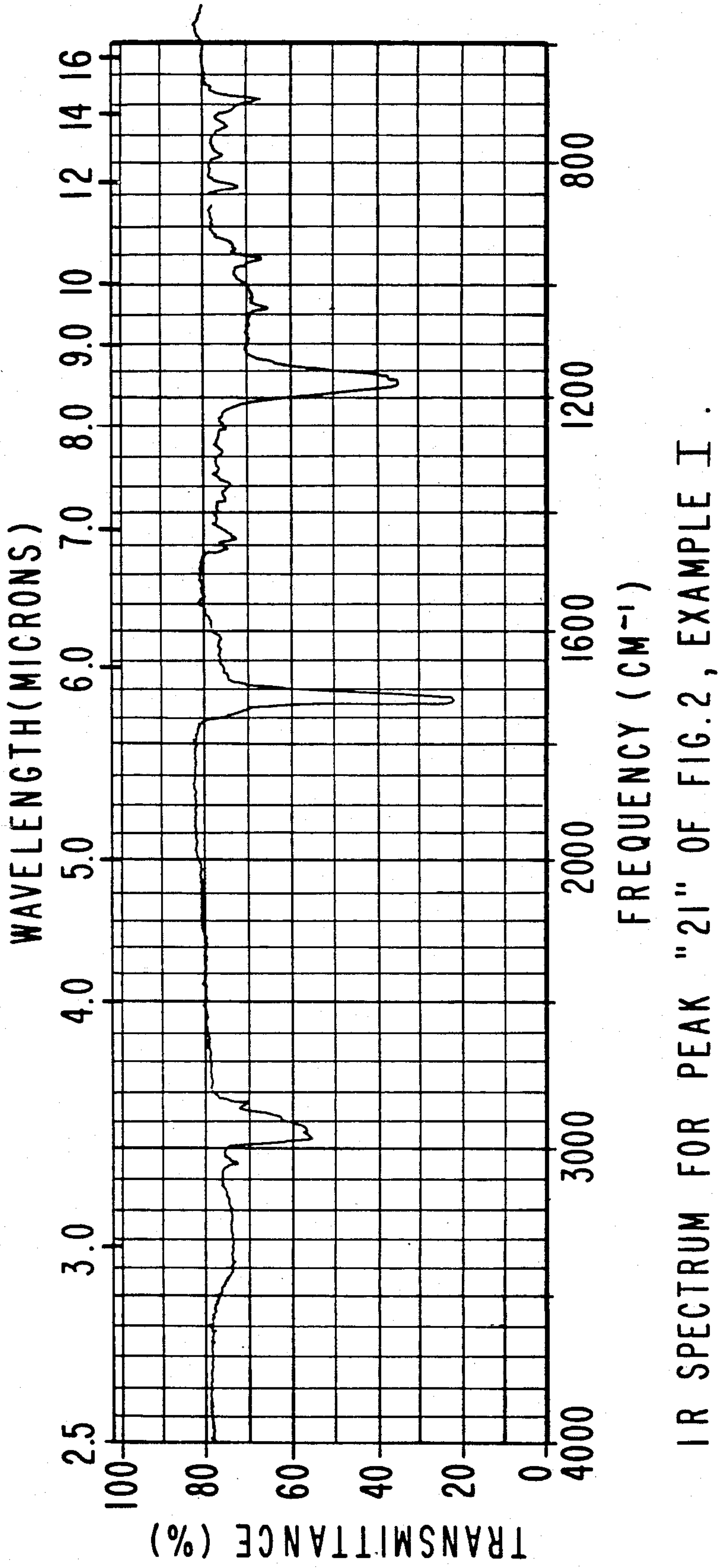

FIG. 6 is the infra-red spectrum for the peak indicated by reference numeral 21 on the GLC profile of FIG. 2 for the compounds having the structures:

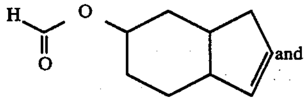
and
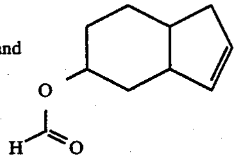

produced according to Example I.

Figure 1:
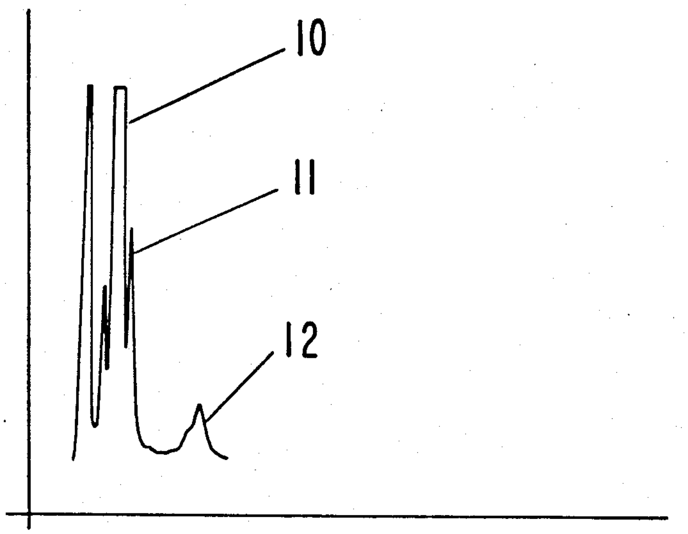
FIG. 1 is the GLC profile for the crude reaction product of Example I containing the mixture of compounds having the structures.
Figure 7:
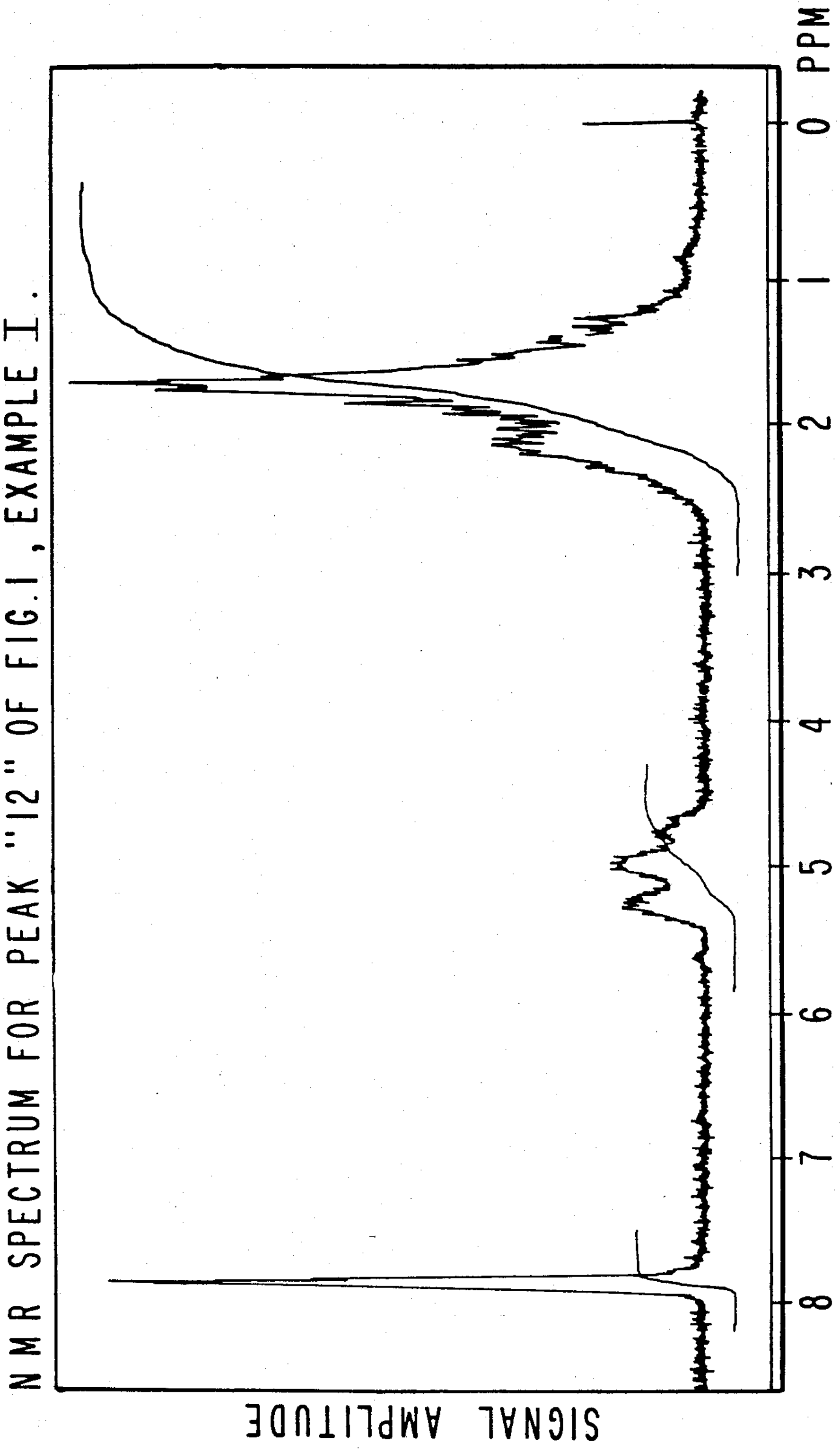

FIG. 7 is the NMR spectrum for the peak indicated by reference numeral 12 on the GLC profile of FIG. 1 prepared according to Example I containing the mixture of compounds having the structure:

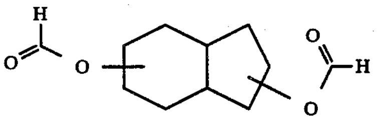

(Conditions: Field strength: 100 MHz; Solvent: $CFCl_3$).

Figure 8:
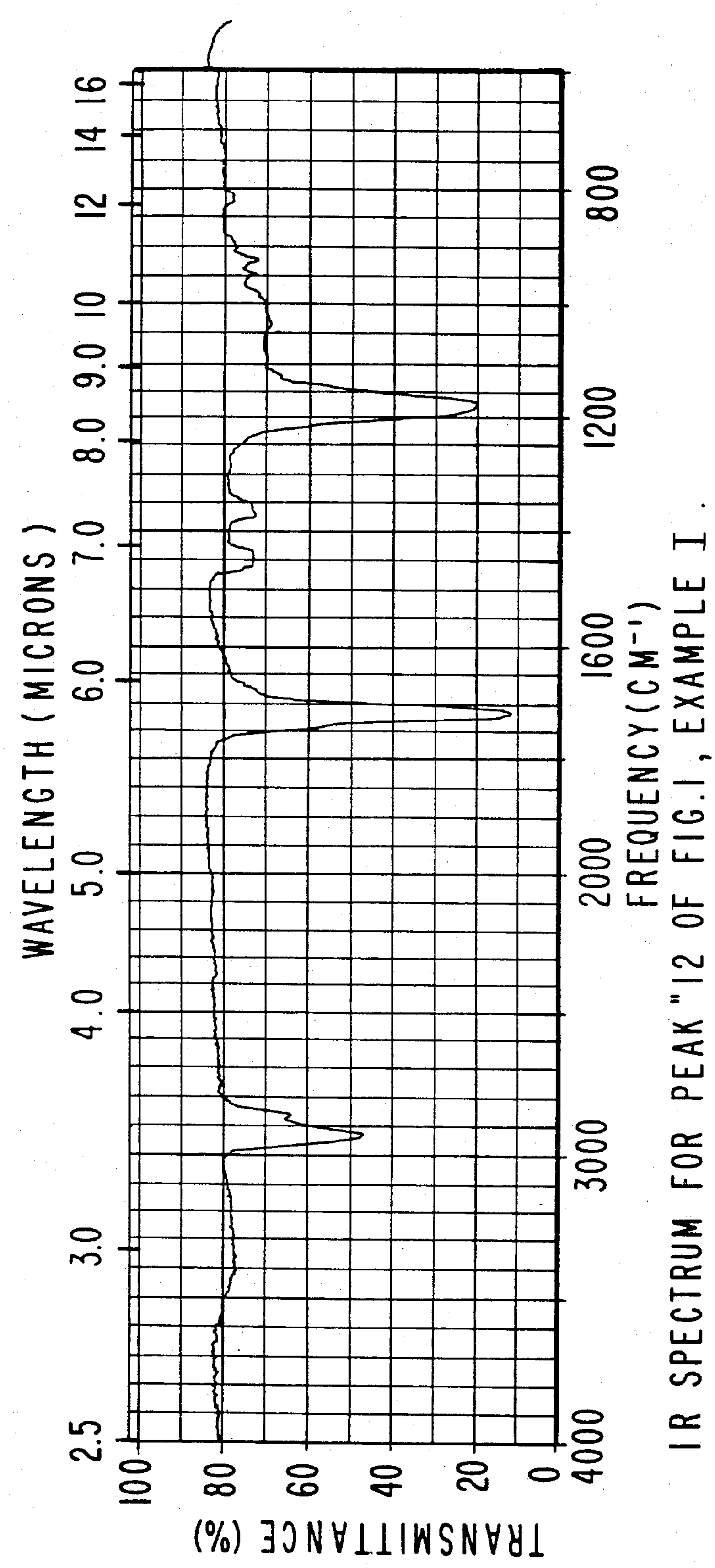

FIG. 8 is the infra-red spectrum for the peak indicated by reference numeral 12 of the GLC profile of FIG. 1 for the mixture of compounds having the structure:

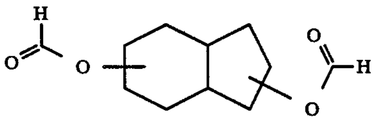

prepared according to Example I.

FIG. 9 is the GLC profile for the crude reaction product of Example II containing the compounds having the structures:

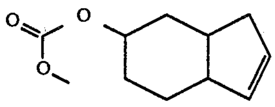;

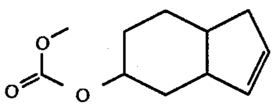;

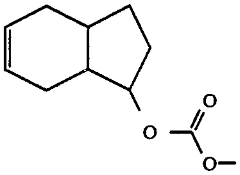; and 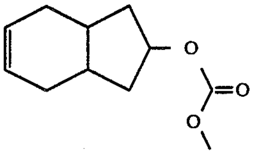

FIG. 10 is the GLC profile for bulked distilation Fractions 10-14 of the distillation of the reaction product of Example II containing the compounds having the structures:

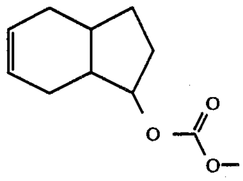 and 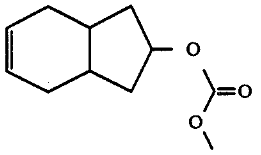

prepared according to Example II (Conditions: 6'×0.25% 10% SE-30 column programmed at 220° C. isothermal).

Figure 11:
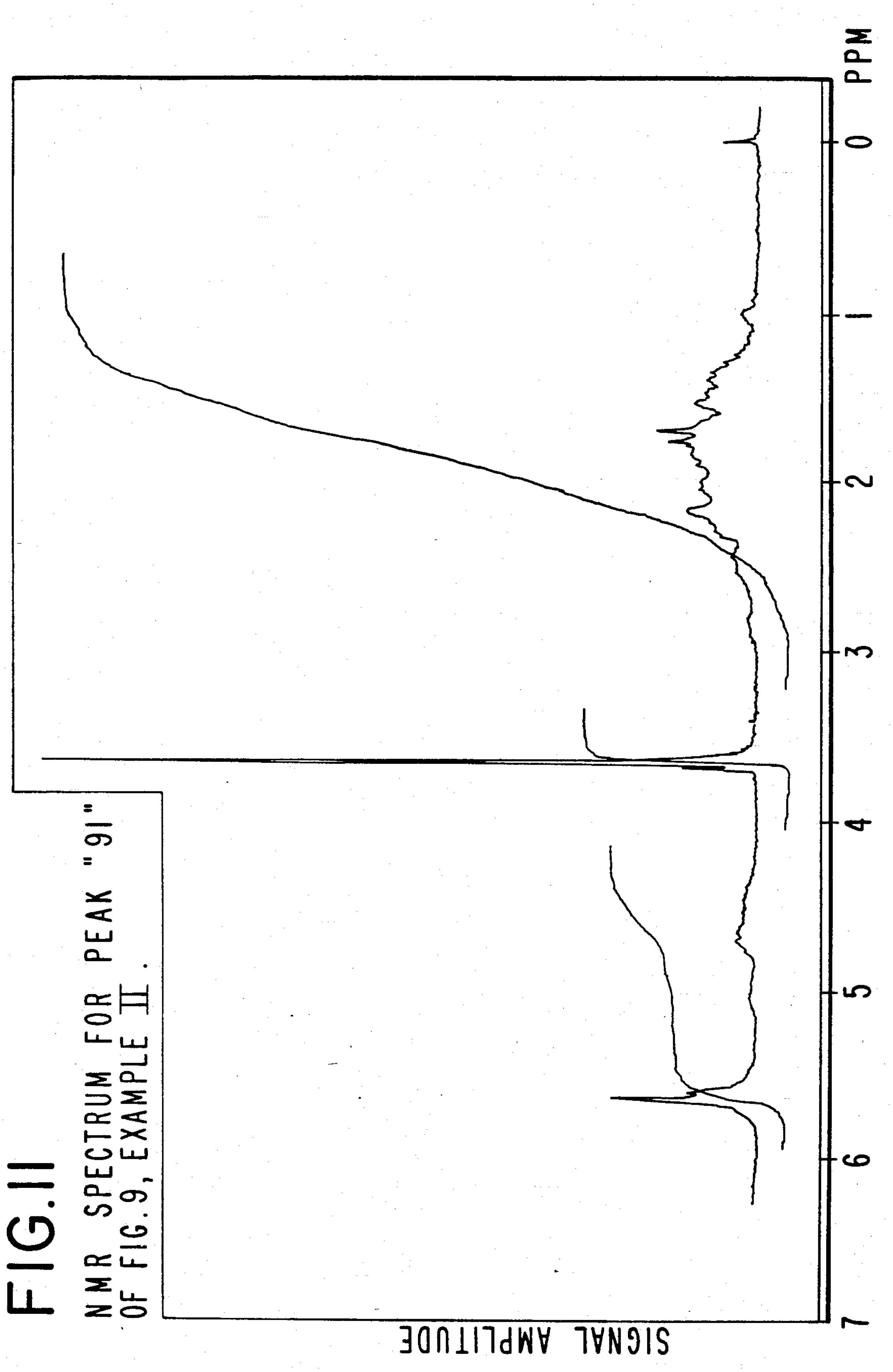

FIG. 11 is the GLC profile for the peak indicated by reference numeral 91 on the GLC profile of FIG. 9 containing the compounds having the structures:

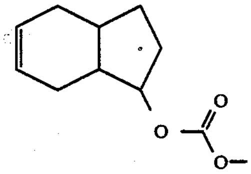 and 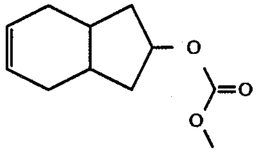

prepared according to Example II (Conditions: Field strength: 100 MHz; Solvent: $CFCl_3$).

Figure 12:
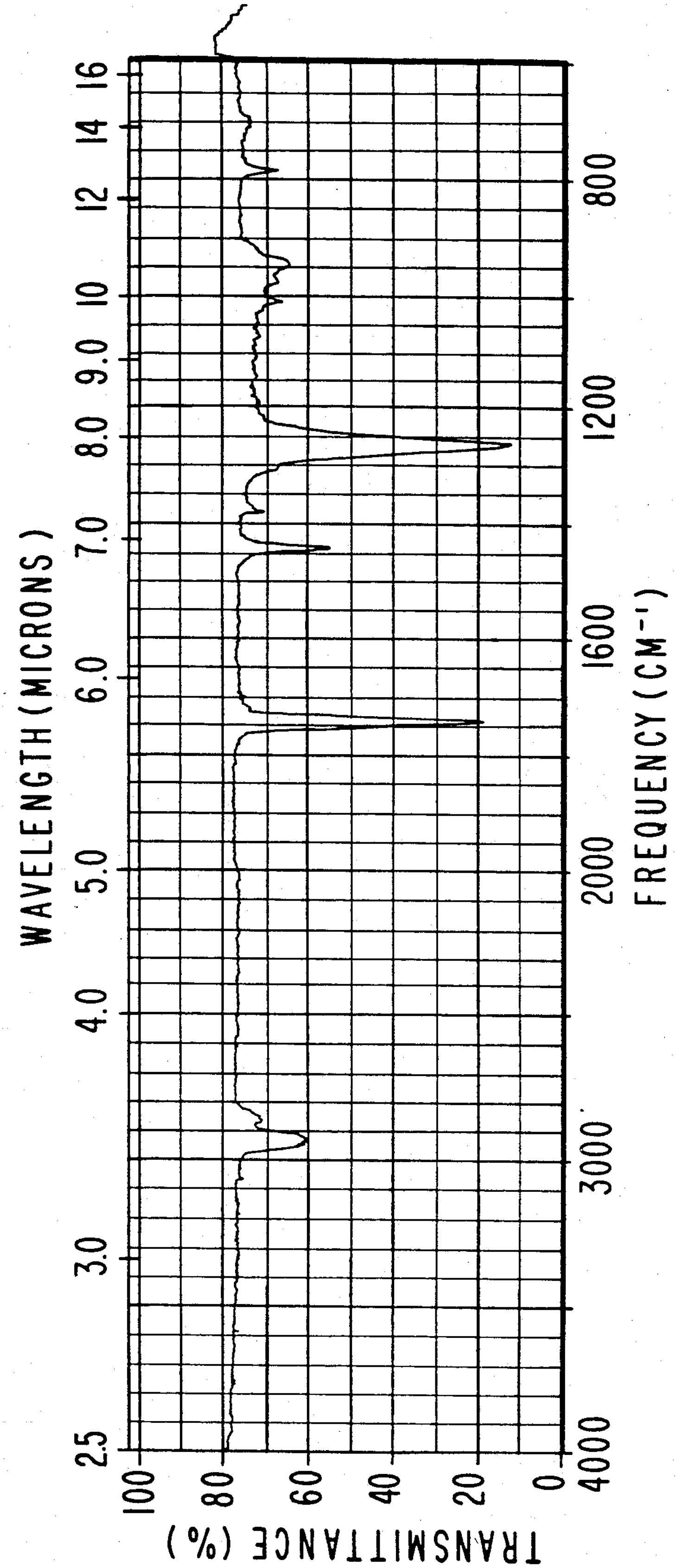

FIG. 12 is the infra-red spectrum for the peak indicated by reference numeral 91 on the GLC profile of FIG. 9 containing the compounds having the structures:

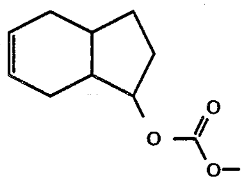 and 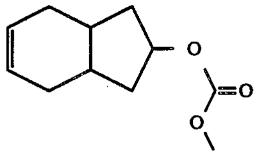

prepared according to Example II.

Figure 13:
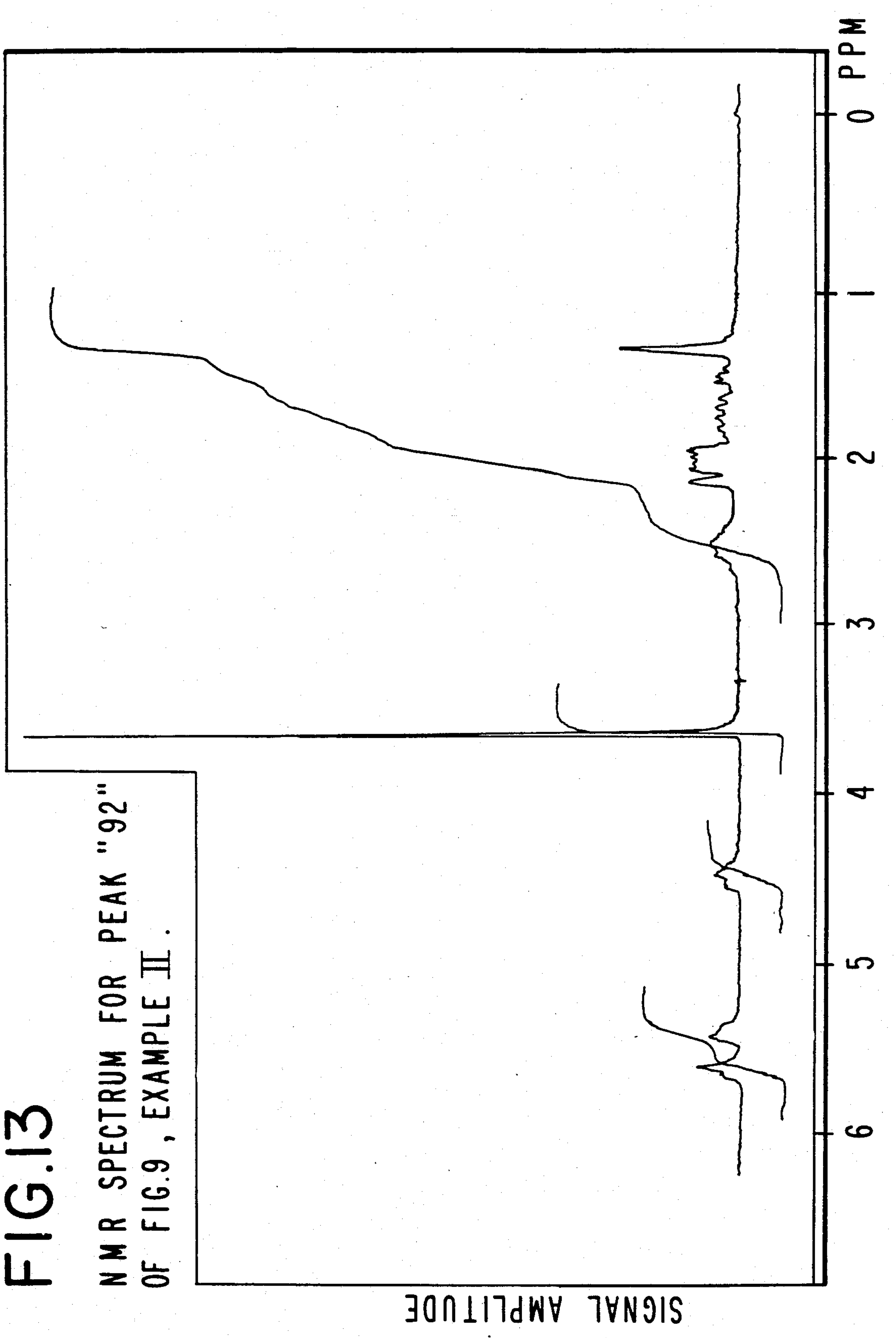

FIG. 13 is the NMR spectrum for the peak indicated by reference numeral 92 on the GLC profile of FIG. 9 containing the compounds having the structures:

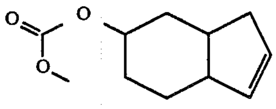 and 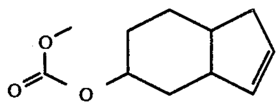

prepared according to Example II (Conditions: Field strength: 100 MHz; Solvent: $CFCl_3$).

Figure 14:
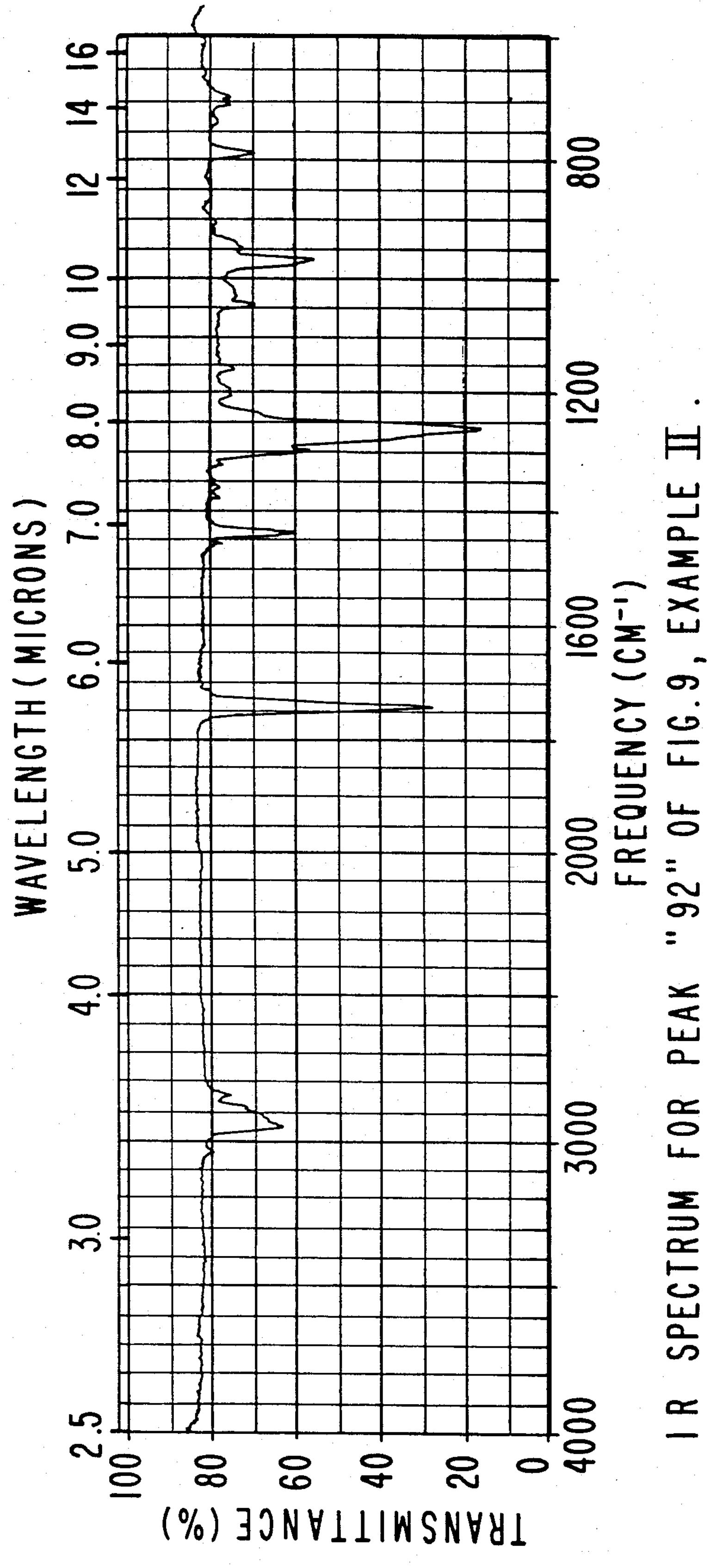

FIG. 14 is the infra-red spectrum for the peak indicated by reference numeral 92 on the GLC profile of FIG. 9 containing the compounds having the structures:

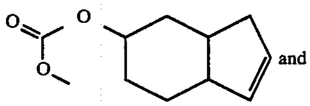 and 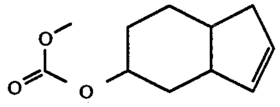.

FIG. 15 is a partial side elevation and partial sectional view of an apparatus for forming scented polymers using at least one of the oxobicyclononane derivatives of our invention.

FIG. 16 is a section taken on line 16—16 of FIG. 15.

Figure 17:
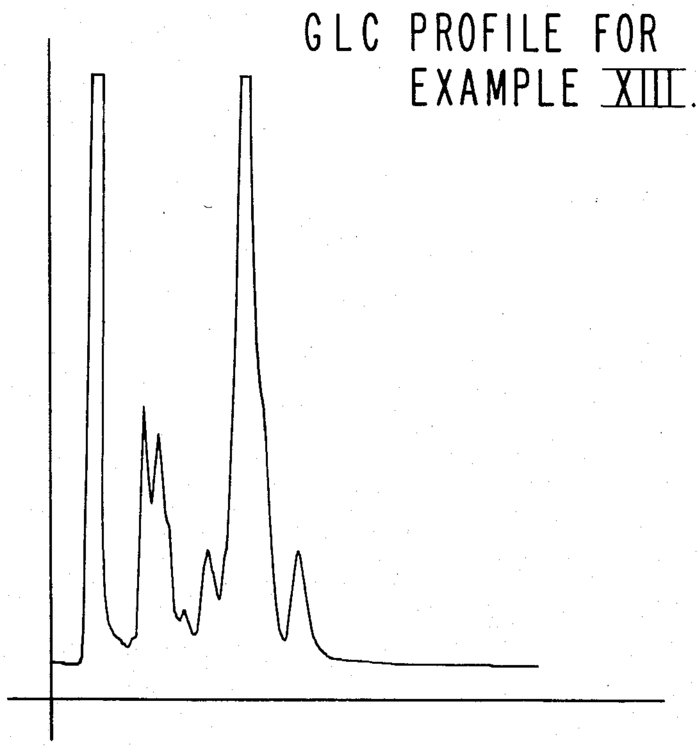

FIG. 17 is the GLC profile for the crude reaction product of Example XIII containing, primarily, the compounds defined according to the structures:

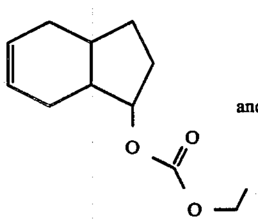 and 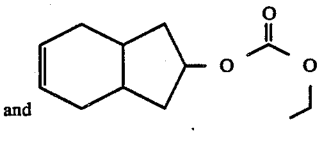

(Conditions: 6'×0.25" 10% SE-30 column programmed at 220° C. isothermal).

Figure 18:
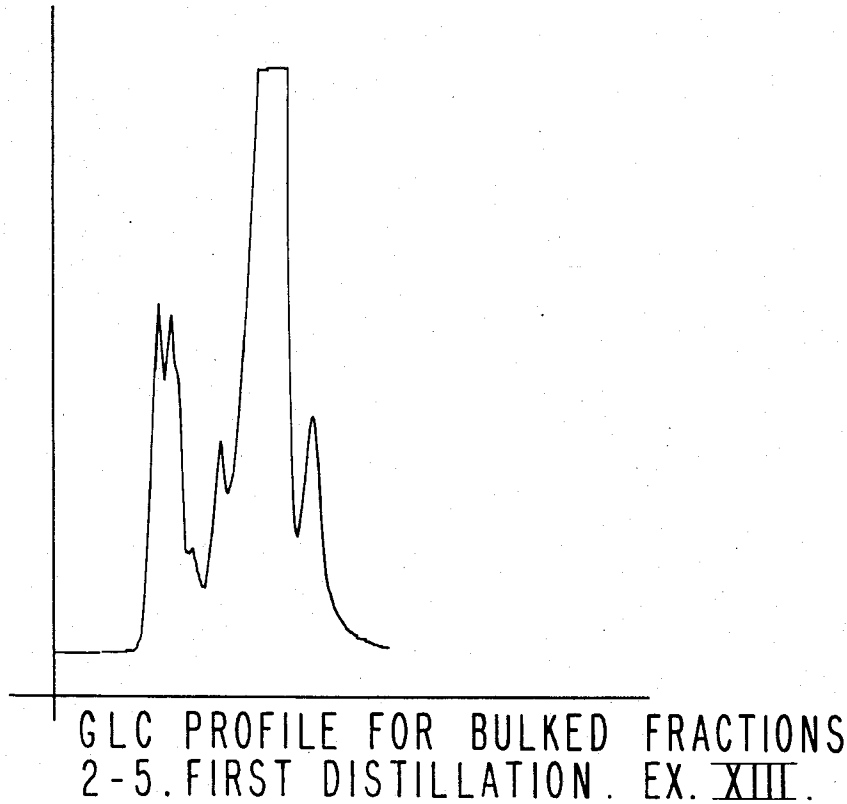

FIG. 18 is the GLC profile for the first distillation of the reaction product of Example XIII, bulked fractions 2-5 containing, primarily, the compounds having the structures:

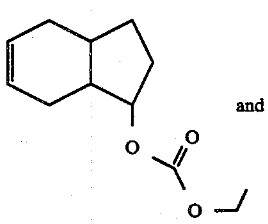 and 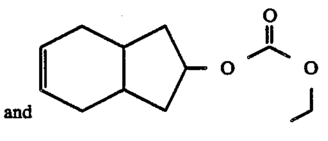

(Conditions: 6'×0.25" 10% SE-30 column programmed at 220° C. isothermal).

FIG. 19 is the GLC profile for bulked fractions 6 and 7 of the first distillation of the reaction product of Example XIII containing, primarily, the compounds having the structures:

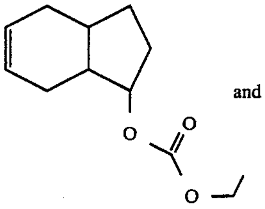
and
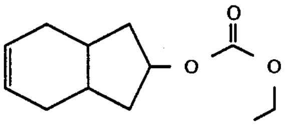

(Conditions: 6'×0.25" 10% SE-30 column programmed at 220° C. isothermal).

FIG. 20 is the GLC profile for the crude reaction product of Example XIV containing, primarily, the compounds having the structures:

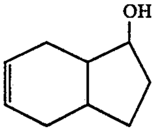
and
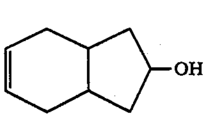

(Conditions: 6'×0.25" 10% SE-30 column programmed at 100°-220° C. at 8° C. per minute).

FIG. 21 is the GLC profile of bulked fractions 4–6 of the distillation of the reaction product of Example XIV containing, primarily, the compounds having the structures:

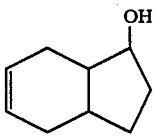
and
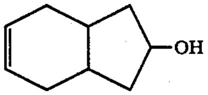

(Conditions: 6'×0.25" 10% SE-30 column programmed at 100°-220° C. at 8° C. per minute).

Figure 22:
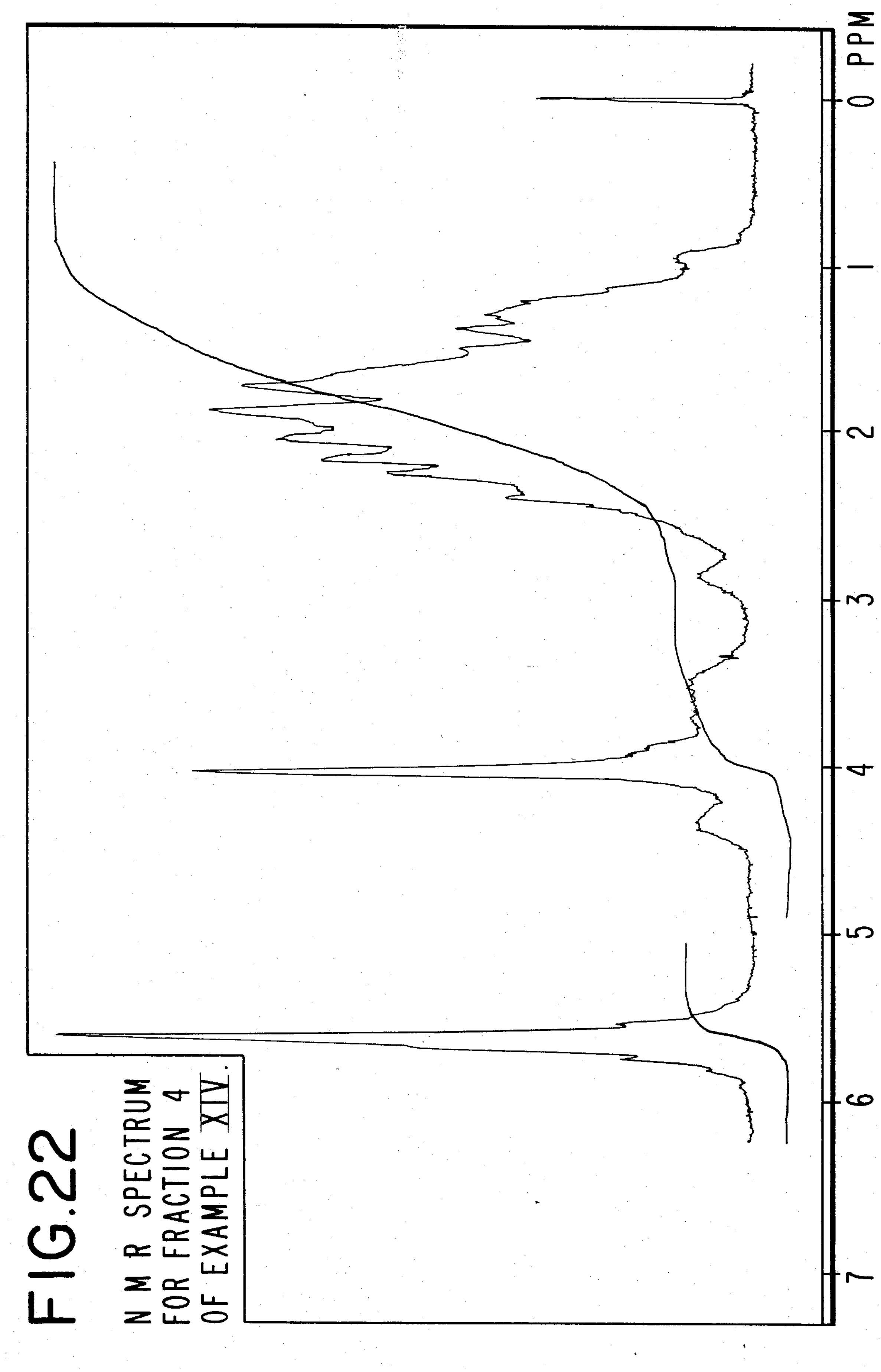

FIG. 22 is the NMR spectrum for fraction 4 of the second distillation of the reaction product of Example XIV containing, primarily, the compounds having the structures:

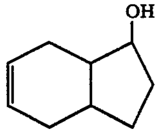
and
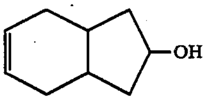

(Conditions: Field strength: 100 MHz; Solvent: $CFCl_3$).

Figure 23:
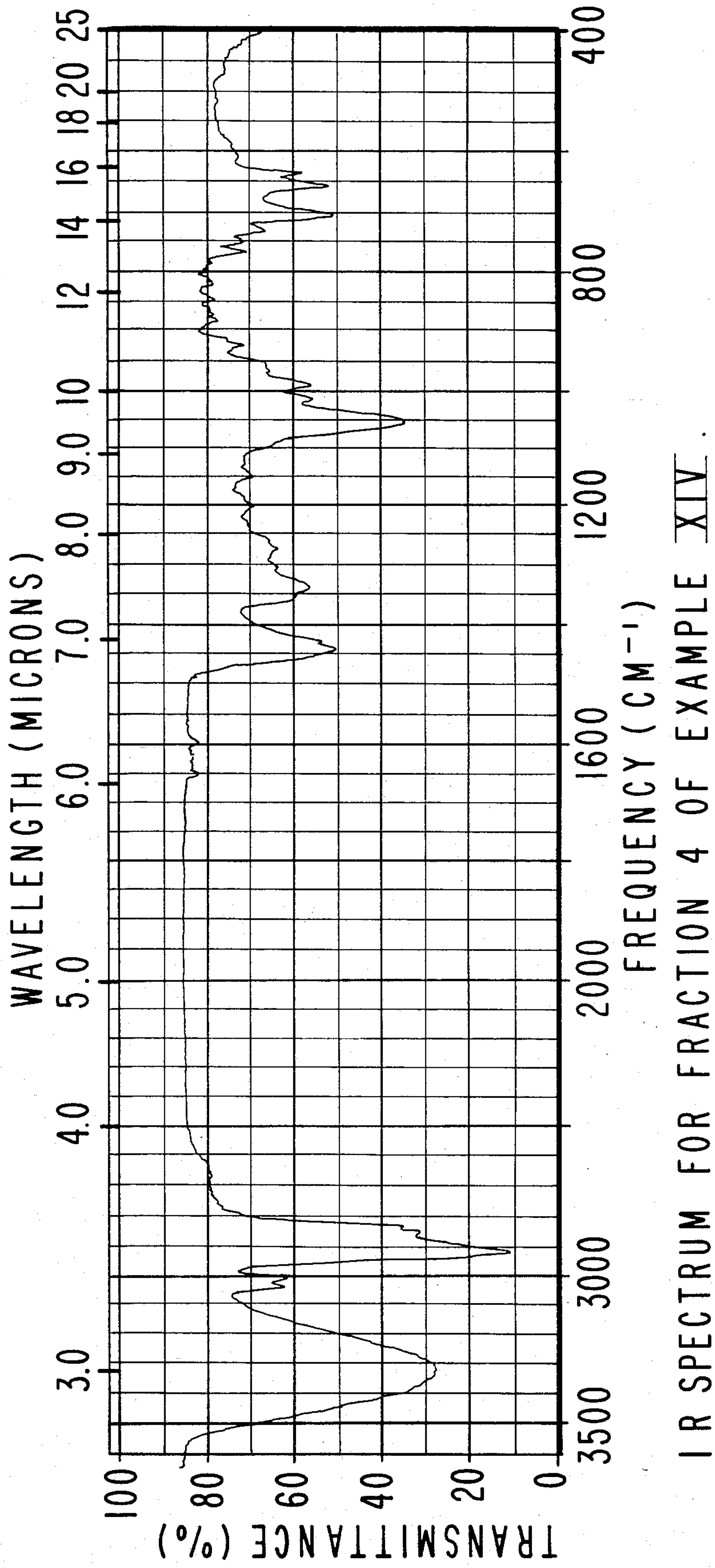

FIG. 23 is the infra-red spectrum for fraction 4 of the distillation of the reaction product of Example XIV containing, primarily, the compounds having the structures:

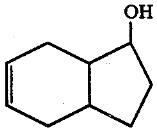
and
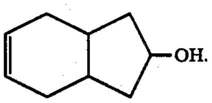

FIG. 24 is the GLC profile for the crude reaction product of Example XV containing, primarily, the compounds having the structures:

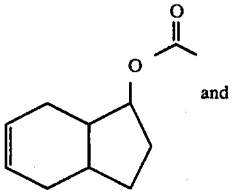
and
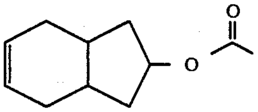

(Conditions: 6'×0.25" 10% SE-30 column programmed at 220° C. isothermal).

Figure 25:
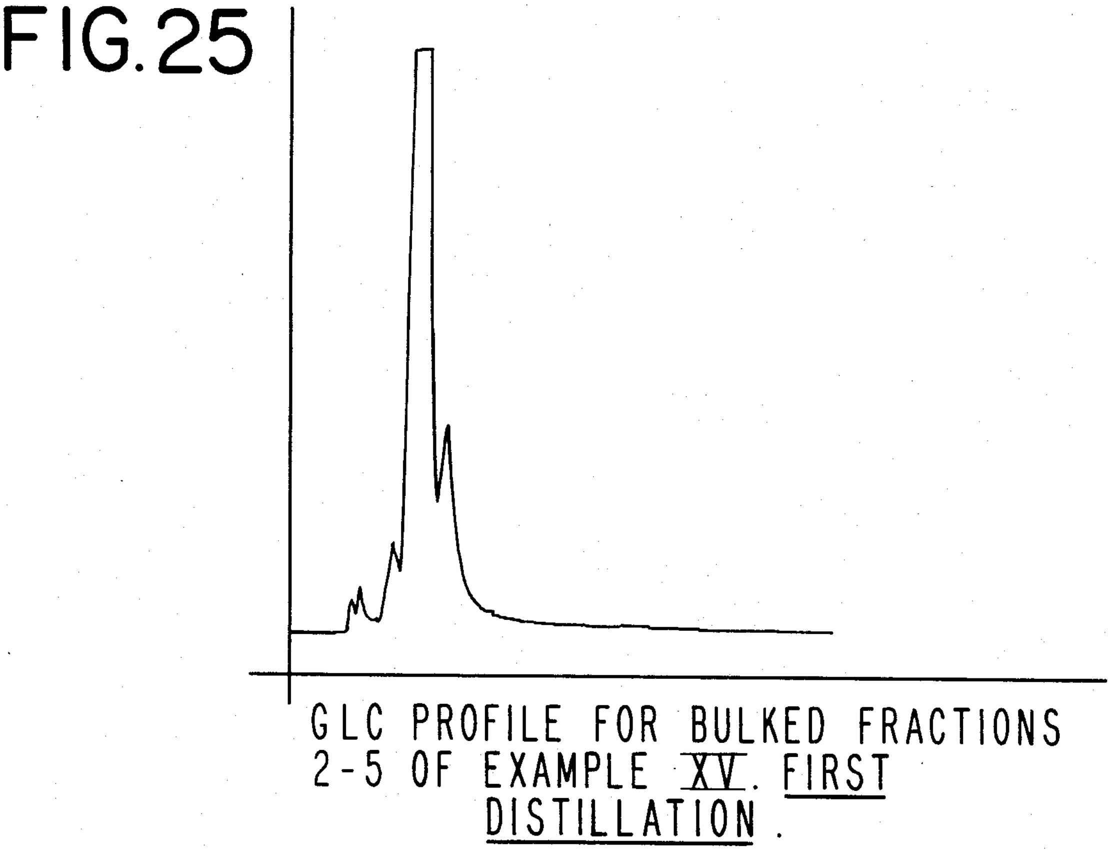

FIG. 25 is the GLC profile for bulked fractions 2–5 of the first distillation of the reaction product of Example XV containing, primarily, the compounds having the structures:

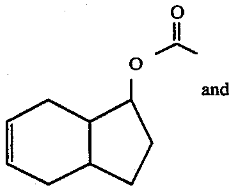
and
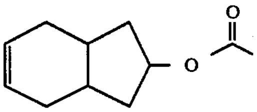

(Conditions: 6'×0.25" 10% SE-30 column programmed at 220° isothermal).

Figure 26:
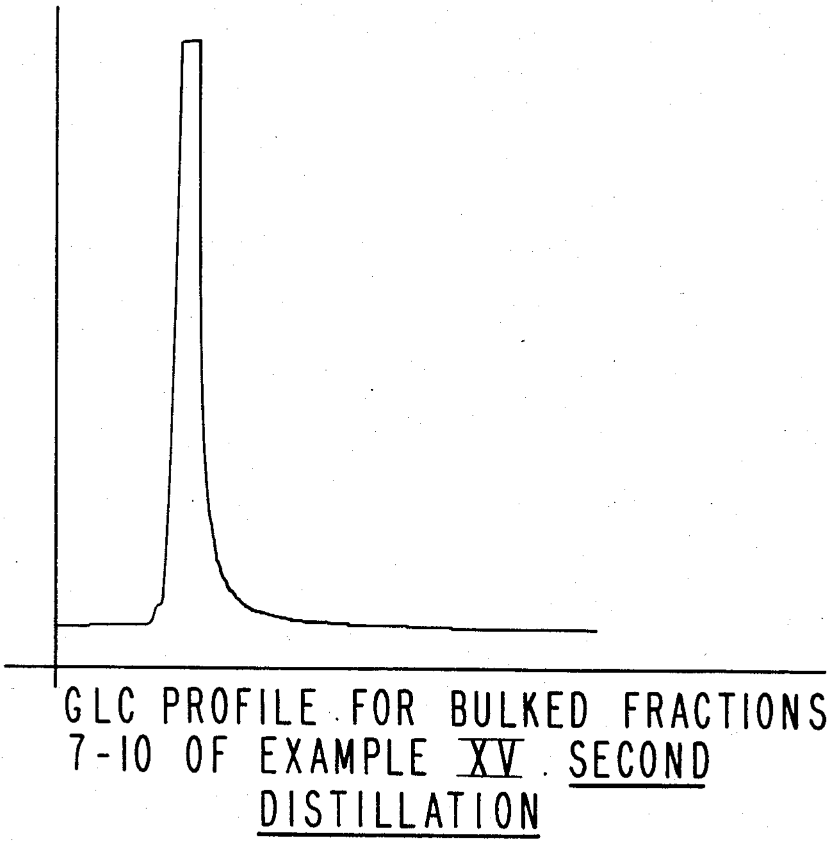

FIG. 26 is the GLC profile for bulked fractions 7–10 of the second distillation of the reaction product of Example XV containing, primarily, the compounds having the structures:

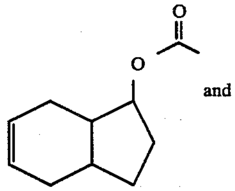
and
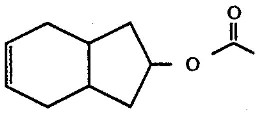

(Conditions: 6'×0.25" 10% SE-30 column programmed at 220° isothermal).

Figure 27:
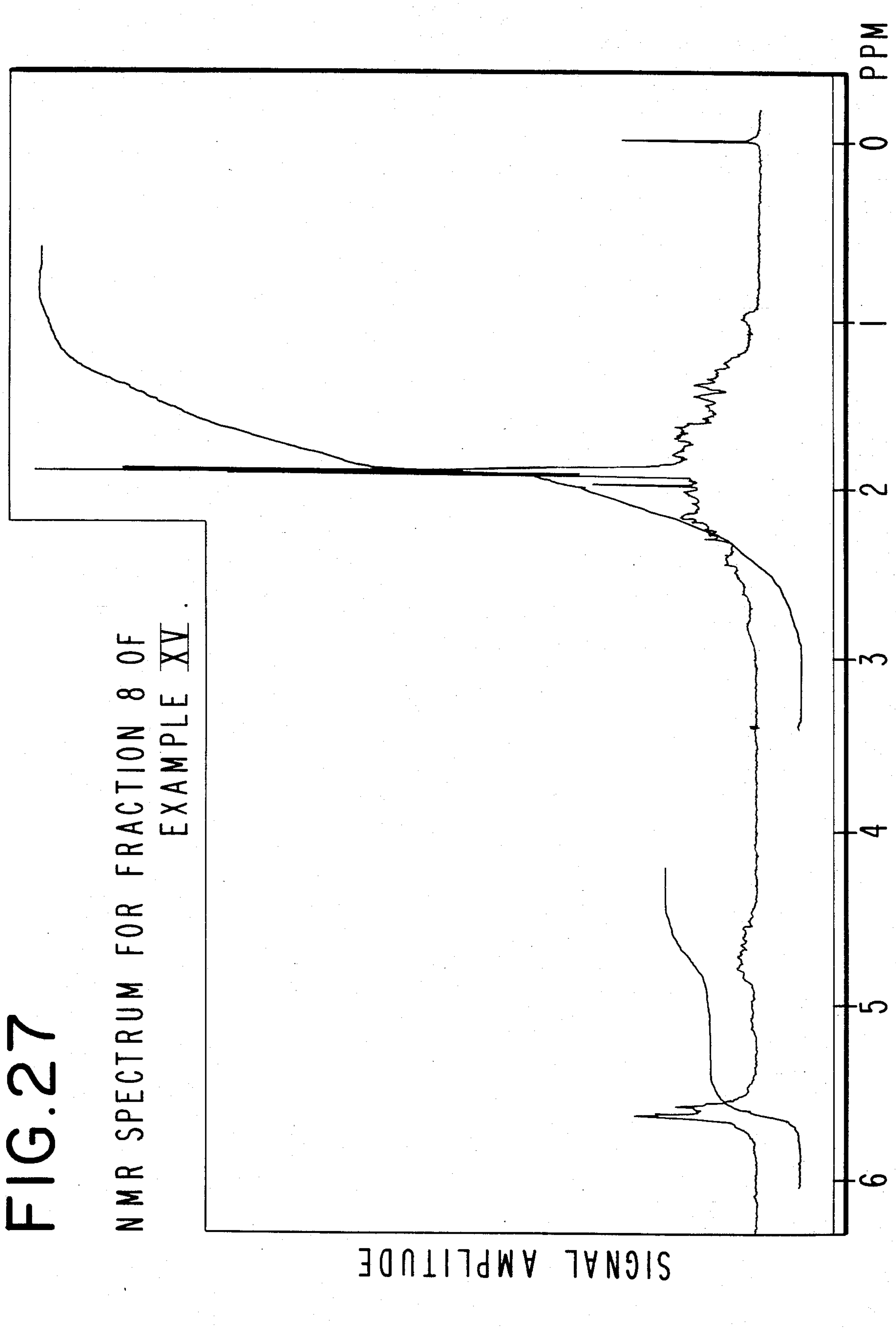

FIG. 27 is the NMR spectrum for fraction 8 of the second distillation of the reaction product of Example XV containing, primarily, the compounds having the structures:

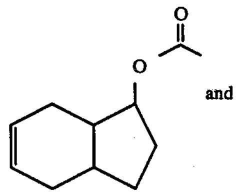
and
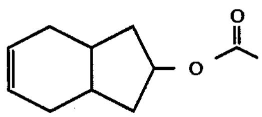

(Conditions: Field strength: 100 MHz; Solvent: $CFCl_3$).

Figure 28:
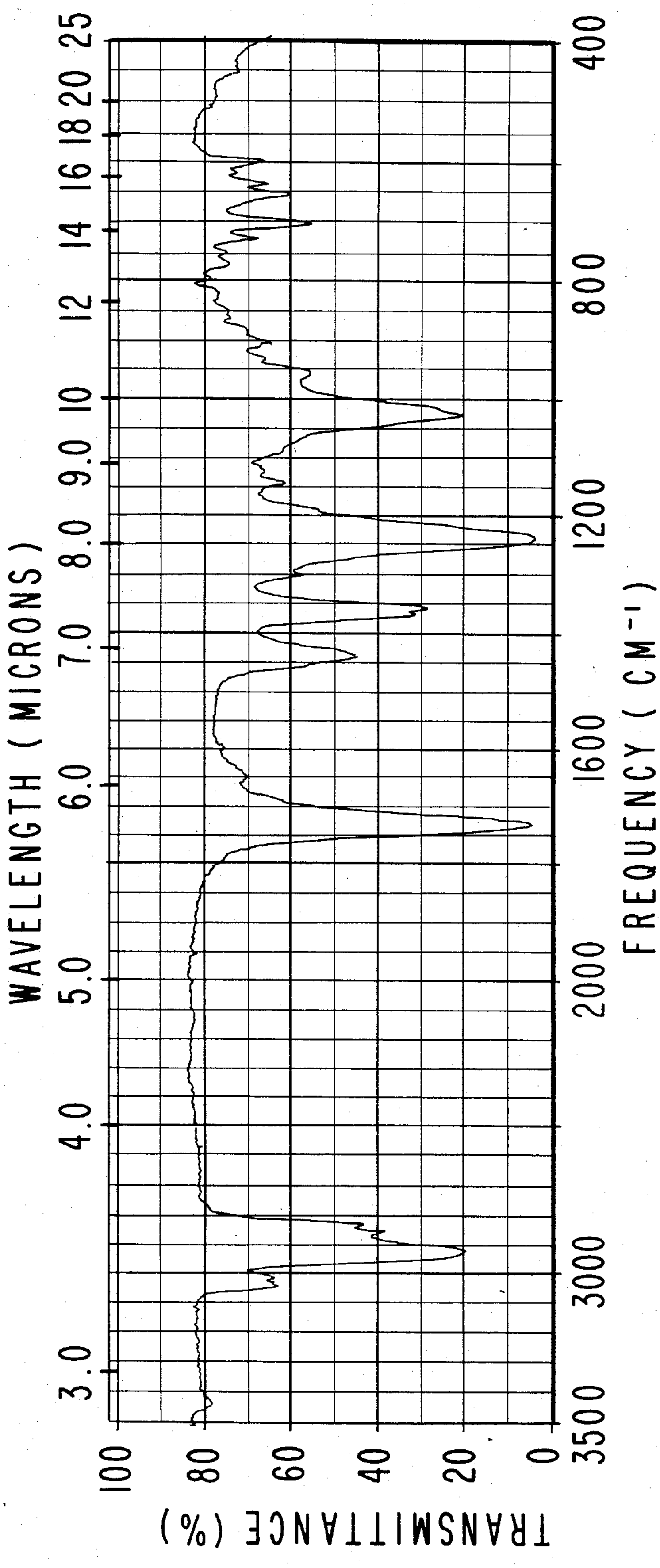

FIG. 28 is the infra-red spectrum for fraction 8 of the second distillation of the reaction product of Example XV containing, primarily, the compounds having the structures:

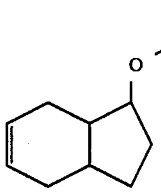
and
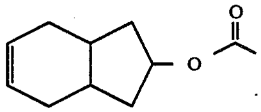

Figure 29:
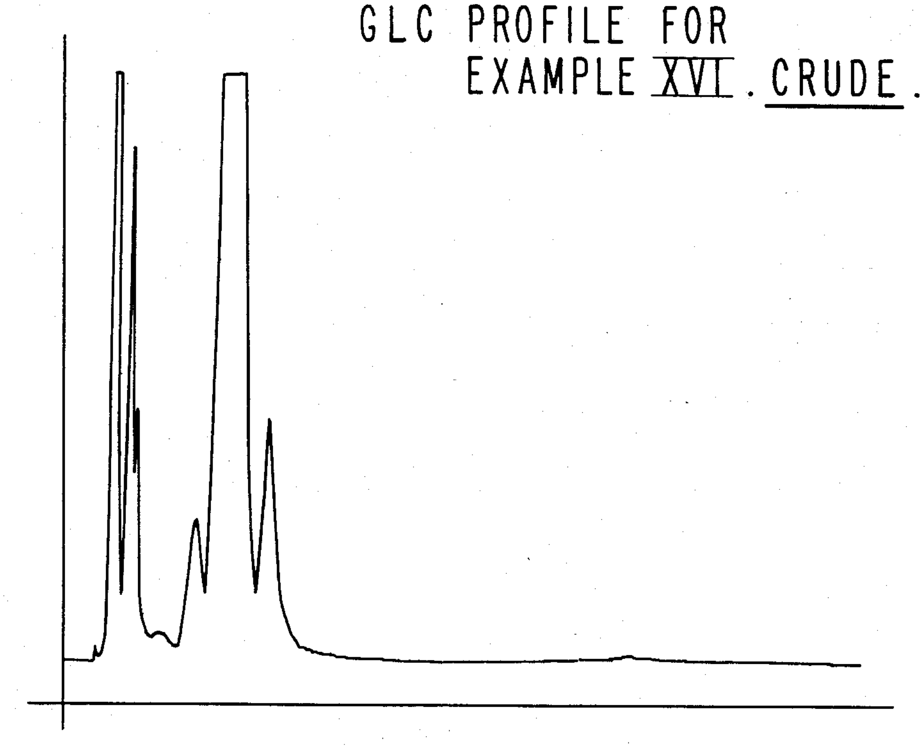

FIG. 29 is the GLC profile for the crude reaction product of Example XVI containing, primarily, the compounds having the structures:

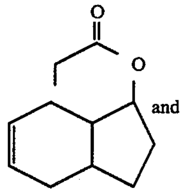
and
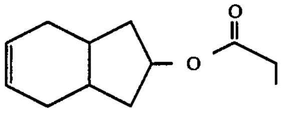

(Conditions: 6'×0.25" 10% SE-30 column programmed at 220° C. isothermal).

Figure 30:
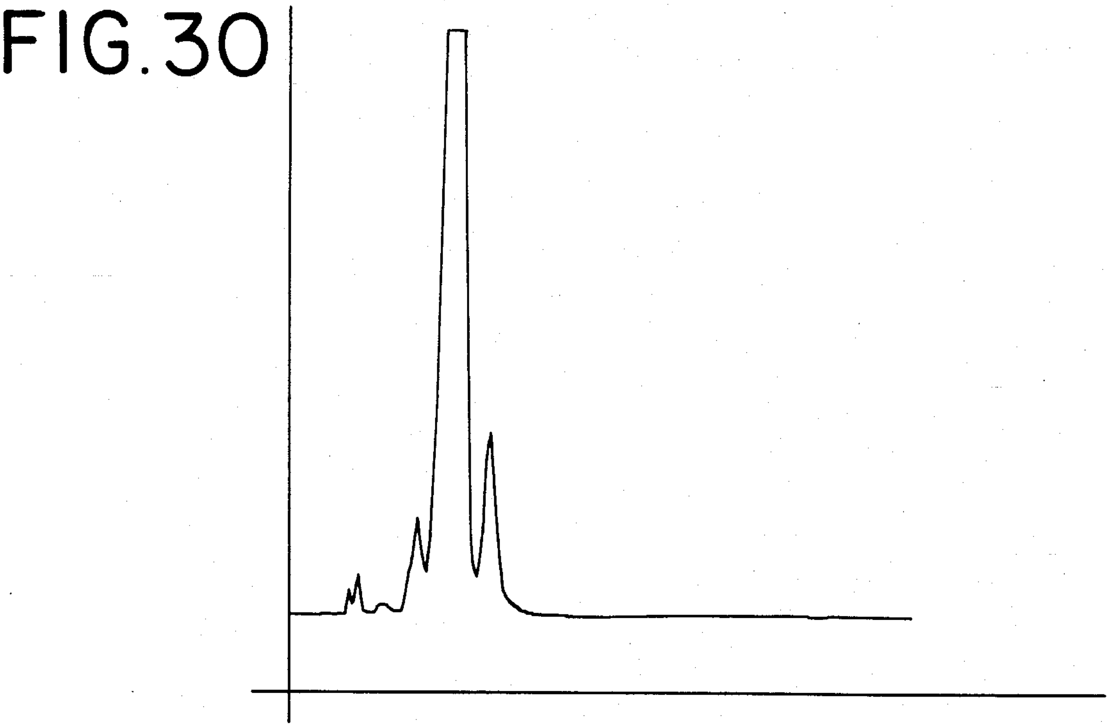

FIG. 30 is the GLC profile for bulked distillation fraction 3-7 of the first distillation of the reaction product of Example XVI containing, primarily, the compounds having the structures:

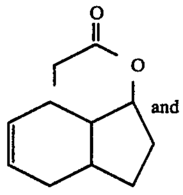
and
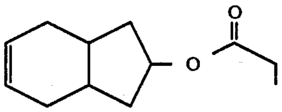

(Conditions: 6'×0.25" 10% SE-30 column programmed at 220° C. isothermal).

Figure 31:
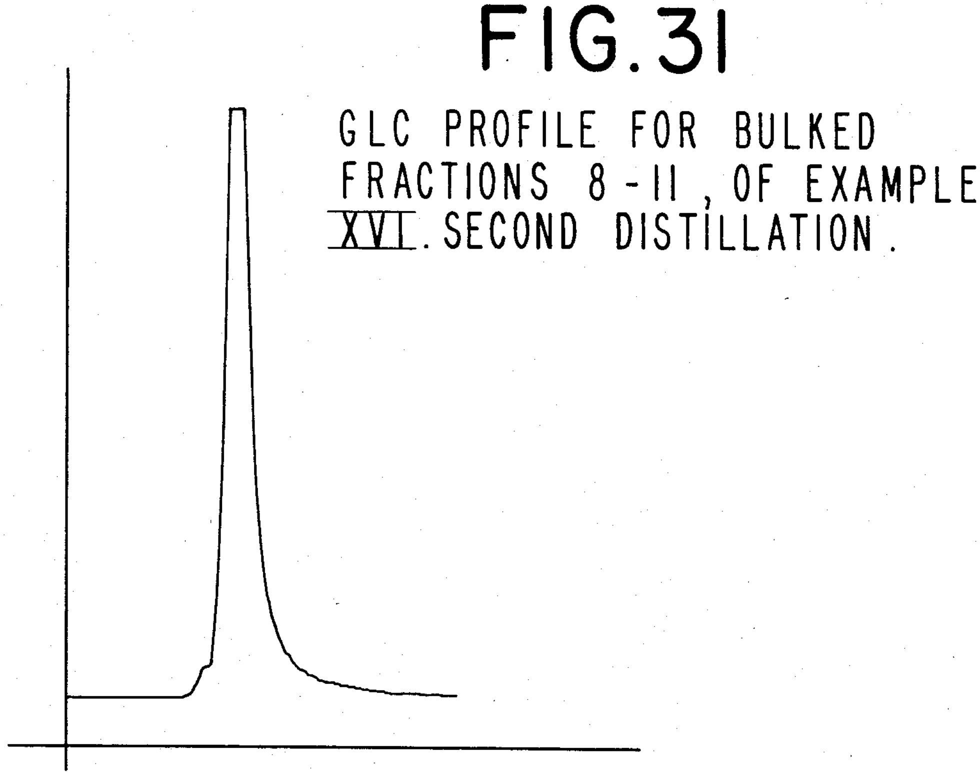

FIG. 31 is the GLC profile for bulked fractions 8-11 of the second distillation of the reaction product of Example XVI containing, primarily, the compounds having the structures:

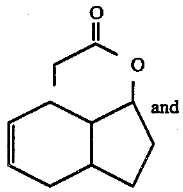
and
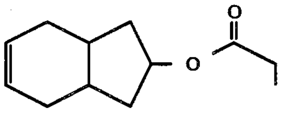

(Conditions: 6'×0.25" 10% SE-30 column programmed at 220° C. isothermal).

Figure 32:
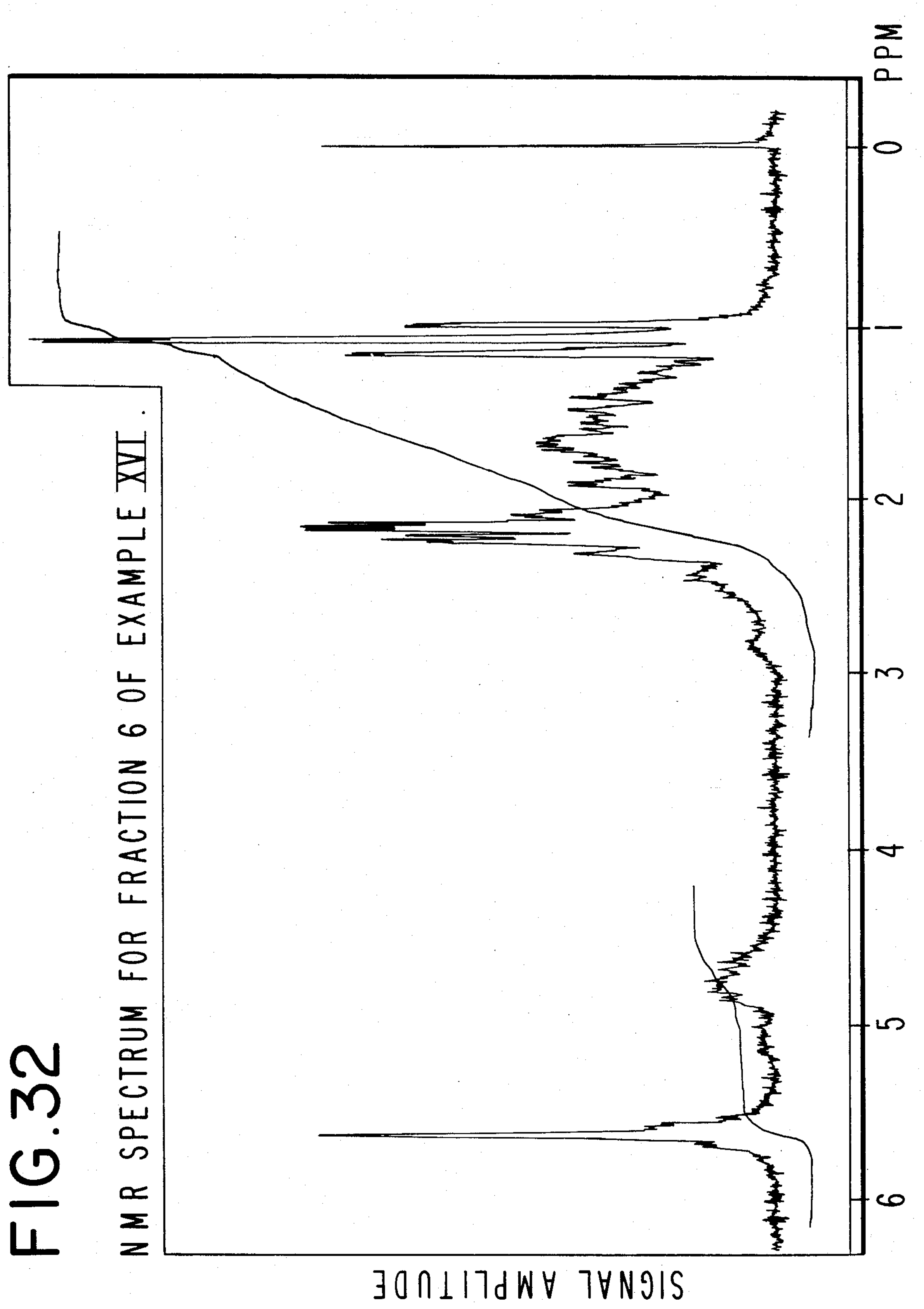

FIG. 32 is the NMR spectrum for fraction 6 of the second distillation of the reaction product of Example XVI containing, primarily, the compounds having the structures:

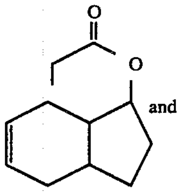
and
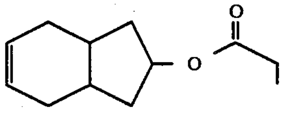

(Conditions: Field strength: 100 MHz; Solvent: $CFCl_3$).

Figure 33:
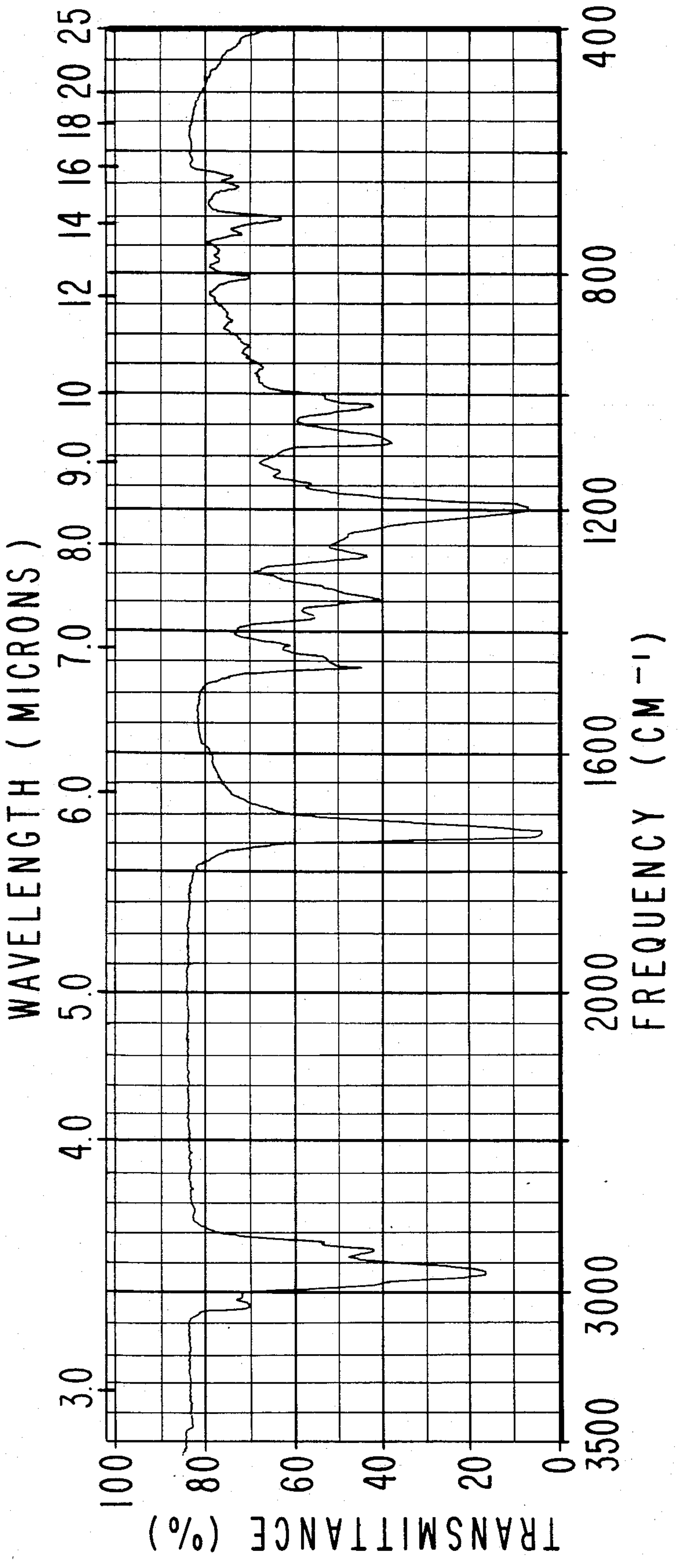

FIG. 33 is the infra-red spectrum for fraction 6 of the second distillation of the reaction product of Example XVI containing, primarily, the compounds having the structures:

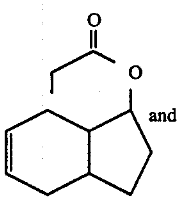
and
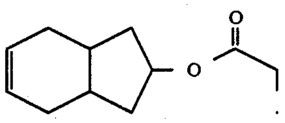

Figure 34:
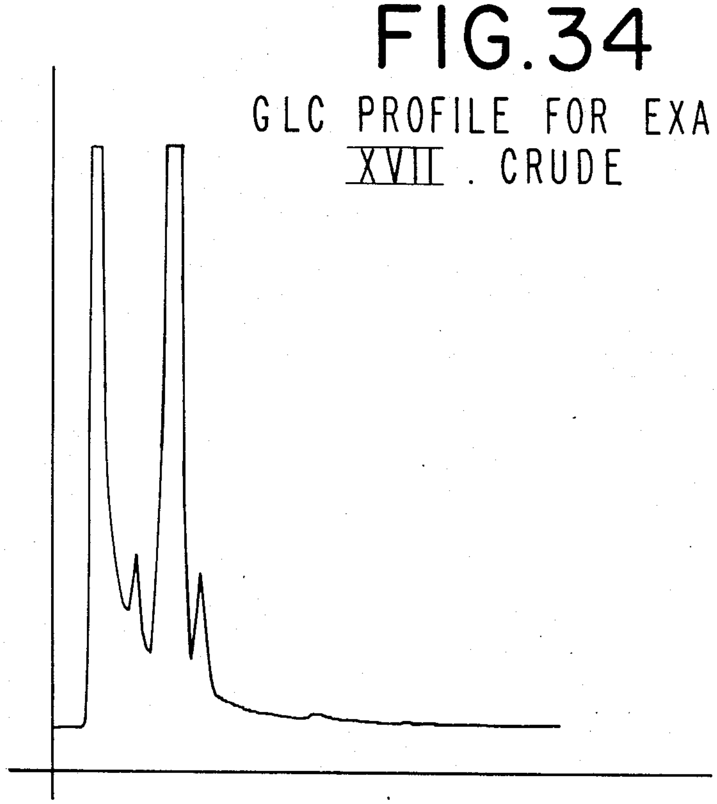

FIG. 34 is the GLC profile for the crude reaction product of Example XVII containing, primarily, the compounds having the structures:

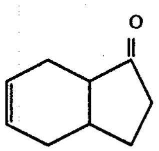
and
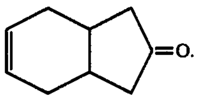

Figure 35:
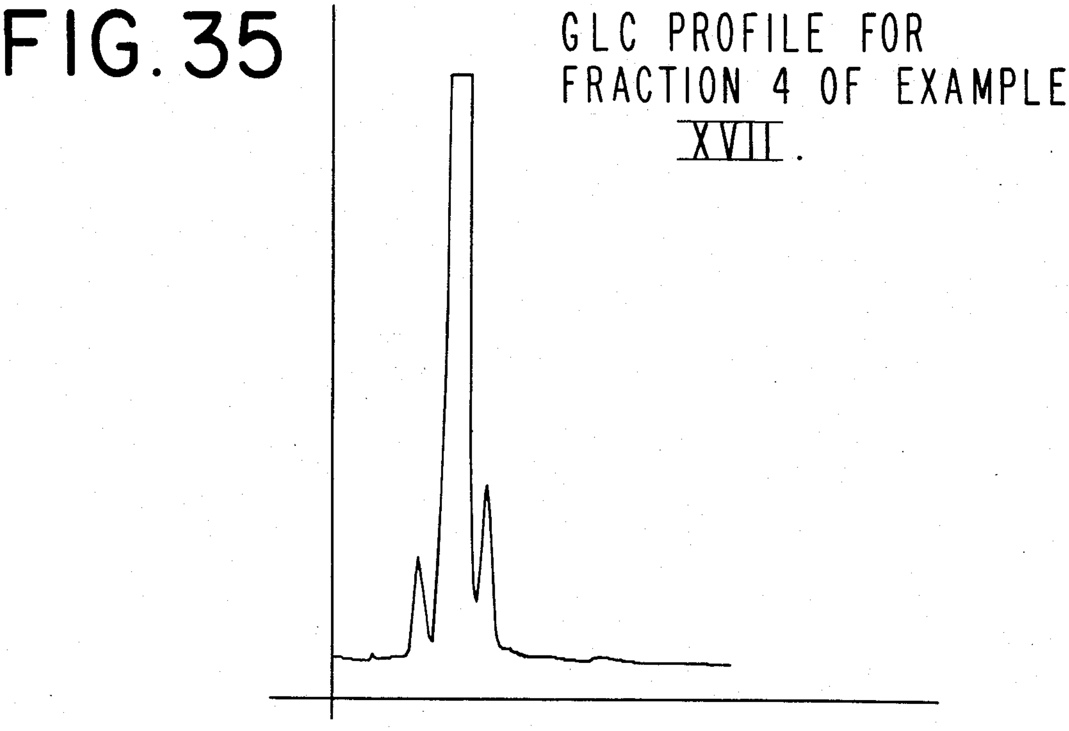

FIG. 35 is the GLC profile for fraction 4 of the distillation product of the reaction product of Example XVII containing, primarily, the compounds having the structures:

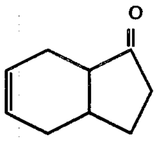
and
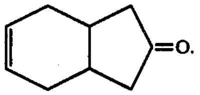

Figure 36:
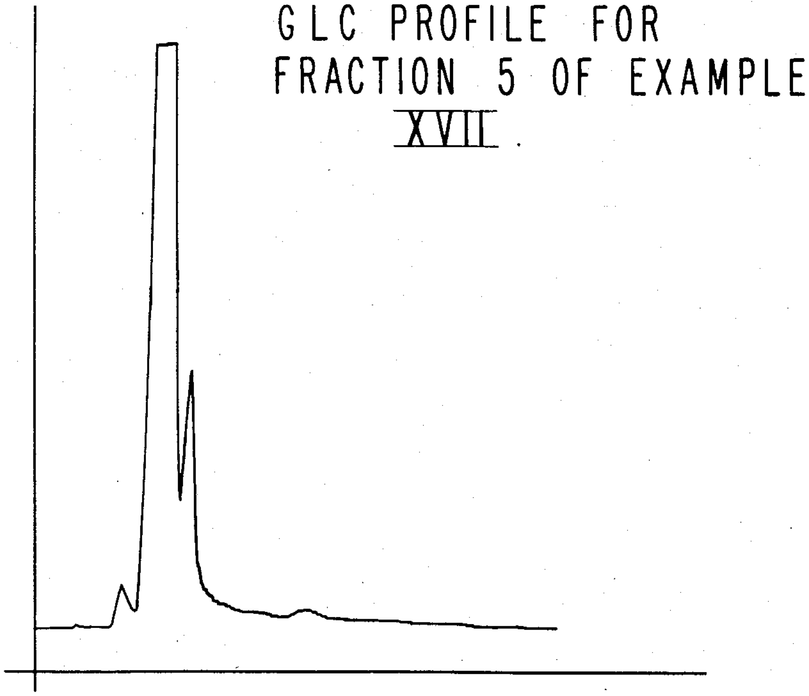

FIG. 36 is the GLC profile for fraction 5 of the distillation product of the reaction product of Example XVII containing, primarily, the compounds having the structures:

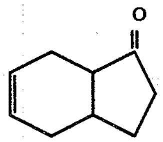
and
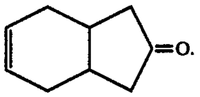

DETAILED DESCRIPTION OF THE DRAWINGS

FIG. 1 is the GLC profile for the crude reaction product of Example I (Conditions: 6'×0.25" 10% SE-30 column programmed at 220° C. isothermal). The peak indicated by reference numeral 10 is the peak for the compounds having the structures:

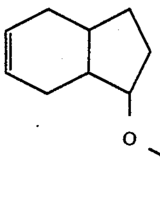

and

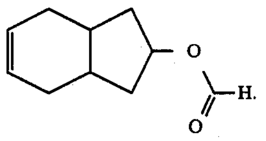

The peak indicated by reference numeral 11 is the peak for the compounds having the structures:

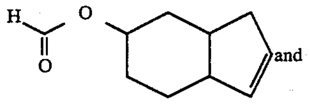

and

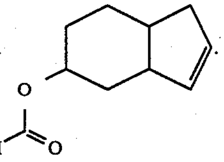

The peak indicated by reference numeral 12 is the peak for the mixture of compounds having the structure:

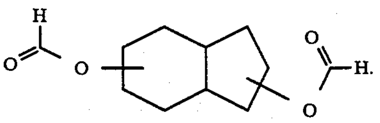

FIG. 2 is the GLC profile for bulked distillation Fractions 4–7 of the reaction product of Example I (Conditions: 6'×0.25" 10% SE-30 column programmed at 220° C. isothermal).

The peak indicated by reference numeral 20 is the peak for the compounds having the structures:

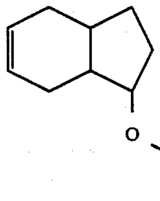

and

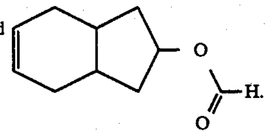

The peak indicated by reference numeral 21 is the peak for the compounds having the structures:

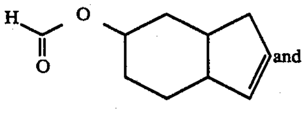

and

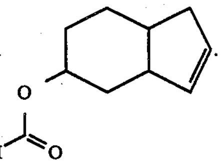

FIG. 9 is the GLC profile of the crude reaction product of Example II. The peak indicated by reference numeral 91 is the peak for the compounds having the structures:

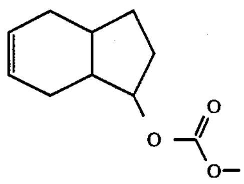

and

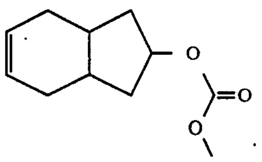

The peak indicated by reference numeral 92 is the peak for the compounds having the structures:

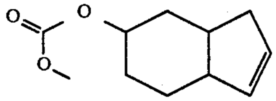

and

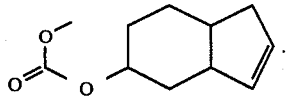

Referring to the drawings in FIGS. 15 and 16, the invention embodied therein comprises a device for forming scented polymer pellets (e.g., polyethylene, polypropylene or mixtures such as polyepsiloncaprolactone and polyethylene or polypropylene or copolymers of polyvinyl acetate and polyethylene or the like) which comprises a vat or container 210 into which a polymer or mixture of polymers admixed with one of the oxobicyclononane derivatives of our invention is placed.

The container is closed by an air-tight lid 228 clamped to the container by clamps 265. A stirrer 273 traverses the lid or cover 228 in air-tight manner and is rotated in a suitble manner. The surrounding cylinder 212 having heating coils which are supplied with electrical current through cable 214 from a rheostat or control 216 is operated to maintain the temperature inside the container 210 such that the polymer such as polyethylene in the container will be maintained at a molten or liquid state. It has been found advantageous to employ a colorless, odorless polymer such as low density polyethylene with a viscosity ranging between about 180 and about 220 centistokes and having a melting point in the neighborhood of 220° F. The heater 212 is operated to maintain the upper portion of the container 210 within the temperature range of from 250°–350° F. An additional bottom heater 218 is regulated through a control 220 connected thereto through a connecting wire 222 to maintain the lower portion of the container 210 within the temperature range of from 250°–350° F.

In accordance with this aspect of the invention, a polymer such as polyethylene or polypropylene is added to the container 210 and is then heated from 10 to 12 hours whereafter an aroma imparting material containing at least one of the oxobicyclononane derivatives of our invention or at least one of the oxobicyclononane derivatives of our invention per se is quickly added to the melt. The mixture containing the oxobicyclononane derivative of our invention must be compatible with the polymer and forms a homogeneous liquid melt therewith. The heat resisting mixture generally containing from 10 to 40% by weight of the mixture of at least one of the oxobicyclononane derivatives of our invention or a mixture thereof is added to container 210; the mixture is stirred for a few minutes, for example, 5–15 minutes, and maintained within the temperature range as indicated previously by the heating coils 212 and 218 respectively. The controls 216 and 220 are connected through cables 224 and 226 through a suitable supply of electric current for supplying the power for heating purposes.

Thereafter, the valve "V" is opened permitting the mass to flow outwardly through a conduit 232 having a multiplicity of orifices 234 adjacent the lower side thereof. The outer end of the conduit 232 is closed so that the liquid polymer and at least one of the oxobicyclononane derivatives of our invention or mixture containing same will continuously drop or drip through the orifices 234 downwardly from the conduit 232. During this time, the temperature of the polymer and the perfumant mixture containing at least one of the oxobicyclononane derivatives of our invention in the container 210 is accurately controlled so that a temperature in the range of from 210° up to 275° F. will be maintained in the material exiting in the conduit 232. The regulation of the temperature through the control 216 and the control 220 is essential in order to insure temperature balance to provide for the continuous dropping or dripping of the molten polymer and the perfumant containing at least one of the oxobicyclononane derivatives of our invention through the orifices 234 at a range which will insure the formation of droplets 236 which will fall downwardly onto a moving conveyor belt 238 trained to run between conveyor wheels 240 and 242 beneath the conduit 232. When the droplets 236 fall onto the conveyor belt 238 they form pellets 244 which harden almost instantaneously and fall off the end of the conveyor 238 into a container 246 which is advantageously filled with water or some other suitable liquid to insure the rapid cooling of each of the pellets. The pellets are then collected from the container 246 and packaged for shipment.

A feature of the invention is the provision for the moistening of the conveyor belt 238 to insure the rapid formation of the solid polymer-aromatizing agent containing pellets 244 without sticking to the belt. The belt 238 is advantageously of a material which will not normally stick to a melted polymer, but the moistening means 248 insures a sufficiently cold temperature of the belt surface for the adequate formation of the pellets 244. The moistening means comprises a container 250 which is continuously fed with water 252 to maintain a level 254 for moistening a sponge element 256 which bears against the exterior surface of the belt 238.

THE INVENTION

The present invention provides oxobicyclononane derivatives defined according to the strucure:

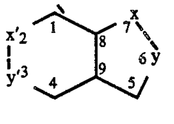

wherein X, Y, X' and Y' each represents the moiety having one of the structures:

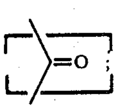 ; 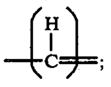 ; 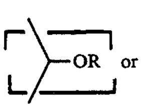 or 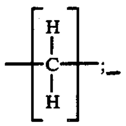 ;

wherein one of the dashed lines represents a carbon-carbon single bond and the other of the dashed lines represents a carbon-carbon double bond with the proviso that when X' and Y' are each the moiety:

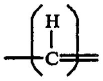

then the dashed line at the "2–3" position is a carbon-carbon double bond and the dashed line at the "6–7" position is a carbon-carbon single bond and one of X or Y has the structure:

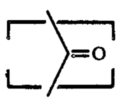 or 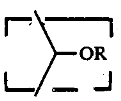

and the other of X or Y has the structure:

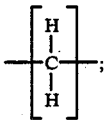 ;

and with the further proviso that when X and Y are the moieties:

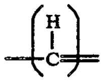

then the dashed line at the "6–7" position is a carbon-carbon double bond and the dashed line at the "2–3" position is a carbon-carbon single bond and one of X' or Y' has the structure:

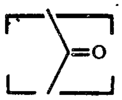 or 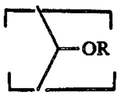

and the other of X' or Y' has the structure:

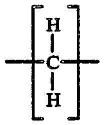

and wherein R represents hydrogen, $C_1$–$C_3$ acyl or $C_1$–$C_2$ alkoxy carbonyl; primarily including mixtures containing the compounds defined according to the structure:

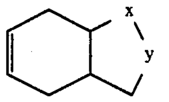

wherein one of X or Y is the moiety:

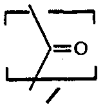 or 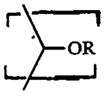

and the other of X or Y is the moiety:

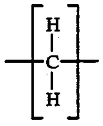

with R being one of hydrogen, $C_1$–$C_3$ acyl or $C_1$–$C_2$ alkoxy carbonyl. Included in the foregoing genus having the structure:

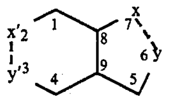

is the genus of compounds having the structure:

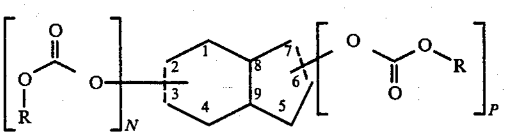

wherein R represents methyl or ethyl; one of the dashed lines represents a carbon-carbon single bond or a carbon-carbon double bond; N and P each represents 0 or 1; the sum of N and P being equal to 1; with the proviso that when N is 1, the dashed line at the "2–3" position is a carbon-carbon single bond and the dashed line at the "6–7" position is a carbon-carbon double bond; including the sub-genus defined according to the structure;

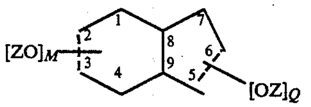

wherein Z represents $C_1$–$C_2$ alkoxy carbonyl; $C_1$–$C_3$ acyl; or hydrogen; wherein one of the dashed lines represents a carbon-carbon double bond and the other of the dashed lines represents a carbon-carbon single bond; wherein M and Q each represents 0 or 1 with the proviso that the sum of M+Q is 1; and with the further proviso that M is 1 when the dashed line at the "2–3" position is a carbon-carbon single bond and the dashed line at the "5–6" position is a carbon-carbon bould bond and Q is 1 when the dashed line at the "5–6" position is a carbon-carbon single bond and the dashed line at the "2–3" position is a carbon-carbon double bond further including the genuses having the structures:

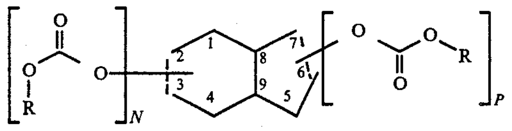

and

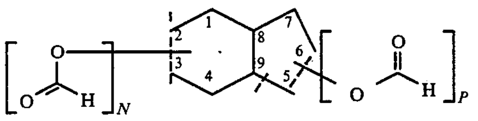

wherein R represents methyl or ethyl; N and P each represents 0 or 1; each of the dashed lines represents a carbon-carbon single bond or a carbon-carbon double bond with the provisos:

(i) the sum of N+P=1;

(ii) when N is 1 the dashed line at the "2–3" position is a carbon-carbon single bond and the dashed line at the "6–7" position is a carbon-carbon double bond and when P is 1 the dashed line at the "6–7" position is a carbon-carbon single bond and the dashed line at the "2–3" position is a carbon-carbon double bond.

The compounds and mixtures of compounds covered by the genus having the structure:

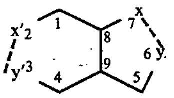

wherein X, Y, X′ and Y′ each represents the moiety having one of the structures:

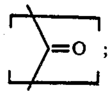 ; 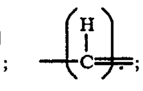 ; 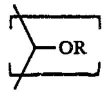 or 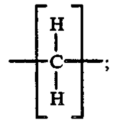 ;

wherein one of the dashed lines represents a carbon-carbon single bond and the other of the dashed lines represents a carbon-carbon double bond with the proviso that when X′ and Y′ are each the moiety:

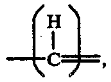, the dashed line at the "2–3" position is a carbon-carbon double bond and the dashed line at the "6–7" position is a carbon-carbon single bond and one of X or Y has the structure:

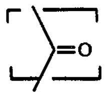 or 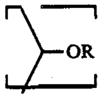

and the other of X or Y has the structure:

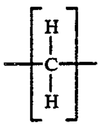

and with the further proviso that when X and Y are the moieties:

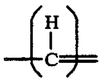

then the dashed line at the "6–7" position is a carbon-carbon double bond and the dashed line at the "2–3" position is a carbon-carbon single bond and one of X′ or Y′ has the structure:

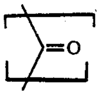 or 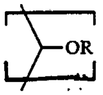

and the other of X′ or Y′ has the structure:

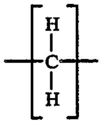

and wherein R represents hydrogen, $C_1$–$C_3$ acyl or $C_1$–$C_2$ alkoxy carbonyl; mixtures containing the compounds defined according to the generic structure:

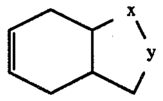

wherein one of X or Y is the moiety;

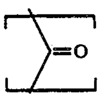 or 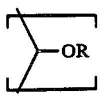

and the other of X or Y is the moiety;

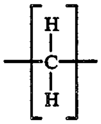

with R being one of hydrogen; $C_1$–$C_3$ acyl or $C_1$–$C_2$ alkoxy carbonyl. Included in the foregoing genus having the structure:

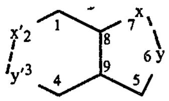

is the genus of compounds having the structure:

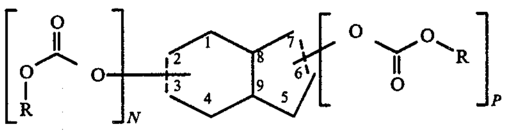

wherein R represents methyl or ethyl; one of the dashed lines represents a carbon-carbon single bond or a carbon-carbon double bond; N and P each represents 0 or 1; the sum of N and P being equal to 1; with the proviso that when N is 1, the dashed line at the "2–3" position is a carbon-carbon single bond and the dashed line at the "6–7" position is a carbon-carbon double bond including the genus having the structure:

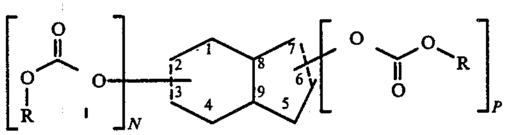

(carbonates) have utilities in perfumery; that is, in augmenting or enhancing the aroma of perfume compositions, colognes and perfumed articles including solid or liquid anionic, cationic, nonionic or zwitterionic detergents, fabric softener compositions, fabric softener articles, cosmetic compositions, hair preparations and perfumed polymers. The compounds covered by the genus having the structure:

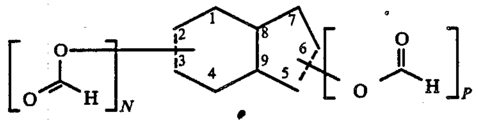

are also useful as intermediates or precursors in forming the genus having the structure:

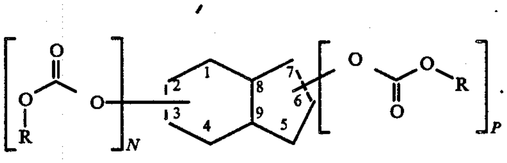

The oxobicyclononane derivatives of our invention defined according to the genus:

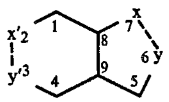

wherein X, Y, X′ and Y′ each represents the moiety having one of the structures:

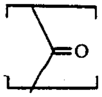 ; 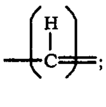 ; 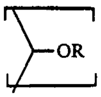 or 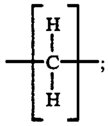 ;

wherein one of the dashed lines represents a carbon-carbon single bond and the other of the dashed lines represents a carbon-carbon double bond with the proviso that when X′ and Y′ are each the moiety;

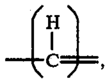 , then the dashed line at the "2–3" position is a carbon-carbon double bond and the dashed line at the "6–7" position is a carbon-carbon single bond and one of X or Y has the structure:

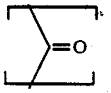 or 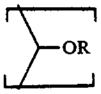

and the other of X or Y has the structure:

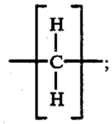 ;

and with the further proviso that when X and Y are the moieties:

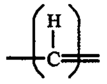

then the dashed line at the "6–7" position is a carbon-carbon double bond and the dashed line at the "2–3" position is a carbon-carbon single bond and one of X′ or Y′ has the structure:

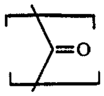 or 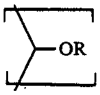

and the other of X′ or Y′ has the structure:

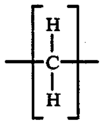

and wherein R represents hydrogen, $C_1$–$C_3$ acyl or $C_1$–$C_2$ alkoxy carbonyl having the following perfume utilities:

TABLE I

| Structure of Compounds | Perfumery Utilities |
|---|---|
| Mixture of compounds defined according to the generic structure: 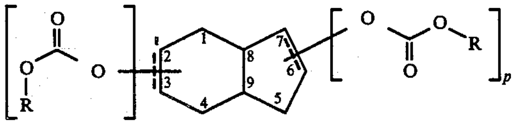 wherein R represents methyl produced according to Example II bulked fractions 8–17 of second distillation. | A strawberry aroma with green banana topnotes. |
| Mixture of compounds defined according to the generic structure: 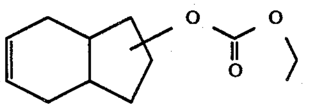 bulked fractions 6 and 7 produced according to Example XIII. | A rosey, strawberry, banana aroma with floral and fruity topnotes. |
| Mixture of compounds defined according to the generic structure: | A woody, piney, minty aroma with spicy topnotes. |

TABLE I-continued

| Structure of Compounds | Perfumery Utilities |
|---|---|
| 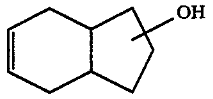 produced according to Example XIV, bulked distillation fractions 4-6. | |
| Mixture of compounds defined according to the generic structure: 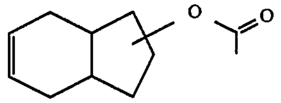 prepared according to Example XV, bulked distillation fractions 7-10. | A fruity, jasmine and minty aroma. |
| Mixture of compounds defined according to the generic structure: 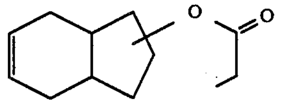 prepared according to Example XVI, bulked distillation fractions 8-11. | A banana aroma with fruity, floral, hawthorne, ozoney and anisic topnotes. |
| Mixture of compounds defined according to the generic structure: 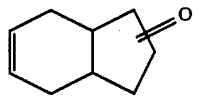 produced according to Example XVII, bulked distillation fractions 4 and 5. | A woody aroma with fruity topnotes. |

The present invention also provides an economically efficient process for synthesizing the compounds defined according to the structure:

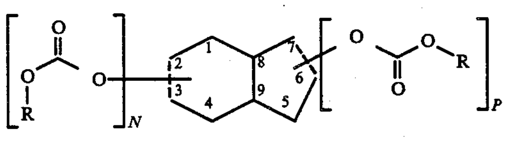

by first reacting bicyclononadiene having the structure:

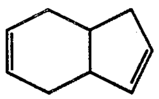

with formic acid according to the reaction:

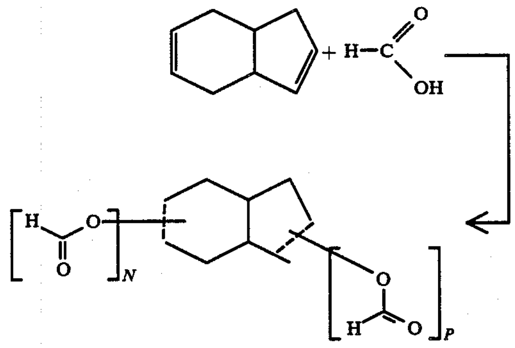

and then reacting the resulting formate compound with the carbonate having the structure:

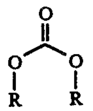

(wherein R represents methyl or ethyl) according to the reaction:

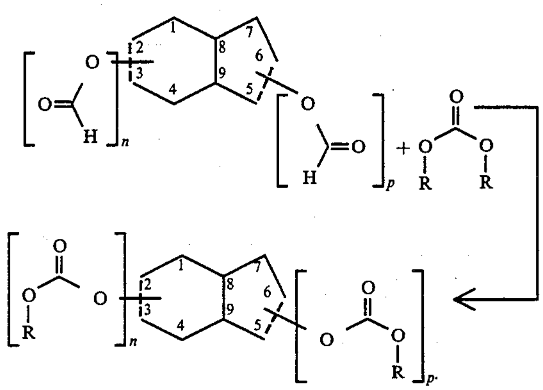

The bicyclononene formate is formed from bicyclononadiene by reaction of bicyclononadiene with formic acid. The reaction is carried out at reflux conditions for a period sufficient to yield a product containing greater than 80% bicyclononene formate. The mole ratio of formic acid:bicyclononadiene may vary between about 2:1 up to about 7:1 with a preferred mole ratio of between 5.5:1 and 6:1 of formic acid:bicyclononadiene. At the end of the reaction the reaction product, the bicyclononene formate is distilled. The crude reaction product contains the compounds having the structures:

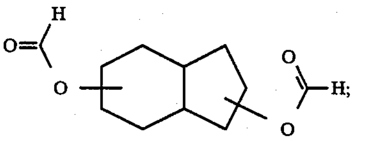

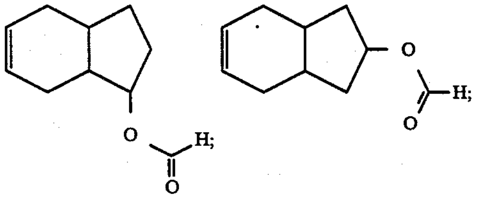

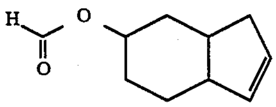

; and

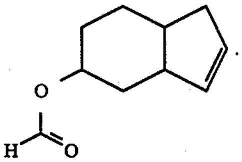

with the majority of the mixture being the compounds having the structures:

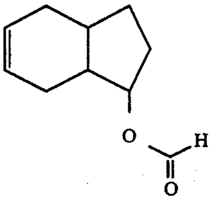

and

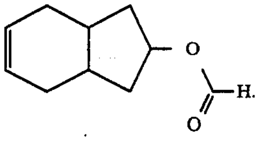

The compound having the structure:

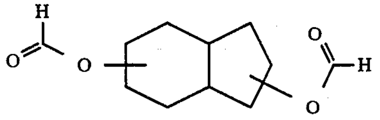

is separated out from the reaction mass by fractional distillation leaving the compounds having the structures:

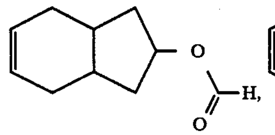

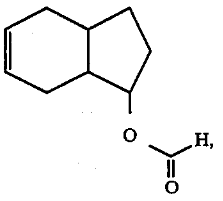

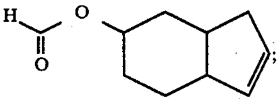

; and

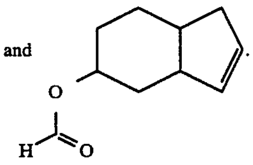

These compounds may be separated from one another whereby the group of compounds having the structures:

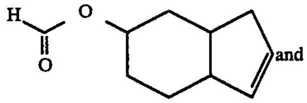

and

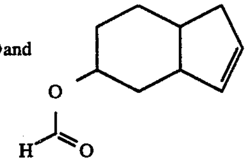

may be separated from the group of compounds having the structures:

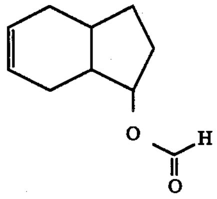

and

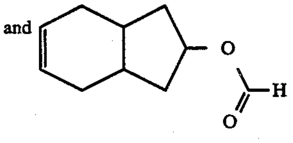

by preparative liquid chromatography. However, from a practical standpoint the fractional distillation product is sufficient for the purposes of use of the resulting bicyclononenyl formates as intermediates in preparing carbonates which are subsequently useful in perfumery.

The resulting mixture of compounds having the structures:

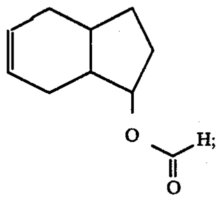 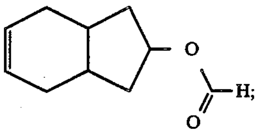

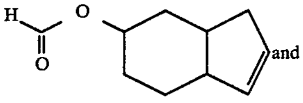 and 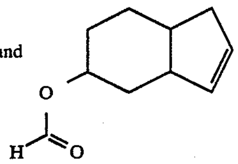

is then reacted with either diethyl carbonate or dimethyl carbonate defined according to the structure:

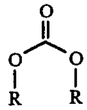

wherein R represents methyl or ethyl in the presence of an alkali metal alkoxide catalyst such as sodium methoxide, sodium ethoxide, sodium isopropoxide, potassium t-butoxide as well as other metal alkoxides such as aluminum isopropoxide. The reaction temperature may vary between 50° C. and 90° C. with a preferred reaction temperature of between 60° and 80° C.

The mole ratio of dialkyl carbonate to bicyclononenyl formate may vary from about 2:1 up to about 4:1 with a preferred mole ratio of about 2.8:1. The concentration of alkali metal alkoxide or other metal alkoxide in the reaction mass may vary from about 0.03 moles per liter up to about 0.5 moles per liter with a preferred concentration of alkali metal alkoxide or other metal alkoxide in the reaction mass being about 0.05 moles per liter. At the end of the reaction the reaction mass is quenched with weak acid such as acetic acid. The reaction mass is then fractionally distilled thereby recovering a mixture of carbonates having the structures:

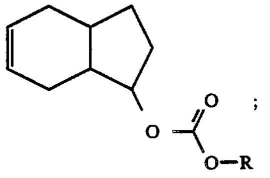

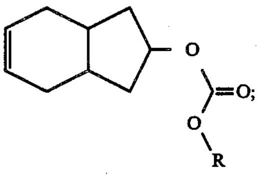

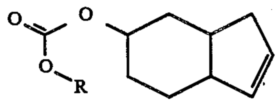 and

-continued

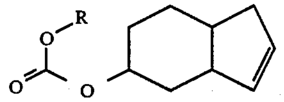

with the major (e.g., greater than 75%) portion of carbonates having the structures:

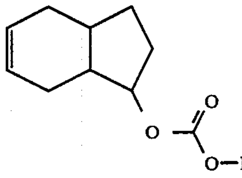 and 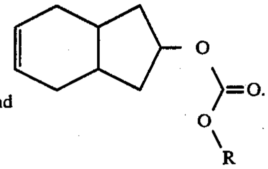

The group of carbonates having the structures:

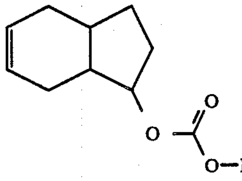 and 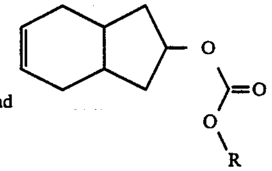

may be separated by preparative liquid chromatograph from the group of carbonates having the structures:

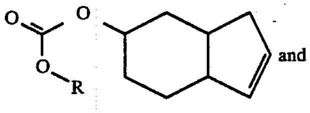 and

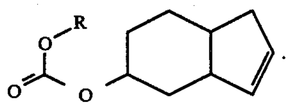

However from a practical standpoint it is preferable not to so separate the fractional distillation products but to use such fractional distillation products "as is" for their organoleptic properties in perfumery, e.g., augmenting or enhancing the aroma of perfume compositions, perfumed articles and colognes.

The bicyclononenyl formates defined according to the structure:

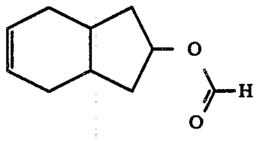 or 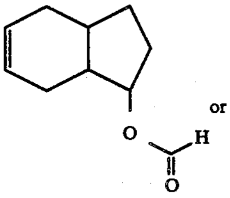 or

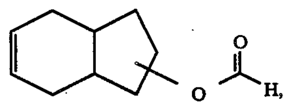

usually mixtures of bicyclononenyl formates having the structure:

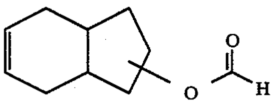

may also be utilized to prepare other compositions of matter of our invention, particularly the compounds having the structures:

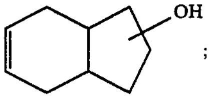
;
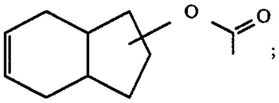
;
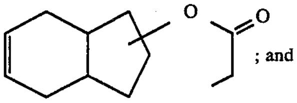
; and
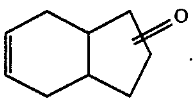
.

In those cases there the compounds having the structures:

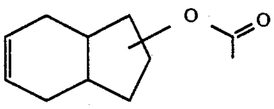
;
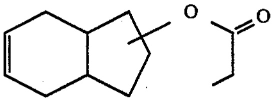
; and
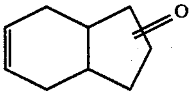

are to be prepared, these materials are prepared using as a starting material the compounds having the structure:

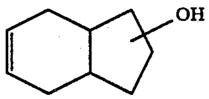

which, in turn, is prepared by hydrolyzing the compounds having the structure:

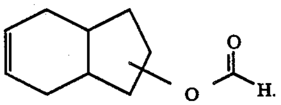

The hydrolysis reaction on the compound or compounds having the structure:

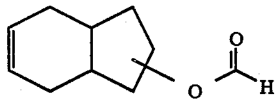

is as follows:

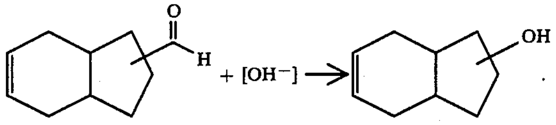

The reaction is carried out in a strong base such as sodium hydroxide or potassium hydroxide with a mole ratio of hydroxyl ion:formate being between about 2:1 and about 1:1 with a preferred mole ratio of hydroxyl ion:formate being about 1.5:1. The reaction temperature may vary between about 40° and 60° C. with a preferred reaction temperature of about 50° C. At the end of the reaction, the reaction mass is neutralized and the resulting product is preferably fractionally distilled from the reaction mass. The resulting compounds may be used "as is", or they may be separated by means of column chromatography or they may be further reacted as shown, infra.

Compounds having the structure:

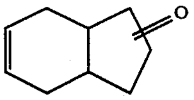

may be prepared according to the reaction:

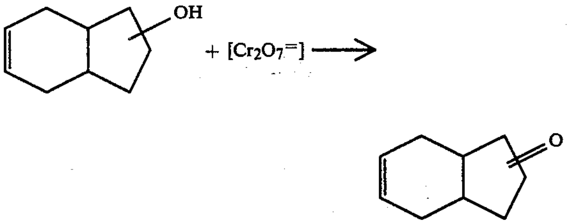

whereby the compounds having the structure:

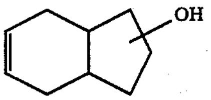

are reacted with an excess of oxidizing agent such as potassium dichromate in sulfuric acid, in the presence of an inert solvent such as isopropyl alcohol. The mole ratio of compounds having the structure:

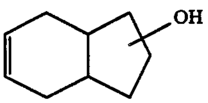

to dichromate oxidizing agent may vary from about 1:1 up to about 1:1.5 with, preferably, a slight excess of dichromate ion being present. The reaction is carried out at a temperaure of between about 30° and about 40° C. At the end of the reaction, the reaction mass is extracted with a solvent such a toluene and the organic extracts are neutralized using aqueous base. The reaction mass is then fractionally distilled to yield the compounds having the structure:

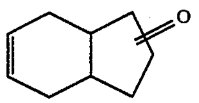

which may be used "as is" or separated prior to use by means of column chromatography.

Furthermore, the compounds having the structure:

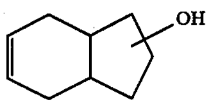

may be esterified as with acetic anhydride or propionic anhydride to form the corresponding acetic acid esters or propionic acid esters according to the reactions:

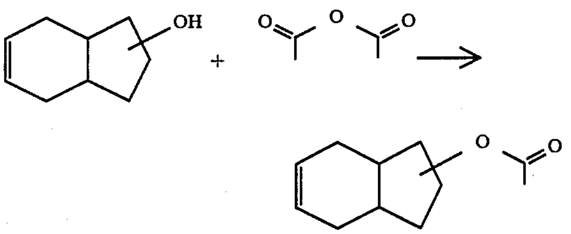

and

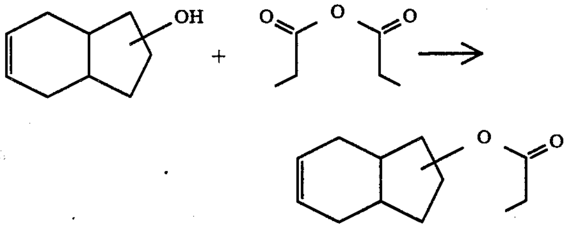

The reaction is carried out using a slight molar excess of alkanoic anhydride, e.g., acetic anhydride or propionic anhydride, e.g., about a 15% excess. The reaction is carried out at a temperature in the range of from about 115° C. up to about 140° C. At the end of the reaction, the reaction mass is quenched with water and the organic phase is separated and neutralized with weak base such as sodium bicarbonate. The reaction mass is then fractionally distilled yielding the compounds having the structures:

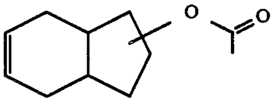

(in the case of using an acetic anhydride starting material)

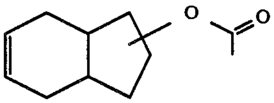

(in the case of using a propionic acid anhydride starting material).

The resulting mixtures can be used "as is" or they can be separated into their component isomers as by means of column chromatography.

As stated, supra, the oxobicyclononane derivatives of our invention can be used to contribute strawberry, rosey, banana, woody, piney, minty, fruity and jasmine aromas with floral, fruity, spicy, green, hawthorne, ozoney and anisic topnotes to perfume compositions, performed articles and colognes with the perfumed articles being such materials as solid or liquid anionic, cationic, nonionic or zwitterionic detergents, perfumed polymers, fabric softener compositions, fabric softener articles, optical brighteners, fabric conditions, hair preparations, shampoos and hair sprays. As olfactory agents the oxobicyclononane derivatives of our invention can be formulated into or used as components of a "perfume composition".

The term "perfume composition" is used herein to mean a mixture of organic compounds including, for example, alcohols other than the alcohols of our invention, aldehydes, ketones other than the ketones of our invention, nitriles, ethers, lactones, esters other than the carbonates and alkanoic acid esters of our invention and, frequently, hydrocarbons which are admixed so that the combined odors of the individual components produce a pleasant or desired fragrance. Such perfume compositions usually contain: (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) top notes which are usually low-boiling, fresh-smelling materials.

In perfume compositions, the individual component will contribute its particular olfactory characteristics, but the overall effect of the perfume composition will be the sum of each of the effects of each of the ingredients. Thus, the individual compounds of this invention or mixtures thereof can be used to alter the aroma characteristics of the perfume composition, for example, by highlighting or moderating the olfactory reaction contributed by another ingredient in the composition.

The amount of oxobicyclononane derivative(s) of our invention which will be effective in perfume compositions depends upon many factors including the other ingredients, their amounts and the effects which are desired. It has been found that perfume compositions containing as little as 0.1% of the oxobicyclononane derivative(s) of our invention or even less and perfume compositions containing as much as 70% of one or more of the oxobicyclononane derivative(s) of our invention cañ be used to impart interesting, strawberry, rosey, banana, woody, piney, minty, fruity and jasmine aromas with floral, fruity, spicy, green, hawthorne, ozoney and anisic topnotes to perfumed articles, perfume compositions and colognes. Such perfumed articles include fabric softener compositions, drier-added fabric softener articles, cosmetic powders, talcs, solid or liquid anionic, cationic, nonionic or zwitterionic detergents and perfumed polymers. The amount employed can range up to 70% as stated, supra, and will depend on considerations of cost, nature of the end product and the effect desired on the finished product and particular fragrance sought.

Thus, one or more of the oxobicyclononane derivative(s) of our invention can be used alone or in a perfume composition as an olfactory component, in solid or liquid anionic, cationic, nonionic or zwitterionic detergents (including hand soaps) perfumed polymers (those which are microporous and those which are macroporous and contain particulate absorbent fillers such as talc), space odorants and deodorants; perfumes, colognes, toilet waters, bath salts, hair preparations such as lacquers, brilliantines, pomades and shampoos; cosmetic preparations such as creams, deodorants, hand lotions and sun screens; powders such as talcs, dusting powders, face powders and the like.

When used as an olfactory component of a perfumed article such as a microporous polymer or a macroporous polymer containing an absorbent filler or such as a solid or liquid cationic, anionic, nonionic or zwitterionic detergent or of a cosmetic powder, as little as 0.01% of one or more of the oxobicyclononane derivative(s) of our invention will suffice to provide an interesting strawberry, rosey, banana, woody, piney, minty, fruity and jasmine aromas with floral, fruity, spicy, green, hawthorne, ozoney and anisic topnotes. Generally, no more than 0.8% of one or more of the oxobicyclononane derivative(s) of our invention is required. Thus, the range of oxobicyclononane derivative(s) in perfumed articles may vary from about 0.01% up to about 0.8%.

In addition, the perfume compositions of our invention can contain a vehicle or carrier for the oxobicyclononane derivative(s) of our invention alone or with other ingredients. The vehicle can be a liquid such as an alcohol such as ethanol, a glycol such as propylene glycol or the like. The carrier can be an absorbent solid such as a gum (e.g., xanthan gum or gum arabic) or components for encapsulating the composition as by coacervation using gelatin or by forming a polymeric shell around a liquid perfume center by means of the use of a urea formaldehyde prepolymer.

The following Examples I, II, XIII, XIV, XV, XVI and XVII set forth processes for preparing the oxobicyclononane derivatives of our invention. Examples III–XII and the examples following Example XVII set forth methods for using the oxobicyclononane derivatives of our invention for their organoleptic properties.

Unless otherwise indicated, all parts and percentages are by weight.

EXAMPLE I

PREPARATION OF MIXTURE CONTAINING BICYCLONENYL FORMATE COMPOUNDS

Reaction:

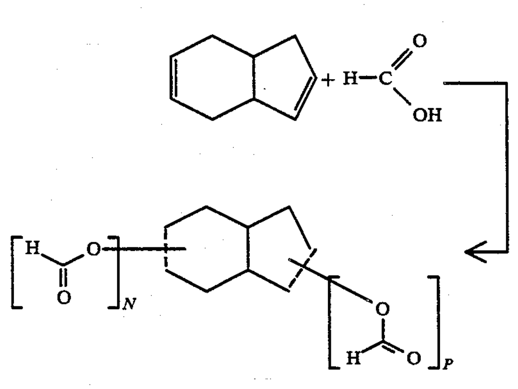

(wherein a mixture is formed containing several compounds and wherein in the mixture N and P each represents 0 or 1 and wherein the dashed lines represent carbon-carbon single bonds or carbon-carbon double bonds with the proviso that when N is 1 and P is 1, both of the dashed lines represent carbon-carbon single bonds).

Into a 500 cc reaction flask equipped with stirrer, thermometer, heating mantle and reflux condenser are placed 120 grams (1 mole) of bicyclononadiene having the structure:

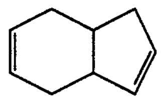

and 261 grams (5.7 moles) of formic acid.

The reaction mass is then refluxed at 100° C. for a period of 9 hours. At the end of the 9 hour period, a 10% sodium chloride solution is added to the reaction mass. The organic phase is separated from the aqueous phase and the organic phase is distilled yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 25/53 | 40/68 | 38/38 | 200 |
| 2 | 60 | 73 | 2.4 | 89 |
| 3 | 70 | 83 | 2.4 | 102 |
| 4 | 74 | 84 | 2.0 | 102 |
| 5 | 76 | 86 | 2.0 | 97 |
| 6 | 86 | 110 | 2.0 | 242 |
| 7 | 86 | 120 | 2.0 | 257 |
| 8 | 120 | 150 | 2.0 | 62 |
| 9 | 150 | 195 | 2.0 | 94 |
| 10 | 173 | 245 | 2.4 | 65 |

The distillation is carried out on a 2" splash column.

FIG. 1 is the GLC profile of the crude reaction product prior to distillation. The peak indicated by reference numeral 10 is the peak for the mixture of compounds having the structures:

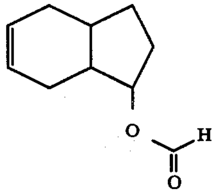

and

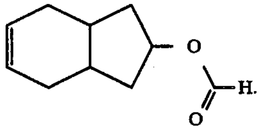

The peak indicated by reference numeral 11 is the peak for the mixture of compounds having the structures:

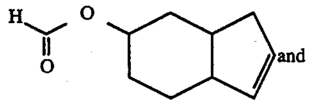

and

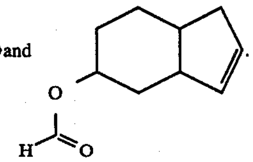

The peak indicated by reference numeral 12 is the peak for the mixture of compounds having the structure:

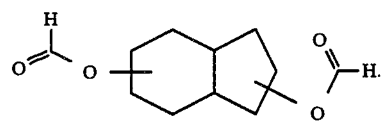

FIG. 2 is the GLC profile for bulked distillation Fractions 4–7 of the foregoing distillation. The peak indicated by reference numeral 20 is the peak for the mixture of compounds having the structures:

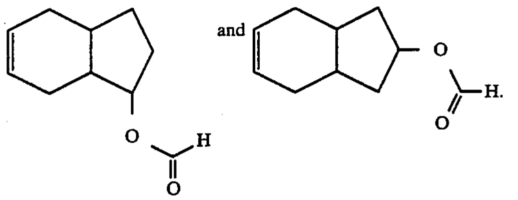

The peak indicated by reference numeral 21 is the peak for the mixture of compounds having the structures:

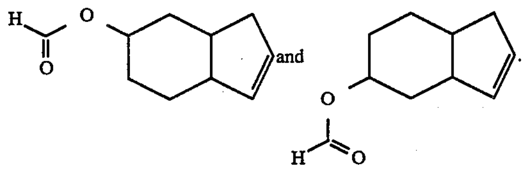

FIG. 3 is the NMR spectrum for the peak indicated by reference numeral 20 of FIG. 2 for the compounds having the structures:

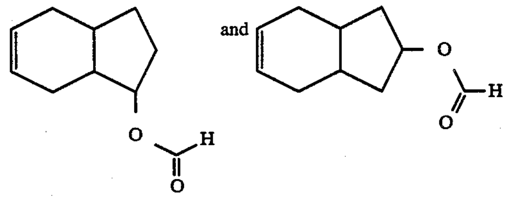

(Conditions: Field strength: 100 MHz; Solvent: $CFCl_3$).

FIG. 4 is the infra-red spectrum for the peak indicated by reference numeral 20 of the GLC profile of FIG. 2 for the compounds having the structures:

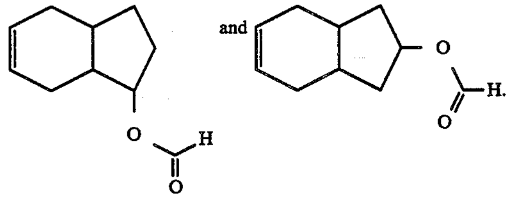

FIG. 5 is the NMR spectrum for the peak indicated by reference numeral 21 of the GLC profile of FIG. 2 for the mixture of compounds having the structures:

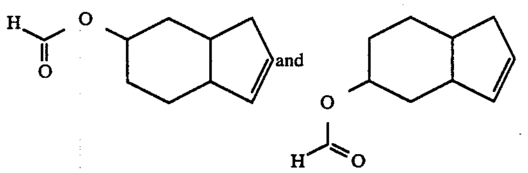

(Conditions: Field strength: 100 MHz; Solvent: $CFCl_3$).

FIG. 6 is the infra-red spectrum for the peak indicated by reference numeral 21 of the GLC profile of FIG. 2 for the mixture of compounds having the structures:

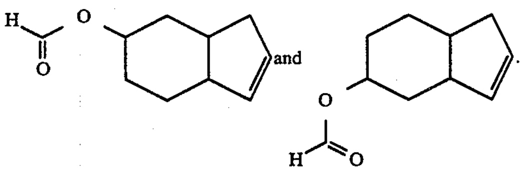

EXAMPLE II

PREPARATION OF BICYCLONONANYL METHYL CARBONATE MIXTURE

Reaction:

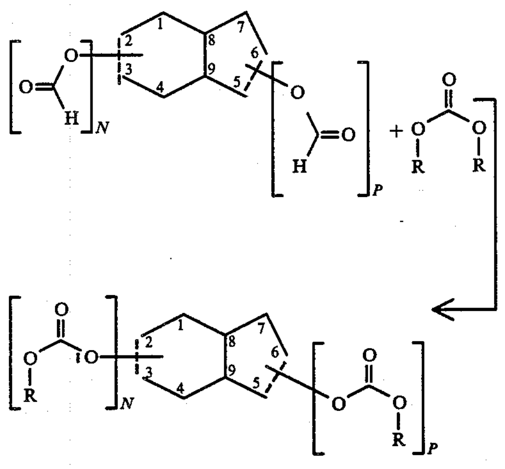

wherein R represents methyl; wherein in the compounds represented by the structures having dashed lines, these structures represent a mixture wherein one of the dashed lines represents a carbon-carbon double bond and the other of the dashed lines represents a carbon-carbon single bond; where N and P are 0 or 1 with the provisos that when N is 1, P is 0 and when N is 0 P is 1 and, further, when N is 1 the dashed line at the "2–3" position is a carbon-carbon single bond and the dashed line at the "5–6" position is a carbon-carbon double bond and when P is 1 the dashed line at the "5–6" position is a carbon-carbon single bond and the dashed line at the "2–3" position is a carbon-carbon double bond.

Into a 2 liter reaction vessel equipped with stirrer, thermometer and reflux condenser are placed 698 grams (3.9 moles) of bicyclononenyl formate produced according to Example I containing compounds having the structures:

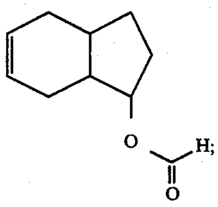
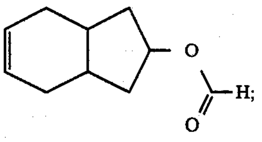

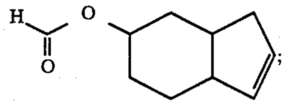
; and
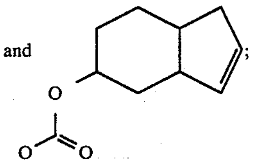

842 grams (9.3 moles) of dimethyl carbonate and 59 grams of 25% sodium methoxide in methyl alcohol (0.27 moles). The reaction mass is stirred at reflux for a period of 1 hour. After the 1 hour period, 24 grams (0.4 moles) of acetic acid is added to the reaction mass and stirring is continued for an additional 30 minutes.

The reaction product is then distilled on a 2" splash column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 43/78 | 50/102 | 2/1 | 95 |
| 2 | 98 | 100 | 1.0 | 163 |
| 3 | 105 | 104 | 1.0 | 101 |
| 4 | 108 | 114 | 1.0 | 258 |
| 5 | 108 | 140 | 1.0 | 123 |
| 6 | 200 | 220 | 1.0 | 88 |

Fractions 2, 3, 4 and 5 are bulked and the bulked fractions are redistilled on an 18" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 65/82 | 110/114 | 4/3.8 | 4:1 | 28 |
| 2 | 85 | 118 | 3.8 | 4:1 | 28 |
| 3 | 72 | 108 | 2.0 | 4:1 | 22 |
| 4 | 65 | 112 | 0.8 | 4:1 | 40 |
| 5 | 75 | 114 | 0.8 | 4:1 | 34 |
| 6 | 76 | 114 | 0.8 | 9:1 | 17 |
| 7 | 78 | 114 | 0.8 | 4:1 | 16 |
| 8 | 79 | 115 | 0.8 | 4:1 | 24 |
| 9 | 82 | 115 | 0.8 | 4:1 | 33 |
| 10 | 82 | 115 | 0.8 | 4:1 | 35 |
| 11 | 82 | 118 | 0.8 | 4:1 | 35 |
| 12 | 82 | 119 | 0.8 | 4:1 | 43 |
| 13 | 82 | 120 | 0.8 | 4:1 | 38 |
| 14 | 85 | 124 | 0.8 | 4:1 | 52 |
| 15 | 88 | 125 | 0.8 | 4:1 | 45 |
| 16 | 88 | 128 | 0.8 | 4:1 | 45 |
| 17 | 89 | 138 | 0.8 | 4:1 | 36 |
| 18 | 89 | 220 | 0.8 | 4:1 | 33 |

Fractions 8 to 17 of the foregoing distillations are bulked and indicated to have a very interesting, fruity, strawberry aroma with fresh, green, banana topnotes.

The resulting reaction product as confirmed by NMR, IR, GLC and mass spectral analyses contains the compounds having the structures:

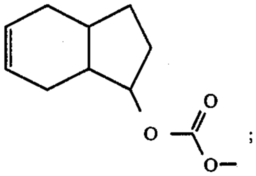
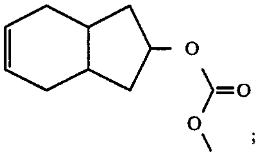

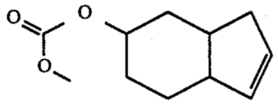
; and

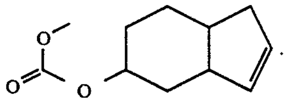

FIG. 9 is the GLC profile for the crude reaction product prior to distillation. The peak indicated by reference numeral 91 is the peak for the mixture of compounds having the structures:

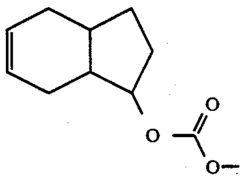
and
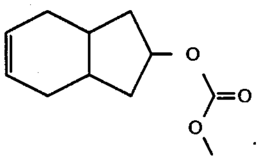

The peak indicated by reference numeral 92 is the peak for the mixture of compounds having the structures:

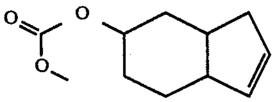
and

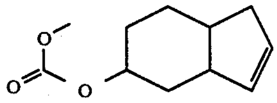

FIG. 10 is the GLC profile for bulked distillation Fractions 10–14 of the foregoing distillation (Conditions: 6'×0.25" 10% SE-30 column programmed at 220° C. isothermal). The single peak at 3.46 is the peak for the mixture of compounds having the structures:

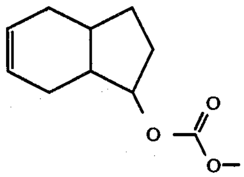
and
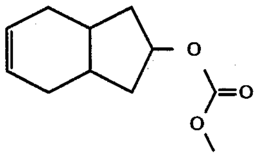

FIG. 11 is the NMR spectrum for peak 91 of the GLC profile of FIG. 9 for the compounds having the structures:

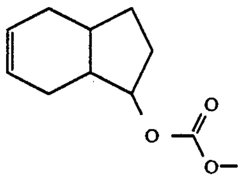

and

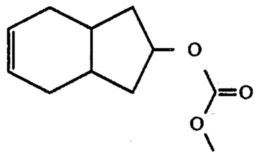

(Conditions: Field strength: 100 MHz; Solvent: $CFCl_3$).

FIG. 12 is the infra-red spectrum for peak 91 of the GLC profile of FIG. 9 for the compounds having the structures:

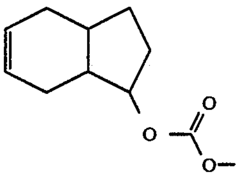

and

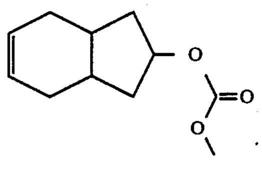

FIG. 13 is the NMR spectrum for peak 92 of the GLC profile of FIG. 9 for the compounds having the structures:

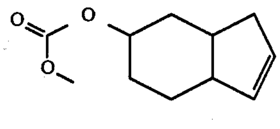

and

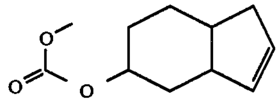

(Conditions: Field strength: 100 MHz; Solvent: $CFCl_3$).

FIG. 14 is the infra-red spectrum for the peak indicated by reference numeral 91 on the GLC profile of FIG. 9 for the compounds having the structures:

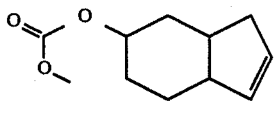

and

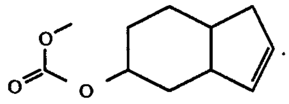

EXAMPLE III

HERBAL FRAGRANCE FORMULATION PREPARED USING PRODUCT PREPARED ACCORDING TO EXAMPLE II

| Ingredients | Parts by Weight |
|---|---|
| Amyl cinnamic aldehyde | 20 |
| Phenyl acetaldehyde dimethyl acetal | 4 |
| Thyme oil white | 8 |
| Sauge sclaree French | 8 |
| Galbanum oil | 4 |
| Juniper berry oil | 10 |
| Methyl octin carbonate | 4 |
| Linalyl acetate | 2 |
| Dihydro methyl jasmonate | 10 |

-continued

| Ingredients | Parts by Weight |
|---|---|
| The bicyclononenyl carbonate mixture prepared according to Example II, bulked distillation Fractions 10-14 | 10 |

The composition of matter containing the bicyclononenyl methyl carbonate mixture prepared according to Example II adds a strong strawberry-like aroma with green, banana topnotes to this herbal fragrance formulation. Accordingly, the resulting formulation can be termed as "herbal with strawberry-like undertones and green banana topnotes.

EXAMPLE IV

PREPARATION OF COSMETIC POWDER COMPOSITIONS

Cosmetic powder compositions are prepared by mixing in a ball mill 100 grams of talcum powder with 0.25 grams of each of the substances set forth in Table I below. Each of the cosmetic powder compositions has an excellent aroma as described in Table I below.

TABLE I

| Substance | Aroma Description |
|---|---|
| Mixture of bicyclononenyl methyl carbonates prepared according to Example II (bulked Fractions 10-14). | A strawberry-like aroma with green banana topnotes. |
| Fragrance formulation of Example III. | Herbal with strawberry-like undertones and green banana topnotes. |

EXAMPLE V

PERFUMED LIQUID DETERGENTS

Concentrated liquid detergents (lysine salt of n-dodecylbenzene sulfonic acid as more specifically described in U.S. Pat. No. 3,948,818 issued Apr. 6, 1976 incorporated by reference herein) with aroma nuances as set forth in Table I of Example IV, are prepared containing 0.10%, 0.15%, 0.20%, 0.25%, 0.30% and 0.35% of the substance set forth in Table I of Example IV. They are prepared by adding and homogeneously mixing the appropriate quantity of substance set forth in Table I of Example IV in the liquid detergent. The detergents all possess excellent aromas as set forth in Table I of Example IV, the intensity increasing with greater concentrations of substance as set forth in Table I of Example IV.

EXAMPLE VI

PREPARATION OF COLOGNES AND HANDKERCHIEF PERFUMES

Compositions as set forth in Table I of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example IV are imparted to the colognes and to the handkerchief perfumes at all levels indicated.

EXAMPLE VII

PREPARATION OF SOAP COMPOSITIONS

One hundred grams of soap chips (per sample) (IVORY ® produced by the proctor & Gamble Company of Cincinnati, Ohio), are each mixed with one gram samples of substances as set forth in Table I of Example IV until homogeneous compositions are obtained. In each of the cases, the homogeneous compositions are heated under 8 atmospheres, pressure at 180° C. for a period of three hours and the resulting liquids are placed into soap molds. The resulting soap cakes, on cooling, manifest aromas as set forth in Table I of Example IV.

EXAMPLE VIII

PREPARATION OF SOLID DETERGENT COMPOSITIONS

Detergents are prepared using the following ingredients according to Example I of Canadian Pat. No. 1,007,948 (incorporated by reference herein):

| Ingredient | Percent by Weight |
|---|---|
| NEODOL ® 45-11 (a $C_{14}$-$C_{15}$ alcohol ethoxylated with 11 moles of ethylene oxide | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example IV. Each of the detergent samples has an excellent aroma as indicated in Table I of Example IV.

EXAMPLE IX

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and the perfuming material are as follows:

1. A water "dissolvable" paper ("Dissolvo Pater");
2. Adogen 448 (m.p. about 140° F.) as the substrate coating and
3. An outer coating having the following formulation (m.p. about 150° F.):
   57% $C_{20-22}$ HAPS
   22% isopropyl alcohol
   20% antistatic agent
   1% of one of the substances as set forth in Table I of Example IV.

Fabric softening compositions prepared according to Example I at column 15 of U.S. Pat. No. 3,632,396 having aroma characteristics as set forth in Table I of Example IV, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener non-woven fabrics and these aroma characteristics are described in Table I of Example IV, supra.

EXAMPLE X

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 Grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid prepared by the Dow Corning Corporation | 0.10 weight percent |
| Tween 20 surfactant (prepared by ICI America Corporation) | 0.03 weight percent |
| One of the perfumery substances as set forth in Table I of Example IV | 0.10 weight percent |

The perfuming substances as set forth in Table I of Example IV add aroma characteristics as set forth in Table I of Example IV which are rather intense and aesthetically pleasing to the users of the soft-feel, good-hold pump hair sprays.

EXAMPLE XI

CONDITIONING SHAMPOOS

Monamid CMA (prepared by the Mona Industries Company) (3.0 weight percent) is melted with 2.0 weight percent coconut fatty acid (prepared by Proctor & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

GAFQUAT ® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "Composition B".

The resulting "Composition A" and "Composition B" are then mixed in a 50:50 weight ratio of A:B and cooled to 45° C. and 0.3 weight percent of perfuming substance as set forth in Table I of Example IV to the mixture. The resulting mixture is cooled to 40° C. and blending is carried out for an additional one hour in each case. At the end of this blending period, the resulting material has a pleasant fragrance as indicated in Table I of Example IV.

EXAMPLE XII

Scented polyethylene pellets having a pronounced scent as set forth in Table I of Example IV are prepared as follows:

75 Pounds of polyethylene of a melting point of about 200° F. are heated to about 230° F. in a container of the kind illustrated in FIGS. 15 and 16. 25 Pounds of each of the perfumery materials of Table I of Example IV, supra are then added quickly to the liquified polyethylene. The lid 228 is put in place and the agitating means 273 are actuated. The temperature is maintained at about 225° F. and the mixing is then continued for about 5–15 minutes. The valve "V" is then opened to allow flow of the molten polyethylene enriched with each of the aroma containing materials to exit through the orifices 234. The liquid falling through the orifices 234 solidify almost instantaneously upon impact with the moving, cooled conveyor 238. Solid polyethylene beads or pellets 244 having pronounced aromas as set forth in Table I of Example IV, supra are then formed. Analysis demonstrates that the pellets contain about 25% of each of the perfume substances of Table I of Example IV so that almost no losses of the scenting substance occur. These pellets may be called master pellets.

50 Pounds of the scent-containing master pellets are then added to 1,000 pounds of unscented polyethylene powder and the mass is heated to the liquid state. The liquid is molded into thin sheets or films. The sheets or films have a pronounced aroma as set forth in Table I of Example IV, supra. The sheets are also fabricated into garbage bags which have aromas as set forth in Table I of Example IV, supra.

EXAMPLE XIII

PREPARATION OF BICYCLONONANYL ETHYL CARBONATE MIXTURE

Reaction:

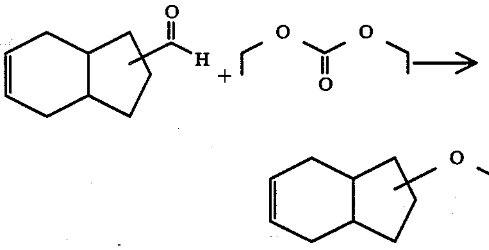

Into a 1 liter reaction vessel equipped with stirrer, thermometer and addition funnel are placed 339 grams (2.04 moles) of bicyclononenyl formate produced according to Example I containing compounds having the structures:

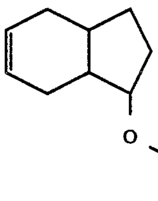

and

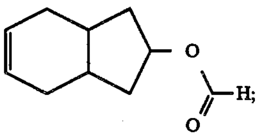

531 grams (4.5 moles) diethyl carbonate; and 31 grams (0.14 moles) of an aqueous 25% solution of sodium methoxide. The resulting mixture is stirred for a period of 1.25 hours. At the end of the 1.25 hour period, 30 grams (0.5 moles) of acetic acid and 2 liters of water is added to the reaction mass with stirring. The reaction mass is then washed with one 2 liter portion of saturated aqueous sodium chloride. The organic phase is then distilled on a 2" splash column yielding the following fractions:

| Fraction No. | Vapor Temp. (°C.) | Liquid Temp. (°C.) | Vacuum mm/Hg. Pressure |
|---|---|---|---|
| 1 | 70/76 | 90/93 | 1.2 |
| 2 | 93 | 108 | 1.2 |
| 3 | 98 | 111 | 1.0 |
| 4 | 103 | 130 | 1.0 |
| 5 | 120 | 200 | 1.0 |

Fractions 2, 3, 4 and 5 from this distillation are bulked and redistilled on an 18" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 52/65 | 107/114 | 0.6/1.6 | 4:1 | 25 |
| 2 | 74 | 118 | 1.6 | 4:1 | 28 |
| 3 | 90 | 118 | 1.6 | 4:1 | 34 |
| 4 | 92 | 118 | 1.6 | 4:1 | 16 |
| 5 | 92 | 118 | 1.6 | 4:1 | 24 |
| 6 | 98 | 124 | 1.8 | 2:1 | 47 |
| 7 | 98 | 128 | 1.8 | 2:1 | 57 |
| 8 | 101 | 165 | 1.8 | 2:1 | 36 |
| 9 | 101 | 225 | 1.7 | 2:1 | 7 |

Fractions 4–9 are bulked for perfumery evaluation.

Bulked fractions 6 and 7 have a rosey, strawberry and banana aroma with floral and fruity topnotes.

FIG. 17 is a GLC profile for the crude reaction product (Conditions: 6'×0.25" 10% SE-30 column programmed at 220° C. isothermal).

FIG. 18 is the GLC profile for bulked fractions 2–5 of the first distillation (Conditions: 6'×0.25" 10% SE-30 column programmed at 220° C. isothermal).

FIG. 19 is the GLC profile for bulked fractions 6 and 7 of the second distillation (Conditions: 6'×0.25" 10% SE-30 column programmed at 220° C. isothermal).

The resulting product contains the compounds having the structures:

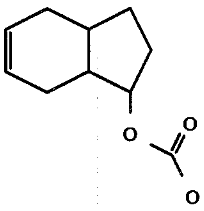

and

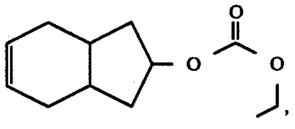

the mixture being shown, thusly:

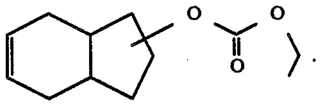

EXAMPLE XIV

PREPARATION OF MIXTURE OF 3A,4,7,7A-TETRAHYDRO-1-INDANOL AND 3A,4,7,7A-TETRAHYDRO-2-INDANOL

Reaction:

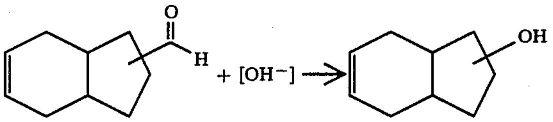

Into a 1 liter reaction vessel equipped with stirrer, thermometer, addition funnel and reflux condenser is placed 240 grams (3 moles) of a 50% aqueous sodium hydroxide solution. Over a period of 10 minutes, with stirring, while maintaining the temperature of the reaction mass at 25°-40° C., 332 grams (2 moles) of the mixture of 3A,4,7,7A-tetrahydro-1-indanyl formate and 3A,4,7,7A-tetrahydro-2-indanyl formate having the structures:

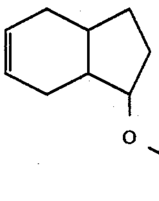

and

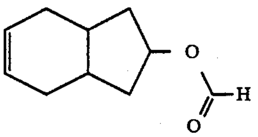

(primarily) produced according to Example I is added to the reaction mass.

75 ml Toluene and 500 ml water are then added to the reaction mass with stirring while maintaining the temperature at 28° C. An additional 100 ml toluene is added and the reaction mass is washed with one 2 liter portion of saturated aqueous sodium chloride.

The organic phase is separated from the aqueous phase and the organic phase is then added to 160 grams of a 50% solution of sodium hydroxide and the resulting product is then heated to 50° C. and maintained at 50° C. for a period of 1.5 hours. At the end of the 1.5 hour period, the reaction mixture is cooled to room temperature and 500 ml water is added. The organic phase is separated from the aqueous phase and the organic phase is washed with one 2 liter portion of satruated sodium chloride followed by one 2 liter portion of 10% hydrochloric acid; followed by one 2 liter portion of aqueous saturated sodium bicarbonate; followed by one 2 liter portion of saturated sodium chloride. The organic phase is separated from the aqueous phase and the organic phase is distilled on a 2" splash column yielding the following fractions:

| Fraction No. | Vapor Temp. (°C.) | Liquid Temp. (°C.) | Vacuum mm/Hg. Pressure |
|---|---|---|---|
| 1 | 78/ | 87/ | 3.0 |
| 2 | 76 | 85 | 1.3 |
| 3 | 76 | 85 | 1.3 |
| 4 | 76 | 85 | 1.3 |
| 5 | 76 | 86 | 1.3 |
| 6 | 76 | 100 | 1.3 |
| 7 | 60 | 190 | 1.3 |

GLC, NMR, IR and mass spectral analyses yield the information that bulked fractions 4-6 of the foregoing distillation are primarily the compounds having the structures:

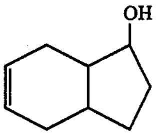

and

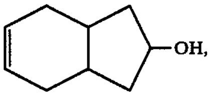

the mixture being represented by the structure:

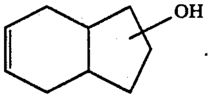

The mixture of compounds defined according to the structure:

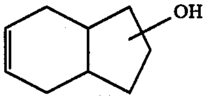

has a woody, piney and minty aroma with spicy topnotes.

FIG. 20 is the GLC profile of the crude reaction product immediately prior to distillation (Conditions: 6'×0.25" 10% SE-30 column programmed at 100°-220° C. at 8° C. per minute).

FIG. 21 is the GLC profile for bulked distillation fractions 4-6 of the foregoing distillation containing the compounds having the structure:

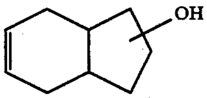

(Conditions: 6'×0.25" 10% SE-30 column programmed at 100°-220° C. at 8° C. per minute).

FIG. 22 is the NMR spectrum for fraction 4 of the foregoing distillation containing the compounds having the structure:

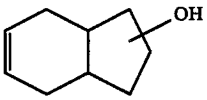

(Conditions: Field strength: 100 MHz; Solvent: $CFCl_3$).

FIG. 23 is the infra-red spectrum for fraction 4 of the foregoing distillation containing the compounds defined according to the structure:

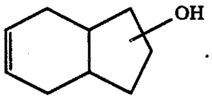

EXAMPLE XV

PREPARATION OF MIXTURE OF 3A,4,7,7A-TETRAHYDRO-1-INDANYL ACETATE AND 3A,4,7,7A-TETRAHYDRO-2-INDANYL ACETATE

Reaction:

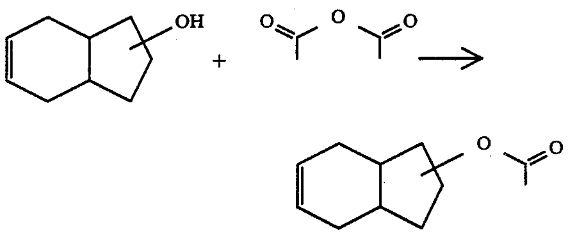

Into a 2 liter reaction vessel equipped with stirrer, thermometer, reflux condenser and heating mantle is placed 510 grams (5 moles) of acetic anhydride. The acetic anhydride is heated to 100° C. with stirring and over a period of 0.3 hours, while maintaining the reaction mass at reflux conditions: 118° C. vapor temperature, 1107 grams (4.5 moles) of the mixture of 3A,4,7,7A-tetrahydro-1-indanol and 3A,4,7,7A-tetrahydro-2-indanol prepared according to Example XIV defined according to the structure:

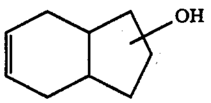

is added to the reaction mass. The reaction mass is continued to be refluxed and over a period of one hour, 205 additional grams of acetic anhydride is added to the reaction mass. The reaction mass is refluxed at 122° C. for an additional hour and then cooled. The reaction mass is combined with 1.8 liters of saturated aqueous sodium chloride solution with stirring. The resulting organic phase is separated from the aqueous phase and the organic phase is washed with two 2 liter portions of aqueous sodium chloride. The aqueous phase is separated from the organic phase and the organic phase is distilled on a 2" splash column yielding the following fractions:

| Fraction No. | Vapor Temp. (°C.) | Liquid Temp. (°C.) | Vacuum mm/Hg. Pressure |
|---|---|---|---|
| 1 | 66/83 | 98/98 | 50/14 |
| 2 | 85 | 90 | 1.2 |
| 3 | 86 | 92 | 1.2 |
| 4 | 93 | 98 | 1.2 |
| 5 | 108 | 140 | 1.2 |

Fractions 2, 3, 4 and 5 are bulked for redistillation and distilled on a one foot Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 28/60 | 78/84 | 1.2/1.0 | 4:1 | 30 |
| 2 | 56 | 84 | 0.8 | 4:1 | 23 |
| 3 | 56 | 84 | 0.8 | 4:1 | 45 |
| 4 | 56 | 84 | 0.8 | 4:1 | 24 |
| 5 | 56 | 84 | 0.8 | 4:1 | 59 |
| 6 | 58 | 84 | 0.8 | 4:1 | 82 |
| 7 | 58 | 84 | 0.8 | 2:1 | 91 |
| 8 | 58 | 84 | 0.8 | 2:1 | 97 |
| 9 | 61 | 87 | 0.8 | 2:1 | 85 |
| 10 | 63 | 87 | 0.8 | 2:1 | 80 |
| 11 | 63 | 92 | 0.8 | 2:1 | 83 |
| 12 | 64 | 96 | 0.8 | 2:1 | 36 |
| 13 | 66 | 104 | 0.8 | 2:1 | 20 |
| 14 | 67 | 162 | 0.8 | 2:1 | 27 |
| 15 | 67 | 222 | 0.8 | 2:1 | 11 |

Bulked fractions 7–10 of the immediately foregoing distillation has a fruity, jasmine and minty aroma profile.

GLC, IR, NMR and mass spectral anaylses yield the information that the resulting bulked distillation fractions 7–10 contain, primarily, the compounds having the structures:

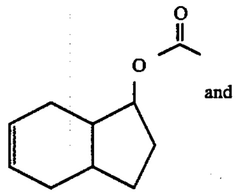

and

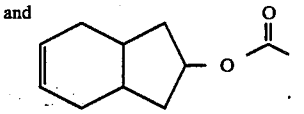

the mixture being indicated by the structure:

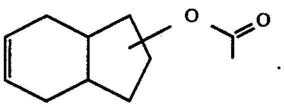

FIG. 24 is the GLC profile for the crude reaction product prior to distillation containing the compounds having the structure

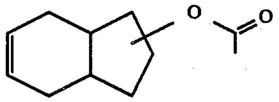

(Conditions: 6'×0.25" 10% SE-30 column).

FIG. 25 is the GLC profile for bulked fractions 2–5 of the first distillation containing the compounds having the structure:

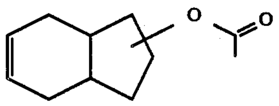

(Conditions: 6'×0.25" 10% SE-30 column programmed at 220° C. isothermal).

FIG. 26 is the GLC profile for bulked fractions 7–10 of the second distillation, supra, containing the compounds having the structure:

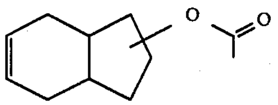

(Conditions: 6′×0.25″ 10% SE-30 column programmed at 220° C. isothermal).

FIG. 27 is the NMR spectrum for fraction 8 of the second distillation containing the compounds having the structure:

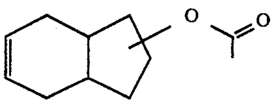

(Conditions: Field strength: 100 MHz; Solvent: $CFCl_3$).

FIG. 28 is the infra-red spectrum for fraction 8 of the second distillation containing the compounds having the structure:

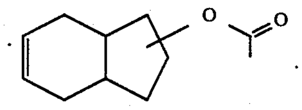

EXAMPLE XVI

PREPARATION OF MIXTURE OF 3A,4,7,7A-TETRAHYDRO-1-INDANYL PROPIONATE AND 3A,4,7,7A-TETRAHYDRO-2-INDANYL PROPIONATE

Reaction:

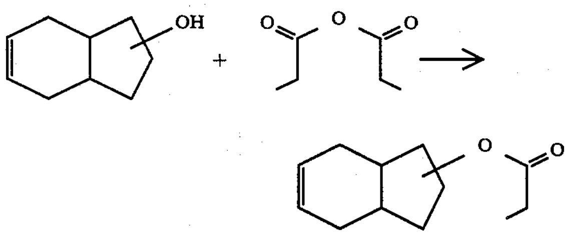

Into a 2 liter reaction vessel equipped with stirrer, thermometer, reflux condenser and addition funnel is placed 510 grams (3.9 moles) of propionic anhydride. The propionic anhydride, with stirring is heated to 100° C. While maintaining the propionic anhydride at 100° C., over a period of 0.3 hours, 900 grams (3.4 moles) of the mixture of 3A,4,7,7A-tetrahydro-1-indanol and 3A,4,7,7A-tetrahydro-2-indanol prepared according to Example XIV is added to the propionic anhydride. The temperature in the reaction vessel is raised to 117° C. and 130 grams of additional propionic anhydride is added with stirring over a period of 0.3 hours. The temperature of the reaction vessel is raised to 127° C. and an additional 65 grams of propionic anhydride is added to the reaction mass. The reaction mass is continued to be stirred at 127° C. for a period of 1.5 hours. At the end of the reaction period, the reaction mass is cooled.

2 Liters of water is added to the reaction mass and the organic phase is separated from the aqueous phase. The organic phase is then washed as follows:

(i) one 2 liter portion of saturated sodium chloride;
(ii) one 2 liter portion of saturated sodium bicarbonate; and
(iii) one 2 liter portion of saturated sodium chloride.

The organic phase is then fractionally distilled on a 2″ splash column yielding the following fractions:

| Fraction No. | Vapor Temp. (°C.) | Liquid Temp. (°C.) | Vacuum mm/Hg. Pressure |
|---|---|---|---|
| 1 | 63/70 | 98/100 | 1.6/1.6 |
| 2 | 84 | 98 | 1.6 |
| 3 | 88 | 100 | 1.6 |
| 4 | 92 | 102 | 1.6 |
| 5 | 95 | 106 | 1.6 |
| 6 | 106 | 125 | 1.6 |
| 7 | 120 | 200 | 1.6 |

Distillation fractions 3–7 are bulked and redistilled on a one foot Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 30/66 | 87/91 | 0.8/0.8 | 4:1 | 17 |
| 2 | 67 | 91 | 0.8 | 4:1 | 23 |
| 3 | 67 | 91 | 0.8 | 4:1 | 10 |
| 4 | 65 | 91 | 0.8 | 9:1 | 47 |
| 5 | 65 | 91 | 0.8 | 9:1 | 16 |
| 6 | 65 | 91 | 0.8 | 9:1 | 5 |
| 7 | 65 | 91 | 0.8 | 4:1 | 21 |
| 8 | 65 | 91 | 0.7 | 2:1 | 74 |
| 9 | 67 | 93 | 0.7 | 2:1 | 91 |
| 10 | 67 | 93 | 0.7 | 2:1 | 88 |
| 11 | 67 | 94 | 0.7 | 2:1 | 93 |
| 12 | 68 | 97 | 0.7 | 2:1 | 100 |
| 13 | 72 | 114 | 0.7 | 2:1 | 86 |
| 14 | 73 | 150 | 0.7 | 2:1 | 26 |
| 15 | 74 | 220 | 0.7 | 2:1 | 7 |

NMR, IR and mass spectral anaylses confirm that the resulting product is primarily a mixture of compounds having the structures:

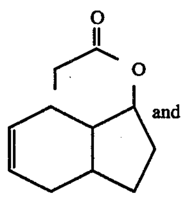

and

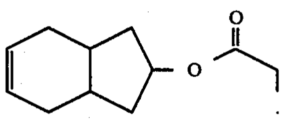

Bulked fractions 8–11 of the second distillation has an intense banana aroma with fruity, floral, hawthorne, ozoney and anisic topnotes.

FIG. 29 is the GLC profile for the crude reaction product prior to distillation (Conditions: 6′×0.25″ 10% SE-30 column programmed at 220° C. isothermal).

FIG. 30 is the GLC profile for bulked fractions 3–7 for the first distillation (Conditions: 6′×0.25″ 10% SE-30 column programmed at 220° C. isothermal).

FIG. 31 is the GLC profile for bulked fractions 8–11 of the second distillation (Conditions: 6′×0.25″ 10% SE-30 column programmed at 220° C. isothermal).

FIG. 32 is the NMR spectrum for fraction 6 of the second distillation containing the compounds having the structures:

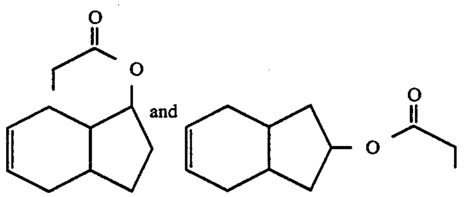

(Conditions: Field strength: 100 MHz; Solvent: $CFCl_3$).

FIG. 33 is the infra-red spectrum for fraction 6 of the second distillation containing the compounds having the structures:

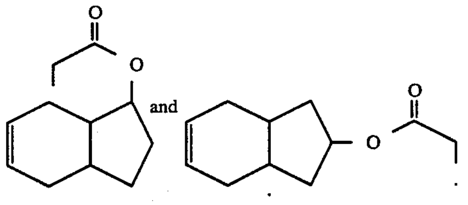

EXAMPLE XVII

PREPARATION OF MIXTURE OF 3A,4,7,7A-TETRAHYDRO-1-INDANONE AND 3A,4,7,7A-TETRAHYDRO-2-INDANONE

Reaction:

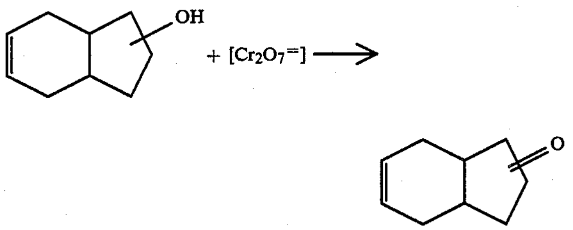

Into a 1 liter reaction vessel equipped with stirrer, thermometer, reflux condenser and cooling coils are placed 235 grams (0.8 moles) of potassium dichromate. A mixture of 200 grams of concentrated sulfuric acid (93% aqueous) and 1200 grams of ice is then added to the potassium dichromate. 25 Grams (0.41 moles) of isopropyl alcohol and 103.5 grams (0.75 moles) of the mixture of 3A,4,7,7A-tetrahydro-1-indanol and 3A,4,7-,7A-tetrahydro-2-indanol prepared according to Example XIV, supra (bulked distillation fractions 2–6). The resulting isopropyl alcohol-bicyclononenol mixture is slowly added to the mixture of sulfuric acid and potassium dichromate over a period of 1 hour while maintaining the temperature of the reaction mass at 6°–35° C. At the end of the addition period, 50 ml additional ispropyl alcohol is added.

While maintaining the reaction mass at 35°–38° C., 150 ml toluene is added to the reaction mass. The resulting organic phase is then washed with three volumes of a 5% aqueous solution of sodium hydroxide followed by two 500 ml portions of saturated sodium chloride. The resulting organic phase is then distilled on a micro distillation apparatus yielding the following fractions:

| Fraction No. | Vapor Temp. (°C.) | Liquid Temp. (°C.) | Vacuum mm/Hg. Pressure |
|---|---|---|---|
| 1 | 72/72 | 84/84 | 1.2/1.2 |
| 2 | 66 | 80 | 1.0 |
| 3 | 64 | 80 | 0.8 |
| 4 | 64 | 80 | 0.8 |
| 5 | 64 | 81 | 0.8 |
| 6 | 58 | 160 | 0.8 |

Bulked fractions 4 and 5 have an intense woody aroma with fruity topnotes.

EXAMPLE XVIII

HERBAL FRAGRANCE FORMULATIONS PREPARED USING PRODUCTS PREPARED ACCORDING TO EXAMPLES XIII, XIV, XV, XVI AND XVII

| | Parts by Weight | | | | |
|---|---|---|---|---|---|
| Ingredients | A | B | C | D | E |
| Amyl cinnamic aldehyde | 20 | 20 | 20 | 20 | 20 |
| Phenyl acetaldehyde dimethyl acetal | 4 | 4 | 4 | 4 | 4 |
| Thyme oil white | 8 | 8 | 8 | 8 | 8 |
| Sauge sclaree French | 8 | 8 | 8 | 8 | 8 |
| Galbanum oil | 4 | 4 | 4 | 4 | 4 |
| Juniper berry oil | 10 | 10 | 10 | 10 | 10 |
| Methyl octin carbonate | 4 | 4 | 4 | 4 | 4 |
| Linalyl acetate | 2 | 2 | 2 | 2 | 2 |
| Dihydro methyl jasmonate | 10 | 10 | 10 | 10 | 10 |
| Mixture of compounds defined by the structure: 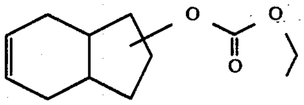 prepared according to Example XIII, bulked distillation fractions 6 and 7. | 10 | 0 | 0 | 0 | 0 |
| Mixture of compounds defined according to the structure: 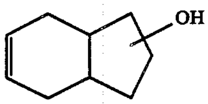 prepared according to Example XIV (bulked fractions 4–6). | 0 | 10 | 0 | 0 | 0 |
| Mixture of compounds defined according to the structure: 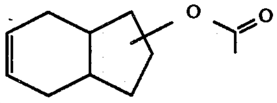 prepared according to Example XV, bulked distillation fractions 7–10. | 0 | 0 | 10 | 0 | 0 |
| Mixture of compounds defined according to the structure: 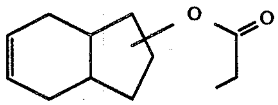 prepared according to Example XVI, bulked distillation fractions 8–11. | 0 | 0 | 0 | 10 | 0 |
| Mixture of compounds defined according to the structure: | 0 | 0 | 0 | 0 | 10 |

-continued

| Ingredients | Parts by Weight A | B | C | D | E |
|---|---|---|---|---|---|
| 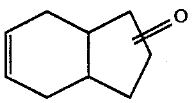 prepared according to Example XVII, bulked distillation fractions 4 and 5. | | | | | |

The mixture of compounds defined according to the structure:

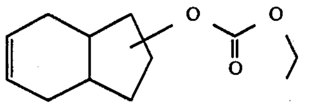

prepared according to Example XIII adds rosey, strawberry and banana undertones with floral and fruity topnotes to this herbal formulation. Accordingly, the resulting perfume composition can be described as having a "herbal aroma with rosey, strawberry and banana undertones with floral and fruity topnotes".

The mixture of compounds defined according to the structure:

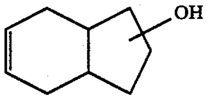

prepared according to Example XIV imparts to the herbal formulation woody, piney and minty undertones and spicy topnotes. Accordingly, the perfume composition of Example XVIII(B) can be described as "herbal with woody, piney and minty undertones and spicy topnotes".

The mixture of compounds defined according to the structure:

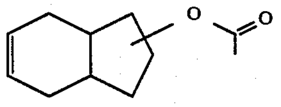

prepared according to Example XV imparts to this herbal formulation fruity, jasmine and minty undertones. Accordingly, the resulting perfume composition of Example XVIII(C) can be described as "herbal with fruity, jasmine and minty undertones".

The mixture of compounds defined according to the structure:

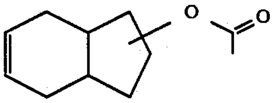

prepared according to Example XVI imparts to this herbal formulation a banana undertone with fruity, floral, hawthorne, ozoney and anisic topnotes. Accordingly, the resulting perfume composition of Examle XVIII (D) can be described as "herbal with banana undertones and fruity, floral, hawthorne, ozoney and anisic topnotes".

The mixture of compound defined according to the structure:

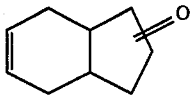

prepared according to Example XVII imparts to this herbal formulation a woody undertone with fruity topnotes. Accordingly, the resulting herbal formulation of Example XVIII (E) can be described as "herbal having a woody undertone and fruity topnotes".

EXAMPLE XIX

PREPARATION OF COSMETIC POWDER COMPOSITIONS

Cosmetic powder compositions are prepared by mixing in a ball mill 100 grams of talc powder with 0.25 grams of each of the substances set forth in Table II, below. Each of the cosmetic powder compositions has an excellent aroma as described in Table II below.

TABLE II

| Substance | Aroma Description |
|---|---|
| Mixture of compounds having the structure: 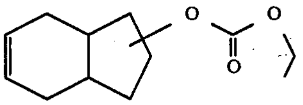 prepared according to Example XIII (bulked fractions 6 and 7). | A rosey, strawberry and banana aroma with floral and fruity topnotes. |
| Mixture of compounds defined according to the structure: 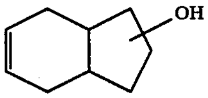 prepared according to Example XIV (bulked fractions 4–6). | A woody, piney, minty aroma with spicy topnotes. |
| Mixture of compounds defined according to the structure: 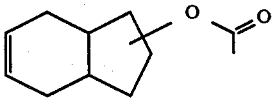 prepared according to Example XV (bulked fractions 7–10). | A fruity, jasmine and minty aroma. |
| Mixture of compounds defined according to the structure: | A banana aroma with fruity, floral, hawthorne, ozoney and anisic topnotes. |

TABLE II-continued

| Substance | Aroma Description |
|---|---|
| 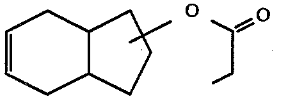 prepared according to Example XVI (bulked fractions 8-11). | |
| Mixture of compounds defined according to the structure: 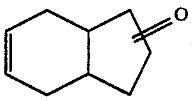 prepared according to Example XVII (bulked fractions 4 and 5). | A woody aroma with fruity topnotes. |
| Perfume composition of Example XVIII(A). | A herbal aroma with rosey, strawberry and banana undertones with floral and fruity topnotes. |
| Perfume composition of Example XVIII(B). | Herbal with woody, piney and minty undertones and spicy topnotes. |
| Perfume composition of Example XVIII(C). | Herbal with fruity, jasmine and minty undertones. |
| Perfume composition of Example XVIII(D). | Herbal with banana undertones and fruity, floral, hawthorne, ozoney and anisic topnotes. |
| Perfume composition of Example XVIII(E). | Herbal having a woody undertone and fruity topnotes. |

EXAMPLE XX

PERFUMED LIQUID DETERGENTS

Concentrated liquid detergents (lysine salt of n-dodecylbenzene sulfonic acid as more specifically described in U.S. Pat. No. 3,948,818 issued Apr. 6, 1976 incorporated by reference herein) with aroma nuances as set forth in Table II of Example XIX are prepared containing 0.10%, 0.15%, 0.20%, 0.25%, 0.30% and 0.35% of the substance set forth in Table II of Example XIX. They are prepared by adding and homogeneously mixing the appropriate quantity of substance set forth in Table II of Example XIX in the liquid detergent. The detergents all possess excellent aromas as set forth in Table II of Example XIX, the intensity increasing with greater concentrations of substance as set forth in Table II of Example XIX.

EXAMPLE XXI

PREPARATION OF COLOGNES AND HANDKERCHIEF PERFUMES

Compositions as set forth in Table II of Example XIX are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example XIX are imparted to the colognes and to the handkerchief perfumes at all levels indicated.

EXAMPLE XXII

PREPARATION OF SOAP COMPOSITIONS

One hundred grams of soap chips (per sample) (IVORY ® produced by the Procter & Gamble Company of Cincinnati, Ohio), are each mixed with one gram samples of substances as set forth in Table II of Example XIX until homogeneous compositions are obtained. In each of the cases, the homogeneous compositions are heated under 8 atmospheres, pressure at 180° C. for a period of three hours and the resulting liquids are placed into soap molds. The resulting soap cakes, on cooling, manifest aromas as set forth in Table II of Example XIX.

EXAMPLE XXIII

PREPARATION OF SOLID DETERGENT COMPOSITIONS

Detergents are prepared using the following ingredients according to Example I of Canadian Pat. No. 1,007,948 (incorporated by reference herein):

| Ingredient | Percent by Weight |
|---|---|
| NEODOL ® 45-11 (a $C_{14}$-$C_{15}$ alcohol ethoxylated with 11 moles of ethylene oxide | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example XIX. Each of the detergent samples has an excellent aroma as indicated in Table II of Example XIX.

EXAMPLE XXIV

Utilizing the procedure of Example I at column 15 of U.S. Pat. No. 3,632,396 (the disclosure of which is incorporated herein by reference), non-woven cloth substrates useful as drier-added fabric sofening articles of manufacture are prepared wherein the substrate, the substrate coating, the outer coating and the perfuming material are as follows:

1. A water "dissolvable" paper ("Dissolvo Pater");
2. Adogen 448 (m.p. about 140° F.) as the substrate coating; and
3. An outer coating having the following formulation (m.p. about 150° F. ):
   57% $C_{20-22}$ HAPS
   22% isopropyl alcohol
   20% antistatic agent
   1% of one of the substances as set forth in Table II of Example XIX.

Fabric softening compositions prepared according to Example I at column 15 of U.S. Pat. No. 3,632,396 having aroma characteristics as set forth in Table II of Example XIX, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example XIX is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener non-woven fabrics and these aroma characteristics are described in Table II of Example XIX, supra.

EXAMPLE XXV

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 Grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid prepared by the Dow Corning Corporation | 0.10 weight percent |
| Tween 20 surfactant (prepared by ICI America Corporation) | 0.03 weight percent |
| One of the perfumery substances as set forth in Table II of Example XIX. | 0.10 weight percent |

The perfuming substances as set forth in Table II of Example XIX add aroma characteristics as set forth in Table II of Example XIX which are rather intense and aesthetically pleasing to the users of the soft-feel, good-hold pump hair sprays.

EXAMPLE XXVI

CONDITIONING SHAMPOOS

Monamide CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A").

GAFQUAT® 755N polymer (manufactured by GAF Corporation of 140 West 51st Street, New York, N.Y. (5.0 weight percent) is admixed with 0.1 weight percent sodium sulfite and 1.4 weight percent polyethylene glycol 6000 distearate produced by Armak Corporation. This material is "Composition B".

The resulting "Composition A" and "Composition B" are then mixed in a 50:50 weight ratio of A:B and cooled to 45° C. and 0.3 weight percent of perfuming substance as set forth in Table II Example XIX to the mixture. The resulting mixture is cooled to 40° C. and blending is carried out for an additional one hour in each case. At the end of this blending period, the resulting material has a pleasant fragrance as indicated in Table II of Example XIX.

EXAMPLE XXVII

Scented polyethylene pellets having a pronounced scent as set forth in Table II of Example XIX are prepared as follows:

75 Pounds of polyethylene of a melting point of about 200° F. are heated to about 230° F. in a container of the kind illustrated in FIGS. 15 and 16. 25 Pounds of each of the perfumery materials of Table II of Example XIX, supra are then added quickly to the liquified polyethylene. The lid 228 is put in place and the agitating means 273 are actuated. The temperature is maintained at about 225° F. and the mixing is then continued for about 5–15 minutes. The valve "V" is then opened to allow flow of the molten polyethylene enriched with each of the aroma containing materials to exit through the orifices 234. The liquid falling through the orifices 234 solidify almost instantaneously upon impact with the moving, cooled conveyor 238. Solid polyethylene beads or pellets 244 having pronounced aromas as set forth in Table II of Example XIX, supra, are then formed. Analysis demonstrates that the pellets contain about 25% of each of the perfume substances of Table II of Example XIX so that almost no losses of the scenting substance occur. These pellets may be called master pellets.

50 Pounds of the scent-containing master pellets are then added to 1,000 pounds of unscented polyethylene powder and the mass is heated to the liquid state. The liquid is molded into thin sheets or films. The sheets or films have a pronounced aroma as set forth in Table II of Example XIX, supra. The sheets are also fabricated into garbage bags which have aromas as set forth in Table II of Example XIX, supra.

What is claimed is:

1. A process for augmenting or enhancing the aroma of a liquid perfume composition comprising the step of intimately admixing with said liquid perfume composition an aroma augmenting or enhancing quantity of a mixture of compounds, bicyclononenyl alcohols comprising alcohols defined according to the structure:

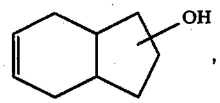

produced according to the process consisting essentially of the steps:

(i) forming a mixture of bicyclononene formates by reaction of bicyclononadiene with formic acid at reflux conditions for a period of time sufficient to produce a product containing greater than 80% bicyclononene formates, with the mole ratio of formic acid:bicyclononadiene varying between about 2:1 up to about 7:1 and then fractionally distilling the resulting product, the bicyclononene formates; and then (ii) hydrolyzing the resulting bicyclononene formates using strong base wherein the mole ratio of hydroxyl ion:formates being between about 2:1 and about 1:1, the reaction temperature varying between about 40° C. and 60° C.; and (iii) then neutralizing the resulting reaction mass and fractionally distilling the resulting product comprising the mixture of compounds defined according to the structure:

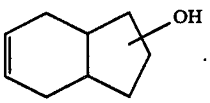.

2. A process for augmenting or enhancing the aroma of a solid or liquid anionic, cationic, nonionic or zwitterionic detergent comprising the step of intimately admixing with said solid or liquid anionic, cationic, nonionic or zwitterionic detergent an aroma augmenting or enhancing quantity of a mixture of compounds comprising compounds having the structure:

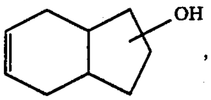, produced according to the process consisting essentially of the steps of:

(i) forming a mixture of bicyclononene formates by reaction of bicyclononadiene with formic acid at reflux conditions for a period of time sufficient to produce a product containing greater than 80% bicyclononene formates, with the mole ratio of formic acid:bicyclononadiene varying between about 2:1 up to about 7:1 and then fractionally distilling the resulting product, the bicyclononene formates; and then (ii) hydrolyzing the resulting bicyclononene formates using strong base wherein the mole ratio of hydroxyl ion:formates being between about 2:1 and about 1:1, the reaction temperature varying between about 40° C. and 60° C.; and (iii) then neutralizing the resulting reaction mass and fractionally distilling the resulting product comprising the mixture of compounds defined according to the structure:

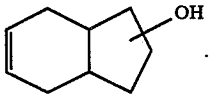.

3. A process for augmenting or enhancing the aroma of a fabric softener composition or a fabric softener article comprising the step of intimately admixing with said fabric softener composition or a fabric softener article an aroma augmenting or enhancing quantity of a mixture of compounds comprising compounds having the structure:

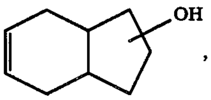, produced according to the process consisting essentially of the steps of:

(i) forming a mixture of bicyclononene formates by reaction of bicyclononadiene with formic acid at reflux conditions for a period of time sufficient to produce a product containing greater than 80% bicyclononene formates, with the mole ratio of formic acid:bicyclononadiene varying between about 2:1 up to about 7:1 and then fractionally distilling the resulting product, the bicyclononene formates; and then (ii) hydrolyzing the resulting bicyclononene formates using strong base wherein the mole ratio of hydroxyl ion:formates being between about 2:1 and about 1:1, the reaction temperature varying between about 40° C. and 60° C.; and (iii) then neutralizing the resulting reaction mass and fractionally distilling the resulting product comprising the mixture of compounds defined according to the structure:

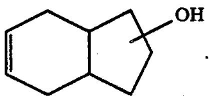.

4. A process for augmenting or enhancing the aroma of a perfumed polymer comprising the steps of intimately admixing with said perfumed polymer an aroma augmenting or enhancing quantity of a material comprising a mixture of compounds defined according to the structure:

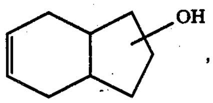, produced according to the process consisting essentially of the steps of:

(i) forming a mixture of bicyclononene formates by reaction of bicyclononadiene with formic acid at reflux conditions for a period of time sufficient to produce a product containing greater than 80% bicyclononene formates, with the mole ratio of formic acid:bicyclononadiene varying between about 2:1 up to about 7:1 and then fractionally distilling the resulting product, the bicyclononene formates; and then (ii) hydrolyzing the resulting bicyclononene formates using strong base wherein the mole ratio of hydroxyl ion:formates being between about 2:1 and about 1:1, the reaction temperature varying between about 40° C. and 60° C.; and (iii) then neutralizing the resulting reaction mass and fractionally distilling the resulting product comprising the mixture of compounds defined according to the structure:

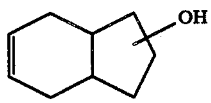

* * * * *